US012227787B2

United States Patent
Ito et al.

(10) Patent No.: US 12,227,787 B2
(45) Date of Patent: *Feb. 18, 2025

(54) METHOD OF EVALUATING QUALITY OF DEPHOSPHORYLATION REAGENT AND METHOD OF DETECTING TARGET NUCLEIC ACID

(71) Applicant: Toray Industries, Inc., Tokyo-to (JP)

(72) Inventors: Masateru Ito, Kamakura (JP); Yoji Ueda, Kamakura (JP); Yuki Takii, Kamakura (JP); Mai Yagi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 919 days.

This patent is subject to a terminal disclaimer.

(21) Appl. No.: 17/280,056

(22) PCT Filed: Sep. 25, 2019

(86) PCT No.: PCT/JP2019/037518
§ 371 (c)(1),
(2) Date: Mar. 25, 2021

(87) PCT Pub. No.: WO2020/067120
PCT Pub. Date: Apr. 2, 2020

(65) Prior Publication Data
US 2022/0033874 A1    Feb. 3, 2022

(30) Foreign Application Priority Data

Sep. 25, 2018 (JP) .................................. 2018-179529

(51) Int. Cl.
| | | |
|---|---|---|
| *C12Q 1/42* | (2006.01) | |
| *C12N 9/16* | (2006.01) | |
| *C12Q 1/6816* | (2018.01) | |
| *G01N 30/72* | (2006.01) | |
| *G01N 30/74* | (2006.01) | |
| *G01N 30/86* | (2006.01) | |
| *G01N 33/68* | (2006.01) | |
| *G01N 30/02* | (2006.01) | |

(52) U.S. Cl.
CPC .................. *C12Q 1/42* (2013.01); *C12N 9/16* (2013.01); *C12Q 1/6816* (2013.01); *G01N 30/7233* (2013.01); *G01N 30/74* (2013.01); *G01N 30/8679* (2013.01); *G01N 33/6848* (2013.01); *C12Y 301/03001* (2013.01); *G01N 2030/027* (2013.01); *G01N 2410/00* (2013.01)

(58) Field of Classification Search
CPC ........ C12Q 1/42; C12N 9/16; G01N 33/6848; G01N 30/8679; G01N 2410/00; G01N 2030/027; C12Y 301/03001
See application file for complete search history.

(56) References Cited

U.S. PATENT DOCUMENTS

| | | | |
|---|---|---|---|
| 5,705,610 A | 1/1998 | Zuckermann et al. | |
| 5,807,522 A | 9/1998 | Brown et al. | |
| 7,037,659 B2 | 5/2006 | Cerrina et al. | |
| 2002/0155481 A1 | 10/2002 | Hirota et al. | |
| 2007/0148140 A1 | 6/2007 | Kiss | |
| 2008/0098491 A1 | 4/2008 | Kiss | |
| 2014/0030790 A1 | 1/2014 | Aiba et al. | |
| 2021/0332337 A1* | 10/2021 | Ueda .............. | C12Y 301/03001 |
| 2021/0395708 A1* | 12/2021 | Ito ........................... | C12P 19/34 |

FOREIGN PATENT DOCUMENTS

| | | | |
|---|---|---|---|
| JP | 10-503841 A | 4/1998 | |
| JP | 10-262674 A | 10/1998 | |
| JP | 3922454 B2 | 5/2007 | |
| WO | 2012/115023 A1 | 8/2012 | |
| WO | 2013/096862 A2 | 6/2013 | |
| WO | WO-2017031114 A1 * | 2/2017 | ........... A61K 38/465 |

OTHER PUBLICATIONS

Pozidis et al. Bioseparation, 1995, 5, 89-93 (Year: 1995).*
Polakowski et al. J. Am. Chem. Soc., 2000, 122, 4853-4855 (Year: 2000).*
Pozidis, C. et al., "Preparation of high purity alkaline phosphatase from calf intestine using dye-ligand chromatography," *Bioseparation*, 1995, vol. 5, No. 2, pp. 89-93.
Extended European Search Report dated Jul. 7, 2022, of counterpart European Patent Application No. 19866901.2.
T. Manes et al., "Genetic Complexity, Structure, and Characterization of Highly Active Bovine Intestinal Alkaline Phosphatases," Journal of Biological Chemistry, vol. 273, No. 36, pp. 23353-23360, 1998.
First Office Action dated Aug. 30, 2023, of counterpart Chinese Patent Application No. 201980071617.3, along with an English translation.
Notice of Reasons for Refusal dated Sep. 5, 2023, of counterpart Japanese Patent Application No. 2019-554582, along with an English translation.

* cited by examiner

*Primary Examiner* — Sharmila G Landau
*Assistant Examiner* — Lioubov G Korotchkina
(74) *Attorney, Agent, or Firm* — DLA Piper LLP (US)

(57) ABSTRACT

A method evaluates a quality of a dephosphorylation reagent, the method including the steps of: providing a dephosphorylation reagent containing an alkaline phosphatase and a peptide fragment derived from the alkaline phosphatase; and evaluating the dephosphorylation reagent as having a high quality if a content ratio of the peptide fragment to the alkaline phosphatase is a predetermined reference value or less.

7 Claims, 19 Drawing Sheets
Specification includes a Sequence Listing.

SEQUENCE LISTING

```
<160> NUMBER OF SEQ ID NOS: 10

<210> SEQ ID NO 1
<211> LENGTH: 24
<212> TYPE: PRT
<213> ORGANISM: Bos taurus

<400> SEQUENCE: 1

Glu Ala Glu Ala Glu Phe Leu Ile Pro Ala Glu Glu Glu Asn Pro Ala
1               5                   10                  15
```

```
Phe Trp Asn Arg Gln Ala Ala Gln
            20

<210> SEQ ID NO 2
<211> LENGTH: 13
<212> TYPE: PRT
<213> ORGANISM: Bos taurus

<400> SEQUENCE: 2

Glu Gly Val Ser Leu Glu Lys Arg Glu Ala Glu Ala Glu
1               5                   10

<210> SEQ ID NO 3
<211> LENGTH: 13
<212> TYPE: PRT
<213> ORGANISM: Bos taurus

<400> SEQUENCE: 3

Ile Pro Ala Glu Glu Asn Pro Ala Phe Trp Asn Arg
1               5                   10

<210> SEQ ID NO 4
<211> LENGTH: 11
<212> TYPE: PRT
<213> ORGANISM: Bos taurus

<400> SEQUENCE: 4

Asp Arg Gln Val Pro Asp Ser Ala Gly Thr Ala
1               5                   10

<210> SEQ ID NO 5
<211> LENGTH: 9
<212> TYPE: PRT
<213> ORGANISM: Bos taurus

<400> SEQUENCE: 5

Ala Pro Gly Lys Ala Leu Asp Ser Lys
1               5

<210> SEQ ID NO 6
<211> LENGTH: 16
<212> TYPE: PRT
<213> ORGANISM: Bos taurus

<400> SEQUENCE: 6

Val Pro Leu Ala Ser Glu Thr His Gly Gly Glu Asp Val Ala Val Phe
1               5                   10                  15

<210> SEQ ID NO 7
<211> LENGTH: 13
<212> TYPE: PRT
<213> ORGANISM: Bos taurus

<400> SEQUENCE: 7

Val Pro Leu Ala Ser Glu Thr His Gly Gly Glu Asp Val
1               5                   10

<210> SEQ ID NO 8
<211> LENGTH: 18
<212> TYPE: PRT
<213> ORGANISM: Bos taurus

<400> SEQUENCE: 8

Gly Pro Gln Ala His Leu Val His Gly Val Gln Glu Glu Thr Phe Val
1               5                   10                  15
```

Ala His

<210> SEQ ID NO 9
<211> LENGTH: 12
<212> TYPE: PRT
<213> ORGANISM: Bos taurus

<400> SEQUENCE: 9

```
Gly Pro Gln Ala His Leu Val His Gly Val Gln Glu
1               5                   10
```

<210> SEQ ID NO 10
<211> LENGTH: 578
<212> TYPE: PRT
<213> ORGANISM: Bos taurus

<400> SEQUENCE: 10

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Leu Ile Pro Ala Glu
                85                  90                  95

Glu Glu Asn Pro Ala Phe Trp Asn Arg Gln Ala Gln Ala Leu Asp
            100                 105                 110

Val Ala Lys Lys Leu Gln Pro Ile Gln Thr Ala Ala Lys Asn Val Ile
    115                 120                 125

Leu Phe Leu Gly Asp Gly Met Gly Val Pro Thr Val Thr Ala Thr Arg
130                 135                 140

Ile Leu Lys Gly Gln Met Asn Gly Lys Leu Gly Pro Glu Thr Pro Leu
145                 150                 155                 160

Ala Met Asp Gln Phe Pro Tyr Val Ala Leu Ser Lys Thr Tyr Asn Val
                165                 170                 175

Asp Arg Gln Val Pro Asp Ser Ala Gly Thr Ala Thr Ala Tyr Leu Cys
            180                 185                 190

Gly Val Lys Gly Asn Tyr Arg Thr Asn Gly Lys Leu Gly Pro Glu Thr
    195                 200                 205

Pro Leu Ala Met Asp Gln Phe Pro Tyr Val Ala Leu Ser Lys Thr Tyr
    210                 215                 220

Asn Val Asp Arg Gln Val Pro Asp Ser Ala Gly Thr Ala Thr Ala Tyr
225                 230                 235                 240

Leu Cys Gly Val Lys Gly Asn Tyr Arg Thr Tyr Ala His Thr Val Asn
                245                 250                 255

Arg Asn Trp Tyr Ser Asp Ala Asp Leu Pro Ala Asp Ala Gln Lys Asn
            260                 265                 270

Gly Cys Gln Asp Ile Ala Ala Gln Leu Val Tyr Asn Met Asp Ile Asp
    275                 280                 285

Val Ile Leu Gly Gly Gly Arg Met Tyr Met Phe Pro Glu Gly Thr Pro
    290                 295                 300
```

```
Asp Pro Glu Tyr Pro Asp Asp Ala Ser Val Asn Gly Val Arg Lys Asp
305             310             315             320

Lys Gln Asn Leu Val Gln Glu Trp Gln Ala Lys His Gln Gly Ala Gln
            325             330             335

Tyr Val Trp Asn Arg Thr Ala Leu Leu Gln Ala Ala Asp Asp Ser Ser
            340             345             350

Val Thr His Leu Met Gly Leu Phe Glu Pro Ala Asp Met Lys Tyr Asn
            355             360             365

Val Gln Gln Asp His Thr Lys Asp Pro Thr Leu Ala Glu Met Thr Glu
    370             375             380

Ala Ala Leu Gln Val Leu Ser Arg Asn Pro Arg Gly Phe Tyr Leu Phe
385             390             395             400

Val Glu Gly Gly Arg Ile Asp His Gly His His Asp Gly Lys Ala Tyr
            405             410             415

Met Ala Leu Thr Glu Ala Ile Met Phe Asp Asn Ala Ile Ala Lys Ala
            420             425             430

Asn Glu Leu Thr Ser Glu Leu Asp Thr Leu Ile Leu Val Thr Ala Asp
            435             440             445

His Ser His Val Phe Ser Phe Gly Gly Tyr Thr Leu Arg Gly Thr Ser
    450             455             460

Ile Phe Gly Leu Ala Pro Gly Lys Ala Leu Asp Ser Lys Ser Tyr Thr
465             470             475             480

Ser Ile Leu Tyr Gly Asn Gly Pro Gly Tyr Ala Leu Gly Gly Gly Ser
            485             490             495

Arg Pro Asp Val Asn Gly Ser Thr Ser Glu Glu Pro Ser Tyr Arg Gln
            500             505             510

Gln Ala Ala Val Pro Leu Ala Ser Glu Thr His Gly Gly Glu Asp Val
    515             520             525

Ala Val Phe Ala Arg Gly Pro Gln Ala His Leu Val His Gly Val Gln
    530             535             540

Glu Glu Thr Phe Val Ala His Ile Met Ala Phe Ala Gly Cys Val Glu
545             550             555             560

Pro Tyr Thr Asp Cys Asn Leu Pro Ala Pro Ala Thr Ala Thr Ser Ile
            565             570             575

Pro Asp
```

METHOD OF EVALUATING QUALITY OF DEPHOSPHORYLATION REAGENT AND METHOD OF DETECTING TARGET NUCLEIC ACID

TECHNICAL FIELD

This disclosure relates to a method of evaluating a quality of a dephosphorylation reagent containing an alkaline phosphatase, and a method of detecting a target nucleic acid by using a dephosphorylation reagent that has been evaluated as having a high quality by the evaluation method.

BACKGROUND

An alkaline phosphatase has a catalyst function that hydrolyzes phosphoric monoesters, and has been widely used in methods to measure the amount of biological substances such as proteins and nucleic acids (e.g., the immunostaining method, ELISA, the nucleic acid microarray method and the like). For example, in the research field of genetic engineering, for pretreatment of labeling of nucleic acids such as DNA and RNA and prevention of self-ligation of vectors, dephosphorylation of the 5' end and/or the 3' end of a nucleic acid with an alkaline phosphatase has been performed.

As an industrial production method of an alkaline phosphatase, a production method in which bovine small intestine or large intestine is mainly used as a raw material has been widely adopted since the specific activity of the produced alkaline phosphatase is high. The specific activity of an alkaline phosphatase is generally evaluated by measuring the absorbance at 405 nm derived from p-nitrophenol produced when p-nitrophenylphosphate is decomposed.

The quality of an alkaline phosphatase has been evaluated based on the alkaline phosphatase specific activity. To obtain an alkaline phosphatase having a higher specific activity than that of an alkaline phosphatase derived from bovine intestine, an alkaline phosphatase having a high specific activity has been isolated in a purification process or has been produced by using recombinant *Escherichia coli* obtained by a genetic engineering method.

JP H10-262674 A discloses a method of producing an alkaline phosphatase having a high specific activity by using recombinant *Escherichia coli* into which an alkaline phosphatase-encoding gene derived from the genus *Bacillus badius* has been introduced. WO 2012/115023 discloses a method of producing an alkaline phosphatase having a high specific activity and heat resistance by using recombinant *Escherichia coli* into which an alkaline phosphatase-encoding gene derived from the genus *Shewanella* has been introduced.

A dephosphorylation reagent containing an alkaline phosphatase (e.g., a commercially available alkaline phosphatase product) is a composition containing other components in addition to the alkaline phosphatase. The quality of a dephosphorylation reagent containing an alkaline phosphatase is evaluated based on the alkaline phosphatase specific activity.

However, we found that, even if labeled nucleic acids prepared by using dephosphorylation reagents having almost the same alkaline phosphatase specific activity (labeled nucleic acids obtained by dephosphorylating the 5' ends and/or the 3' ends of nucleic acids with the dephosphorylation reagents, and then binding labeling substances to the 5' ends and/or the 3' ends of the dephosphorylated nucleic acids) are used for a nucleic acid detection method, a great difference in the detection sensitivity between the labeled nucleic acids may occur in the nucleic acid detection method. In other words, we found that a quality of a dephosphorylation reagent containing an alkaline phosphatase cannot be evaluated correctly by using the alkaline phosphatase specific activity as an index.

Thus, it could be helpful to provide a method of evaluating a quality of a dephosphorylation reagent containing an alkaline phosphatase, and a method of detecting a target nucleic acid by using a dephosphorylation reagent that has been evaluated as having a high quality by the evaluation method.

The Applicant hereby incorporates by reference the sequence listing contained in the ASCII text file titled SequenceListing.txt, created Mar. 22, 2021 and having 6.72 KB of data.

SUMMARY

We found that at least any one of the following impurities can coexist in a dephosphorylation reagent containing an alkaline phosphatase (e.g., a commercially available alkaline phosphatase product):

a peptide fragment group (A1) composed of two or more peptide fragments, wherein each of the two or more peptide fragments consists of 5 to 50 consecutive amino acid residues selected from positions 71 to 130 of the amino acid sequence set forth in SEQ ID NO: 10 (which corresponds to an amino acid sequence of a bovine-derived alkaline phosphatase);

a peptide fragment group (A2) composed of two or more peptide fragments, wherein each of the two or more peptide fragments consists of 5 to 50 consecutive amino acid residues selected from positions 71 to 130 of the amino acid sequence set forth in SEQ ID NO: 10 and contains positions 86 to 90 of the amino acid sequence set forth in SEQ ID NO: 10;

a peptide fragment group (A3) composed of two or more peptide fragments, wherein each of the two or more peptide fragments consists of 13 to 50 consecutive amino acid residues selected from positions 71 to 130 of the amino acid sequence set forth in SEQ ID NO: 10 and contains positions 93 to 105 of the amino acid sequence set forth in SEQ ID NO: 10;

a peptide fragment group (B1) composed of one or more peptide fragments, wherein each of the one or more peptide fragments consists of 5 to 20 consecutive amino acid residues selected from positions 161 to 200 of the amino acid sequence set forth in SEQ ID NO: 10;

a peptide fragment group (B2) composed of one or more peptide fragments, wherein each of the one or more peptide fragments consists of 11 to 20 consecutive amino acid residues selected from positions 161 to 200 of the amino acid sequence set forth in SEQ ID NO: 10 and contains positions 177 to 187 of the amino acid sequence set forth in SEQ ID NO: 10;

a peptide fragment group (C1) composed of one or more peptide fragments, wherein each of the one or more peptide fragments consists of 5 to 20 consecutive amino acid residues selected from positions 451 to 490 of the amino acid sequence set forth in SEQ ID NO: 10;

a peptide fragment group (C2) composed of one or more peptide fragments, wherein each of the one or more peptide fragments consists of 9 to 20 consecutive amino acid residues selected from positions 451 to 490 of the amino acid sequence set forth in SEQ ID NO: 10 and contains positions 469 to 477 of the amino acid sequence set forth in SEQ ID NO: 10;

a peptide fragment group (D1) composed of two or more peptide fragments, wherein each of the two or more peptide fragments consists of 5 to 50 consecutive amino acid residues selected from positions 501 to 578 of the amino acid sequence set forth in SEQ ID NO: 10;

a peptide fragment group (D2) composed of two or more peptide fragments, wherein each of the two or more peptide fragments consists of 13 to 50 consecutive amino acid residues selected from positions 501 to 578 of the amino acid sequence set forth in SEQ ID NO: 10 and contains positions 516 to 528 of the amino acid sequence set forth in SEQ ID NO: 10;

a peptide fragment group (D3) composed of two or more peptide fragments, wherein each of the two or more peptide fragments consists of 12 to 50 consecutive amino acid residues selected from positions 501 to 578 of the amino acid sequence set forth in SEQ ID NO: 10 and contains positions 534 to 545 of the amino acid sequence set forth in SEQ ID NO: 10;

a first peptide fragment consisting of the amino acid sequence set forth in SEQ ID NO: 1;

a second peptide fragment consisting of the amino acid sequence set forth in SEQ ID NO: 2;

a third peptide fragment consisting of the amino acid sequence set forth in SEQ ID NO: 3;

a fourth peptide fragment consisting of the amino acid sequence set forth in SEQ ID NO: 4;

a fifth peptide fragment consisting of the amino acid sequence set forth in SEQ ID NO: 5;

a sixth peptide fragment consisting of the amino acid sequence set forth in SEQ ID NO: 6;

a seventh peptide fragment consisting of the amino acid sequence set forth in SEQ ID NO: 7;

an eighth peptide fragment consisting of the amino acid sequence set forth in SEQ ID NO: 8; and a ninth peptide fragment consisting of the amino acid sequence set forth in SEQ ID NO: 9.

In addition, we found that, by reducing, in a dephosphorylation reagent which is used to prepare a labeled nucleic acid (a labeled nucleic acid obtained by dephosphorylating the 5' end and/or the 3' end of a nucleic acid with the dephosphorylation reagent, and then binding a labeling substance to the 5' end and/or the 3' end of the dephosphorylated nucleic acid) for a nucleic acid detection method, the content of the peptide fragment group (A1),
the content of the peptide fragment group (A2),
the content of the peptide fragment group (A3),
the content of the peptide fragment group (B1),
the content of the peptide fragment group (B2),
the content of the peptide fragment group (C1),
the content of the peptide fragment group (C2),
the content of the peptide fragment group (D1),
the content of the peptide fragment group (D2),
the content of the peptide fragment group (D3),
the content of the second peptide fragment (preferably, the content of the second peptide fragment, and the content(s) of one or two peptide fragments selected from the first and third peptide fragments),
the content of the fourth peptide fragment,
the content of the fifth peptide fragment,
the content of the seventh peptide fragment (preferably, the content of the seventh peptide fragment, and the content(s) of one, two or three peptide fragments selected from the sixth, eighth and ninth peptide fragments),
the content of the eighth peptide fragment (preferably, the content of the eighth peptide fragment, and the content(s) of one, two or three peptide fragments selected from the sixth, seventh and ninth peptide fragments),
the content of the ninth peptide fragment (preferably, the content of the ninth peptide fragment, and the content(s) of one, two or three peptide fragments selected from the sixth, seventh and eighth peptide fragments), or
the contents of the second, fourth, fifth, seventh, eighth and ninth peptide fragments (preferably, the contents of the second, fourth, fifth, seventh, eighth and ninth peptide fragments, and the content(s) of one, two or three peptide fragments selected from the group consisting of the first, third and sixth peptide fragments), it is possible to improve the detection sensitivity of the labeled nucleic acid in the nucleic acid detection method.

We thus provide:

[1] A method of evaluating a quality of a dephosphorylation reagent, the method including the steps of:
(1-1) providing a dephosphorylation reagent containing an alkaline phosphatase and a peptide fragment derived from the alkaline phosphatase; and
(1-2) evaluating the dephosphorylation reagent as having a high quality if a content ratio of the peptide fragment to the alkaline phosphatase is a predetermined reference value or less.

[2] The method according to [1], wherein the dephosphorylation reagent has an alkaline phosphatase specific activity of 2,000 U/mg or more.

[3] The method according to [1] or [2], wherein the alkaline phosphatase is selected from the following (a) and (b):
(a) an alkaline phosphatase containing a protein molecule consisting of the amino acid sequence set forth in SEQ ID NO: 10; and
(b) an alkaline phosphatase containing a protein molecule consisting of an amino acid sequence that has 70% or more sequence identity to the amino acid sequence set forth in SEQ ID NO: 10.

[4] The method according to any one of [1] to [3], wherein:
the dephosphorylation reagent contains a peptide fragment group (A1) composed of two or more peptide fragments, wherein each of the two or more peptide fragments consists of 5 to 50 consecutive amino acid residues selected from positions 71 to 130 of the amino acid sequence set forth in SEQ ID NO: 10; and
the dephosphorylation reagent is evaluated as having a high quality if a content ratio of the peptide fragment group (A1) to the alkaline phosphatase satisfies formula (A1):

$$(X_{A1}/Y) \times 100 \leq 5.0000 \quad (A1),$$

wherein $X_{A1}$ represents a peak area value of the peptide fragment group (A1) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[5] The method according to [4], wherein the peptide fragment group (A1) contains one, two or three peptide fragments selected from the group consisting of a first peptide fragment consisting of the amino acid sequence set forth in SEQ ID NO: 1, a second peptide fragment consisting of the amino acid sequence set forth in SEQ ID NO: 2 and a third peptide fragment consisting of the amino acid sequence set forth in SEQ ID NO: 3.

[6] The method according to [5], wherein:
the peptide fragment group (A1) contains the first peptide fragment; and
the dephosphorylation reagent is evaluated as having a high quality if the content ratio of the peptide fragment group (A1) to the alkaline phosphatase satisfies formula (A1) and a content ratio of the first peptide fragment to the alkaline phosphatase satisfies formula (1):

$$(X_1/Y) \times 100 \leq 1.0000 \tag{1},$$

wherein $X_1$ represents a peak area value of the first peptide fragment calculated by an automatic integration method from an extracted ion chromatogram obtained by an LC-MS/MS analysis of the dephosphorylation reagent, and Y is the same as defined above.

[7] The method according to [5] or [6], wherein:
the peptide fragment group (A1) contains the second peptide fragment; and
the dephosphorylation reagent is evaluated as having a high quality if the content ratio of the peptide fragment group (A1) to the alkaline phosphatase satisfies formula (A1) and a content ratio of the second peptide fragment to the alkaline phosphatase satisfies formula (2):

$$(X_2/Y) \times 100 \leq 0.8000 \tag{2},$$

wherein $X_2$ represents a peak area value of the second peptide fragment calculated by an automatic integration method from an extracted ion chromatogram obtained by an LC-MS/MS analysis of the dephosphorylation reagent, and Y is the same as defined above.

[8] The method according to any one of [5] to [7], wherein:
the peptide fragment group (A1) contains the third peptide fragment; and the dephosphorylation reagent is evaluated as having a high quality if the content ratio of the peptide fragment group (A1) to the alkaline phosphatase satisfies formula (A1) and a content ratio of the third peptide fragment to the alkaline phosphatase satisfies formula (3):

$$(X_3/Y) \times 100 \leq 2.3000 \tag{3},$$

wherein $X_3$ represents a peak area value of the third peptide fragment calculated by an automatic integration method from an extracted ion chromatogram obtained by an LC-MS/MS analysis of the dephosphorylation reagent, and Y is the same as defined above.

[9] The method according to any one of [1] to [3], wherein:
the dephosphorylation reagent contains a peptide fragment group (A2) composed of two or more peptide fragments, wherein each of the two or more peptide fragments consists of 5 to 50 consecutive amino acid residues selected from positions 71 to 130 of the amino acid sequence set forth in SEQ ID NO: 10 and contains positions 86 to 90 of the amino acid sequence set forth in SEQ ID NO: 10; and
the dephosphorylation reagent is evaluated as having a high quality if a content ratio of the peptide fragment group (A2) to the alkaline phosphatase satisfies formula (A2):

$$(X_{A2}/Y) \times 100 \leq 2.4000 \tag{A2},$$

wherein $X_{A2}$ represents a peak area value of the peptide fragment group (A2) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[10] The method according to [9], wherein the peptide fragment group (A2) contains one or two peptide fragments selected from the group consisting of a first peptide fragment consisting of the amino acid sequence set forth in SEQ ID NO: 1 and a second peptide fragment consisting of the amino acid sequence set forth in SEQ ID NO: 2.

[11] The method according to [10], wherein:
the peptide fragment group (A2) contains the first peptide fragment; and
the dephosphorylation reagent is evaluated as having a high quality if the content ratio of the peptide fragment group (A2) to the alkaline phosphatase satisfies formula (A2) and a content ratio of the first peptide fragment to the alkaline phosphatase satisfies formula (1):

$$(X_1/Y) \times 100 \leq 1.0000 \tag{1},$$

wherein $X_1$ represents a peak area value of the first peptide fragment calculated by an automatic integration method from an extracted ion chromatogram obtained by an LC-MS/MS analysis of the dephosphorylation reagent, and Y is the same as defined above.

[12] The method according to [10] or [11], wherein:
the peptide fragment group (A2) contains the second peptide fragment; and
the dephosphorylation reagent is evaluated as having a high quality if the content ratio of the peptide fragment group (A2) to the alkaline phosphatase satisfies formula (A2) and a content ratio of the second peptide fragment to the alkaline phosphatase satisfies formula (2):

$$(X_2/Y) \times 100 \leq 0.8000 \tag{2},$$

wherein $X_2$ represents a peak area value of the second peptide fragment calculated by an automatic integration method from an extracted ion chromatogram obtained by an LC-MS/MS analysis of the dephosphorylation reagent, and Y is the same as defined above.

[13] The method according to any one of [1] to [3], wherein:
the dephosphorylation reagent contains a peptide fragment group (A3) composed of two or more peptide fragments, wherein each of the two or more peptide fragments consists of 13 to 50 consecutive amino acid residues selected from positions 71 to 130 of the amino acid sequence set forth in SEQ ID NO: 10 and contains positions 93 to 105 of the amino acid sequence set forth in SEQ ID NO: 10; and
the dephosphorylation reagent is evaluated as having a high quality if a content ratio of the peptide fragment group (A3) to the alkaline phosphatase satisfies formula (A3):

$$(X_{A3}/Y) \times 100 \leq 4.5000 \tag{A3},$$

wherein $X_{A3}$ represents a peak area value of the peptide fragment group (A3) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[14] The method according to [13], wherein the peptide fragment group (A3) contains one or two peptide fragments selected from the group consisting of a first peptide fragment consisting of the amino acid sequence set forth in SEQ ID NO: 1 and a third peptide fragment consisting of the amino acid sequence set forth in SEQ ID NO: 3.

[15] The method according to [14], wherein:
the peptide fragment group (A3) contains the first peptide fragment; and
the dephosphorylation reagent is evaluated as having a high quality if the content ratio of the peptide fragment group (A3) to the alkaline phosphatase satisfies formula (A3) and a content ratio of the first peptide fragment to the alkaline phosphatase satisfies formula (1):

$$(X_1/Y) \times 100 \leq 1.0000 \qquad (1),$$

wherein $X_1$ represents a peak area value of the first peptide fragment calculated by an automatic integration method from an extracted ion chromatogram obtained by an LC-MS/MS analysis of the dephosphorylation reagent, and Y is the same as defined above.

[16] The method according to [14] or [15], wherein:
the peptide fragment group (A3) contains the third peptide fragment; and
the dephosphorylation reagent is evaluated as having a high quality if the content ratio of the peptide fragment group (A3) to the alkaline phosphatase satisfies formula (A3) and a content ratio of the third peptide fragment to the alkaline phosphatase satisfies formula (3):

$$(X_3/Y) \times 100 \leq 2.3000 \qquad (3),$$

wherein $X_3$ represents a peak area value of the third peptide fragment calculated by an automatic integration method from an extracted ion chromatogram obtained by an LC-MS/MS analysis of the dephosphorylation reagent, and Y is the same as defined above.

[17] The method according to any one of [1] to [3], wherein:
the dephosphorylation reagent contains a second peptide fragment consisting of the amino acid sequence set forth in SEQ ID NO: 2; and
the dephosphorylation reagent is evaluated as having a high quality if a content ratio of the second peptide fragment to the alkaline phosphatase satisfies formula (2):

$$(X_2/Y) \times 100 \leq 0.8000 \qquad (2),$$

wherein $X_2$ represents a peak area value of the second peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[18] The method according to [17], wherein:
the dephosphorylation reagent further contains a first peptide fragment consisting of the amino acid sequence set forth in SEQ ID NO: 1; and
the dephosphorylation reagent is evaluated as having a high quality if the content ratio of the second peptide fragment to the alkaline phosphatase satisfies formula (2) and a content ratio of the first peptide fragment to the alkaline phosphatase satisfies formula (1):

$$(X_1/Y) \times 100 \leq 1.0000 \qquad (1),$$

wherein $X_1$ represents a peak area value of the first peptide fragment calculated by an automatic integration method from an extracted ion chromatogram obtained by an LC-MS/MS analysis of the dephosphorylation reagent, and Y is the same as defined above.

[19] The method according to [17] or [18], wherein:
the dephosphorylation reagent further contains a third peptide fragment consisting of the amino acid sequence set forth in SEQ ID NO: 3; and
the content ratio of the second peptide fragment to the alkaline phosphatase satisfies formula (2) and a content ratio of the third peptide fragment to the alkaline phosphatase satisfies formula (3):

$$(X_3/Y) \times 100 \leq 2.3000 \qquad (3),$$

wherein $X_3$ represents a peak area value of the third peptide fragment calculated by an automatic integration method from an extracted ion chromatogram obtained by an LC-MS/MS analysis of the dephosphorylation reagent, and Y is the same as defined above.

[20] The method according to any one of [4] to [19], wherein the alkaline phosphatase is selected from the following (a) and (b1):
(a) an alkaline phosphatase containing a protein molecule consisting of the amino acid sequence set forth in SEQ ID NO: 10; and
(b1) an alkaline phosphatase containing a protein molecule consisting of an amino acid sequence that has 70% or more sequence identity to the amino acid sequence set forth in SEQ ID NO: 10 and contains positions 71 to 130 of the amino acid sequence set forth in SEQ ID NO: 10.

[21] The method according to any one of [1] to [3], wherein:
the dephosphorylation reagent contains a peptide fragment group (B1) composed of one or more peptide fragments, wherein each of the one or more peptide fragments consists of 5 to 20 consecutive amino acid residues selected from positions 161 to 200 of the amino acid sequence set forth in SEQ ID NO: 10; and
the dephosphorylation reagent is evaluated as having a high quality if a content ratio of the peptide fragment group (B1) to the alkaline phosphatase satisfies formula (B1):

$$(X_{B1}/Y) \times 100 \leq 0.6000 \qquad (B1),$$

wherein $X_{B1}$ represents a peak area value of the peptide fragment group (B1) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[22] The method according to [21], wherein the peptide fragment group (B1) contains a fourth peptide fragment consisting of the amino acid sequence set forth in SEQ ID NO: 4.

[23] The method according to [22], wherein the dephosphorylation reagent is evaluated as having a high quality if the content ratio of the peptide fragment group (B1) to the alkaline phosphatase satisfies formula (B1) and a content ratio of the fourth peptide fragment to the alkaline phosphatase satisfies formula (4):

$$(X_4/Y) \times 100 \leq 0.6000 \qquad (4),$$

wherein $X_4$ represents a peak area value of the fourth peptide fragment calculated by an automatic integration method from an extracted ion chromatogram obtained by an LC-MS/MS analysis of the dephosphorylation reagent, and Y is the same as defined above.

[24] The method according to any one of [1] to [3], wherein:

the dephosphorylation reagent contains a peptide fragment group (B2) composed of one or more peptide fragments, each of the one or more peptide fragments consists of 11 to 20 consecutive amino acid residues selected from positions 161 to 200 of the amino acid sequence set forth in SEQ ID NO: 10 and contains positions 177 to 187 of the amino acid sequence set forth in SEQ ID NO: 10; and the dephosphorylation reagent is evaluated as having a high quality if a content ratio of the peptide fragment group (B2) to the alkaline phosphatase satisfies formula (B2):

$$(X_{B2}/Y) \times 100 \leq 0.6000 \tag{B2},$$

wherein $X_{B2}$ represents a peak area value of the peptide fragment group (B2) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[25] The method according to [24], wherein the peptide fragment group (B2) contains a fourth peptide fragment consisting of the amino acid sequence set forth in SEQ ID NO: 4.

[26] The method according to [25], wherein the dephosphorylation reagent is evaluated as having a high quality if the content ratio of the peptide fragment group (B2) to the alkaline phosphatase satisfies formula (B2) and a content ratio of the fourth peptide fragment to the alkaline phosphatase satisfies formula (4):

$$(X_4/Y) \times 100 \leq 0.6000 \tag{4},$$

wherein $X_4$ represents a peak area value of the fourth peptide fragment calculated by an automatic integration method from an extracted ion chromatogram obtained by an LC-MS/MS analysis of the dephosphorylation reagent, and Y is the same as defined above.

[27] The method according to any one of [1] to [3], wherein:

the dephosphorylation reagent contains a fourth peptide fragment consisting of the amino acid sequence set forth in SEQ ID NO: 4; and the dephosphorylation reagent is evaluated as having a high quality if a content ratio of the fourth peptide fragment to the alkaline phosphatase satisfies formula (4):

$$(X_4/Y) \times 100 \leq 0.6000 \tag{4},$$

wherein $X_4$ represents a peak area value of the fourth peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[28] The method according to any one of [21] to [27], wherein the alkaline phosphatase is selected from the following (a) and (b2):

(a) an alkaline phosphatase containing a protein molecule consisting of the amino acid sequence set forth in SEQ ID NO: 10; and (b2) an alkaline phosphatase containing a protein molecule consisting of an amino acid sequence that has 70% or more sequence identity to the amino acid sequence set forth in SEQ ID NO: 10 and contains positions 161 to 200 of the amino acid sequence set forth in SEQ ID NO: 10.

[29] The method according to any one of [1] to [3], wherein:

the dephosphorylation reagent contains a peptide fragment group (C1) composed of one or more peptide fragments, wherein each of the one or more peptide fragments consists of 5 to 20 consecutive amino acid residues selected from positions 451 to 490 of the amino acid sequence set forth in SEQ ID NO: 10; and the dephosphorylation reagent is evaluated as having a high quality if a content ratio of the peptide fragment group (C1) to the alkaline phosphatase satisfies formula (C1):

$$(X_{C1}/Y) \times 100 \leq 0.1800 \tag{C1},$$

wherein $X_{C1}$ represents a peak area value of the peptide fragment group (C1) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[30] The method according to [29], wherein the peptide fragment group (C1) contains a fifth peptide fragment consisting of the amino acid sequence set forth in SEQ ID NO: 5.

[31] The method according to [30], wherein the dephosphorylation reagent is evaluated as having a high quality if the content ratio of the peptide fragment group (C1) to the alkaline phosphatase satisfies formula (C1) and a content ratio of the fifth peptide fragment to the alkaline phosphatase satisfies formula (5):

$$(X_5/Y) \times 100 \leq 0.1800 \tag{5},$$

wherein $X_5$ represents a peak area value of the fifth peptide fragment calculated by an automatic integration method from an extracted ion chromatogram obtained by an LC-MS/MS analysis of the dephosphorylation reagent, and Y is the same as defined above.

[32] The method according to any one of [1] to [3], wherein:

the dephosphorylation reagent contains a peptide fragment group (C2) composed of one or more peptide fragments, wherein each of the one or more peptide fragments consists of 9 to 20 consecutive amino acid residues selected from positions 451 to 490 of the amino acid sequence set forth in SEQ ID NO: 10 and contains positions 469 to 477 of the amino acid sequence set forth in SEQ ID NO: 10; and the dephosphorylation reagent is evaluated as having a high quality if a content ratio of the peptide fragment group (C2) to the alkaline phosphatase satisfies formula (C2):

$$(X_{C2}/Y) \times 100 \leq 0.1800 \tag{C2},$$

wherein $X_{C2}$ represents a peak area value of the peptide fragment group (C2) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[33] The method according to [32], wherein the peptide fragment group (C2) contains a fifth peptide fragment consisting of the amino acid sequence set forth in SEQ ID NO: 5.

[34] The method according to [33], wherein the dephosphorylation reagent is evaluated as having a high quality if the content ratio of the peptide fragment group (C2) to the alkaline phosphatase satisfies formula (C2) and a content ratio of the fifth peptide fragment to the alkaline phosphatase satisfies formula (5):

$$(X_5/Y) \times 100 \leq 0.1800 \quad (5),$$

wherein $X_5$ represents a peak area value of the fifth peptide fragment calculated by an automatic integration method from an extracted ion chromatogram obtained by an LC-MS/MS analysis of the dephosphorylation reagent, and Y is the same as defined above.

[35] The method according to any one of [1] to [3], wherein:
the dephosphorylation reagent contains a fifth peptide fragment consisting of the amino acid sequence set forth in SEQ ID NO: 5; and
the dephosphorylation reagent is evaluated as having a high quality if a content ratio of the fifth peptide fragment to the alkaline phosphatase satisfies formula (5):

$$(X_5/Y) \times 100 \leq 0.1800 \quad (5),$$

wherein $X_5$ represents a peak area value of the fifth peptide fragment calculated by an automatic integration method from an extracted ion chromatogram obtained by an LC-MS/MS analysis of the dephosphorylation reagent, and Y is the same as defined above.

[36] The method according to any one of [29] to [35], wherein the alkaline phosphatase is selected from the following (a) and (b3):
(a) an alkaline phosphatase containing a protein molecule consisting of the amino acid sequence set forth in SEQ ID NO: 10; and
(b3) an alkaline phosphatase containing a protein molecule consisting of an amino acid sequence that has 70% or more sequence identity to the amino acid sequence set forth in SEQ ID NO: 10 and contains positions 451 to 490 of the amino acid sequence set forth in SEQ ID NO: 10.

[37] The method according to any one of [1] to [3], wherein:
the dephosphorylation reagent contains a peptide fragment group (D1) composed of two or more peptide fragments, wherein each of the two or more peptide fragments consists of 5 to 50 consecutive amino acid residues selected from positions 501 to 578 of the amino acid sequence set forth in SEQ ID NO: 10; and
the dephosphorylation reagent is evaluated as having a high quality if a content ratio of the peptide fragment group (D1) to the alkaline phosphatase satisfies formula (D1):

$$(X_{D1}/Y) \times 100 \leq 4.4000 \quad (D1),$$

wherein $X_{D1}$ represents a peak area value of the peptide fragment group (D1) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[38] The method according to [37], wherein the peptide fragment group (D1) contains one, two, three or four peptide fragments selected from the group consisting of a sixth peptide fragment consisting of the amino acid sequence set forth in SEQ ID NO: 6, a seventh peptide fragment consisting of the amino acid sequence set forth in SEQ ID NO: 7, an eighth peptide fragment consisting of the amino acid sequence set forth in SEQ ID NO: 8 and a ninth peptide fragment consisting of the amino acid sequence set forth in SEQ ID NO: 9.

[39] The method according to [38], wherein:
the peptide fragment group (D1) contains the sixth peptide fragment; and
the dephosphorylation reagent is evaluated as having a high quality if the content ratio of the peptide fragment group (D1) to the alkaline phosphatase satisfies formula (D1) and a content ratio of the sixth peptide fragment to the alkaline phosphatase satisfies formula (6):

$$(X_6/Y) \times 100 \leq 1.0000 \quad (6),$$

wherein $X_6$ represents a peak area value of the sixth peptide fragment calculated by an automatic integration method from an extracted ion chromatogram obtained by an LC-MS/MS analysis of the dephosphorylation reagent, and Y is the same as defined above.

[40] The method according to [38] or [39], wherein:
the peptide fragment group (D1) contains the seventh peptide fragment; and
the dephosphorylation reagent is evaluated as having a high quality if the content ratio of the peptide fragment group (D1) to the alkaline phosphatase satisfies formula (D1) and a content ratio of the seventh peptide fragment to the alkaline phosphatase satisfies formula (7):

$$(X_7/Y) \times 100 \leq 1.6000 \quad (7),$$

wherein $X_7$ represents a peak area value of the seventh peptide fragment calculated by an automatic integration method from an extracted ion chromatogram obtained by an LC-MS/MS analysis of the dephosphorylation reagent, and Y is the same as defined above.

[41] The method according to any one of [38] to [40], wherein:
the peptide fragment group (D1) contains the eighth peptide fragment; and
the dephosphorylation reagent is evaluated as having a high quality if the content ratio of the peptide fragment group (D1) to the alkaline phosphatase satisfies formula (D1) and a content ratio of the eighth peptide fragment to the alkaline phosphatase satisfies formula (8):

$$(X_8/Y) \times 100 \leq 0.2000 \quad (8),$$

wherein $X_8$ represents a peak area value of the eighth peptide fragment calculated by an automatic integration method from an extracted ion chromatogram obtained by an LC-MS/MS analysis of the dephosphorylation reagent, and Y is the same as defined above.

[42] The method according to any one of [38] to [41], wherein:
the peptide fragment group (D1) contains the ninth peptide fragment; and
the dephosphorylation reagent is evaluated as having a high quality if the content ratio of the peptide fragment group (D1) to the alkaline phosphatase satisfies formula (D1) and a content ratio of the ninth peptide fragment to the alkaline phosphatase satisfies formula (9):

$$(X_9/Y) \times 100 \leq 0.3500 \qquad (9),$$

wherein $X_9$ represents a peak area value of the ninth peptide fragment calculated by an automatic integration method from an extracted ion chromatogram obtained by an LC-MS/MS analysis of the dephosphorylation reagent, and Y is the same as defined above.

[43] The method according to any one of [1] to [3], wherein:
the dephosphorylation reagent contains a peptide fragment group (D2) composed of two or more peptide fragments, wherein each of the two or more peptide fragments consists of 13 to 50 consecutive amino acid residues selected from positions 501 to 578 of the amino acid sequence set forth in SEQ ID NO: 10 and contains positions 516 to 528 of the amino acid sequence set forth in SEQ ID NO: 10; and
the dephosphorylation reagent is evaluated as having a high quality if a content ratio of the peptide fragment group (D2) to the alkaline phosphatase satisfies formula (D2):

$$(X_{D2}/Y) \times 100 \leq 3.4000 \qquad (D2),$$

wherein $X_{D2}$ represents a peak area value of the peptide fragment group (D2) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[44] The method according to [43], wherein the peptide fragment group (D2) contains one or two peptide fragments selected from the group consisting of a sixth peptide fragment consisting of the amino acid sequence set forth in SEQ ID NO: 6 and a seventh peptide fragment consisting of the amino acid sequence set forth in SEQ ID NO: 7.

[45] The method according to [44], wherein:
the peptide fragment group (D2) contains the sixth peptide fragment; and the dephosphorylation reagent is evaluated as having a high quality if the content ratio of the peptide fragment group (D2) to the alkaline phosphatase satisfies formula (D2) and a content ratio of the sixth peptide fragment to the alkaline phosphatase satisfies formula (6):

$$(X_6/Y) \times 100 \leq 1.0000 \qquad (6),$$

wherein $X_6$ represents a peak area value of the sixth peptide fragment calculated by an automatic integration method from an extracted ion chromatogram obtained by an LC-MS/MS analysis of the dephosphorylation reagent, and Y is the same as defined above.

[46] The method according to [44] or [45], wherein:
the peptide fragment group (D2) contains the seventh peptide fragment; and the dephosphorylation reagent is evaluated as having a high quality if the content ratio of the peptide fragment group (D2) to the alkaline phosphatase satisfies formula (D2) and a content ratio of the seventh peptide fragment to the alkaline phosphatase satisfies formula (7):

$$(X_7/Y) \times 100 \leq 1.6000 \qquad (7),$$

wherein $X_7$ represents a peak area value of the seventh peptide fragment calculated by an automatic integration method from an extracted ion chromatogram obtained by an LC-MS/MS analysis of the dephosphorylation reagent, and Y is the same as defined above.

[47] The method according to any one of [1] to [3], wherein:
the dephosphorylation reagent contains a peptide fragment group (D3) composed of two or more peptide fragments, wherein each of the two or more peptide fragments consists of 12 to 50 consecutive amino acid residues selected from positions 501 to 578 of the amino acid sequence set forth in SEQ ID NO: 10 and contains positions 534 to 545 of the amino acid sequence set forth in SEQ ID NO: 10; and
the dephosphorylation reagent is evaluated as having a high quality if a content ratio of the peptide fragment group (D3) to the alkaline phosphatase satisfies formula (D3):

$$(X_{D3}/Y) \times 100 \leq 1.0000 \qquad (D3),$$

wherein $X_{D3}$ represents a peak area value of the peptide fragment group (D3) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[48] The method according to [47], wherein the peptide fragment group (D3) contains one or two peptide fragments selected from the group consisting of an eighth peptide fragment consisting of the amino acid sequence set forth in SEQ ID NO: 8 and a ninth peptide fragment consisting of the amino acid sequence set forth in SEQ ID NO: 9.

[49] The method according to [48], wherein:
the peptide fragment group (D3) contains the eighth peptide fragment; and the dephosphorylation reagent is evaluated as having a high quality if the content ratio of the peptide fragment group (D3) to the alkaline phosphatase satisfies formula (D3) and a content ratio of the eighth peptide fragment to the alkaline phosphatase satisfies formula (8):

$$(X_8/Y) \times 100 \leq 0.2000 \qquad (8),$$

wherein $X_8$ represents a peak area value of the eighth peptide fragment calculated by an automatic integration method from an extracted ion chromatogram obtained by an LC-MS/MS analysis of the dephosphorylation reagent, and Y is the same as defined above.

[50] The method according to [48] or [49], wherein:
the peptide fragment group (D3) contains the ninth peptide fragment; and the dephosphorylation reagent is evaluated as having a high quality if the content ratio of the peptide fragment group (D3) to the alkaline phosphatase satisfies formula (D3) and a content ratio of the ninth peptide fragment to the alkaline phosphatase satisfies formula (9):

$$(X_9/Y) \times 100 \leq 0.3500 \qquad (9),$$

wherein $X_9$ represents a peak area value of the ninth peptide fragment calculated by an automatic integration method from an extracted ion chromatogram obtained by an LC-MS/MS analysis of the dephosphorylation reagent, and Y is the same as defined above.

[51] The method according to any one of [1] to [3], wherein:
the dephosphorylation reagent contains a seventh peptide fragment consisting of the amino acid sequence set forth in SEQ ID NO: 7; and
the dephosphorylation reagent is evaluated as having a high quality if a content ratio of the seventh peptide fragment to the alkaline phosphatase satisfies formula (7):

$$(X_7/Y) \times 100 \leq 1.6000 \tag{7},$$

wherein $X_7$ represents a peak area value of the seventh peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[52] The method according to [51], wherein:
the dephosphorylation reagent further contains a sixth peptide fragment consisting of the amino acid sequence set forth in SEQ ID NO: 6; and
the dephosphorylation reagent is evaluated as having a high quality if the content ratio of the seventh peptide fragment to the alkaline phosphatase satisfies formula (7) and a content ratio of the sixth peptide fragment to the alkaline phosphatase satisfies formula (6):

$$(X_6/Y) \times 100 \leq 1.0000 \tag{6},$$

wherein $X_6$ represents a peak area value of the sixth peptide fragment calculated by an automatic integration method from an extracted ion chromatogram obtained by an LC-MS/MS analysis of the dephosphorylation reagent, and Y is the same as defined above.

[53] The method according to [51] or [52], wherein:
the dephosphorylation reagent further contains an eighth peptide fragment consisting of the amino acid sequence set forth in SEQ ID NO: 8; and
the dephosphorylation reagent is evaluated as having a high quality if the content ratio of the seventh peptide fragment to the alkaline phosphatase satisfies formula (7) and a content ratio of the eighth peptide fragment to the alkaline phosphatase satisfies formula (8):

$$(X_8/Y) \times 100 \leq 0.2000 \tag{8},$$

wherein $X_8$ represents a peak area value of the eighth peptide fragment calculated by an automatic integration method from an extracted ion chromatogram obtained by an LC-MS/MS analysis of the dephosphorylation reagent, and Y is the same as defined above.

[54] The method according to any one of [51] to [53], wherein:
the dephosphorylation reagent further contains a ninth peptide fragment consisting of the amino acid sequence set forth in SEQ ID NO: 9; and
the dephosphorylation reagent is evaluated as having a high quality if the content ratio of the seventh peptide fragment to the alkaline phosphatase satisfies formula (7) and a content ratio of the ninth peptide fragment to the alkaline phosphatase satisfies formula (9):

$$(X_9/Y) \times 100 \leq 0.3500 \tag{9},$$

wherein $X_9$ represents a peak area value of the ninth peptide fragment calculated by an automatic integration method from an extracted ion chromatogram obtained by an LC-MS/MS analysis of the dephosphorylation reagent, and Y is the same as defined above.

[55] The method according to any one of [1] to [3], wherein:
the dephosphorylation reagent contains an eighth peptide fragment consisting of the amino acid sequence set forth in SEQ ID NO: 8; and
the dephosphorylation reagent is evaluated as having a high quality if a content ratio of the eighth peptide fragment to the alkaline phosphatase satisfies formula (8):

$$(X_8/Y) \times 100 \leq 0.2000 \tag{8},$$

wherein $X_8$ represents a peak area value of the eighth peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[56] The method according to [55], wherein:
the dephosphorylation reagent further contains a sixth peptide fragment consisting of the amino acid sequence set forth in SEQ ID NO: 6; and
the dephosphorylation reagent is evaluated as having a high quality if the content ratio of the eighth peptide fragment to the alkaline phosphatase satisfies formula (8) and a content ratio of the sixth peptide fragment to the alkaline phosphatase satisfies formula (6):

$$(X_6/Y) \times 100 \leq 1.0000 \tag{6},$$

wherein $X_6$ represents a peak area value of the sixth peptide fragment calculated by an automatic integration method from an extracted ion chromatogram obtained by an LC-MS/MS analysis of the dephosphorylation reagent, and Y is the same as defined above.

[57] The method according to [55] or [56], wherein:
the dephosphorylation reagent further contains a ninth peptide fragment consisting of the amino acid sequence set forth in SEQ ID NO: 9; and
the dephosphorylation reagent is evaluated as having a high quality if the content ratio of the eighth peptide fragment to the alkaline phosphatase satisfies formula (8) and a content ratio of the ninth peptide fragment to the alkaline phosphatase satisfies formula (9):

$$(X_9/Y) \times 100 \leq 0.3500 \tag{9},$$

wherein $X_9$ represents a peak area value of the ninth peptide fragment calculated by an automatic integration method from an extracted ion chromatogram obtained by an LC-MS/MS analysis of the dephosphorylation reagent, and Y is the same as defined above.

[58] The method according to any one of [1] to [3], wherein:
the dephosphorylation reagent contains a ninth peptide fragment consisting of the amino acid sequence set forth in SEQ ID NO: 9; and
the dephosphorylation reagent is evaluated as having a high quality if a content ratio of the ninth peptide fragment to the alkaline phosphatase satisfies formula (9):

$$(X_9/Y) \times 100 \leq 0.3500 \tag{9},$$

wherein $X_9$ represents a peak area value of the ninth peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent.

[59] The method according to [58], wherein:
the dephosphorylation reagent further contains a sixth peptide fragment consisting of the amino acid sequence set forth in SEQ ID NO: 6; and
the dephosphorylation reagent is evaluated as having a high quality if the content ratio of the ninth peptide fragment to the alkaline phosphatase satisfies formula (9) and a content ratio of the sixth peptide fragment to the alkaline phosphatase satisfies formula (6):

$$(X_6/Y) \times 100 \leq 1.0000 \qquad (6),$$

wherein $X_6$ represents a peak area value of the sixth peptide fragment calculated by an automatic integration method from an extracted ion chromatogram obtained by an LC-MS/MS analysis of the dephosphorylation reagent, and Y is the same as defined above.

[60] The method according to any one of [37] to [59], wherein the alkaline phosphatase is selected from the following (a) and (b4):
(a) an alkaline phosphatase containing a protein molecule consisting of the amino acid sequence set forth in SEQ ID NO: 10; and
(b4) an alkaline phosphatase containing a protein molecule consisting of an amino acid sequence that has 70% or more sequence identity to the amino acid sequence set forth in SEQ ID NO: 10 and contains positions 501 to 578 of the amino acid sequence set forth in SEQ ID NO: 10.

[61] The method according to any one of [1] to [3], wherein:
the dephosphorylation reagent contains
a second peptide fragment consisting of the amino acid sequence set forth in SEQ ID NO: 2,
a fourth peptide fragment consisting of the amino acid sequence set forth in SEQ ID NO: 4,
a fifth peptide fragment consisting of the amino acid sequence set forth in SEQ ID NO: 5,
a seventh peptide fragment consisting of the amino acid sequence set forth in SEQ ID NO: 7,
an eighth peptide fragment consisting of the amino acid sequence set forth in SEQ ID NO: 8, and
a ninth peptide fragment consisting of the amino acid sequence set forth in SEQ ID NO: 9; and
the dephosphorylation reagent is evaluated as having a high quality if content ratios of the second, fourth, fifth, seventh, eighth and ninth peptide fragments to the alkaline phosphatase satisfy formulas (2), (4), (5), (7), (8) and (9), respectively:

$$(X_2/Y) \times 100 \leq 0.8000 \qquad (2),$$

$$(X_4/Y) \times 100 \leq 0.6000 \qquad (4),$$

$$(X_5/Y) \times 100 \leq 0.1800 \qquad (5),$$

$$(X_7/Y) \times 100 \leq 1.6000 \qquad (7),$$

$$(X_8/Y) \times 100 \leq 0.2000 \qquad (8), \text{ and}$$

$$(X_9/Y) \times 100 \leq 0.3500 \qquad (9),$$

wherein $X_2$, $X_4$, $X_5$, $X_7$, $X_8$ and $X_9$ represent peak area values of the second, fourth, fifth, seventh, eighth and ninth peptide fragments calculated by an automatic integration method from an extracted ion chromatogram obtained by an LC-MS/MS analysis of the dephosphorylation reagent, respectively, and Y represents a peak area value of the alkaline phosphatase calculated by an automatic integration method from a chromatogram obtained by an LC-UV analysis of the dephosphorylation reagent.

[62] The method according to [61], wherein:
the dephosphorylation reagent further contains a first peptide fragment consisting of the amino acid sequence set forth in SEQ ID NO: 1; and
the dephosphorylation reagent is evaluated as having a high quality if the content ratios of the second, fourth, fifth, seventh, eighth and ninth peptide fragments to the alkaline phosphatase satisfy formulas (2), (4), (5), (7), (8) and (9), respectively, and a content ratio of the first peptide fragment to the alkaline phosphatase satisfies formula (1):

$$(X_1/Y) \times 100 \leq 1.0000 \qquad (1),$$

wherein $X_1$ represents a peak area value of the first peptide fragment calculated by an automatic integration method from an extracted ion chromatogram obtained by an LC-MS/MS analysis of the dephosphorylation reagent, and Y is the same as defined above.

[63] The method according to [61] or [62], wherein:
the dephosphorylation reagent further contains a third peptide fragment consisting of the amino acid sequence set forth in SEQ ID NO: 3; and
the dephosphorylation reagent is evaluated as having a high quality if the content ratios of the second, fourth, fifth, seventh, eighth and ninth peptide fragments to the alkaline phosphatase satisfy formulas (2), (4), (5), (7), (8) and (9), respectively, and a content ratio of the third peptide fragment to the alkaline phosphatase satisfies formula (3):

$$(X_3/Y) \times 100 \leq 2.3000 \qquad (3),$$

wherein $X_3$ represents a peak area value of the third peptide fragment calculated by an automatic integration method from an extracted ion chromatogram obtained by an LC-MS/MS analysis of the dephosphorylation reagent, and Y is the same as defined above.

[64] The method according to any one of [61] to [63], wherein:
the dephosphorylation reagent further contains a sixth peptide fragment consisting of the amino acid sequence set forth in SEQ ID NO: 6; and
the dephosphorylation reagent is evaluated as having a high quality if the content ratios of the second, fourth, fifth, seventh, eighth and ninth peptide fragments to the alkaline phosphatase satisfy formulas (2), (4), (5), (7), (8) and (9), respectively, and a content ratio of the sixth peptide fragment to the alkaline phosphatase satisfies formula (6):

$$(X_6/Y) \times 100 \leq 1.0000 \qquad (6),$$

wherein $X_6$ represents a peak area value of the sixth peptide fragment calculated by an automatic integration method from an extracted ion chromatogram obtained by an LC-MS/MS analysis of the dephosphorylation reagent, and Y is the same as defined above.

[65] The method according to any one of [61] to [64], wherein the alkaline phosphatase is selected from the following (a) and (b5):
(a) an alkaline phosphatase containing a protein molecule consisting of the amino acid sequence set forth in SEQ ID NO: 10; and (b5) an alkaline phosphatase containing a protein molecule consisting of an amino acid sequence that has 70% or more sequence identity to the amino acid sequence set forth in SEQ ID NO: 10 and contains positions 78 to 90, positions 177 to 187, positions 469 to 477, positions 516 to 528 and positions 534 to 551 of the amino acid sequence set forth in SEQ ID NO: 10.

[66] The method according to [65], wherein the alkaline phosphatase (b5) contains one or two or more selected from the group consisting of positions 91 to 109, positions 93 to 105 and positions 529 to 531 of the amino acid sequence set forth in SEQ ID NO: 10.

[67] The method according to [65], wherein the alkaline phosphatase (b5) contains positions 91 to 109 and positions 529 to 531 of the amino acid sequence set forth in SEQ ID NO: 10.

[68] A method of detecting a target nucleic acid, the method including the steps of:

(2-1) providing a sample containing a target nucleic acid;

(2-2) providing a dephosphorylation reagent containing an alkaline phosphatase and a peptide fragment group derived from the alkaline phosphatase;

(2-3) treating the sample with the dephosphorylation reagent to dephosphorylate the target nucleic acid;

(2-4) labeling the dephosphorylated target nucleic acid; and (2-5) detecting the labeled target nucleic acid, wherein the dephosphorylation reagent provided in step (2-2) is a dephosphorylation reagent that has been evaluated as having a high quality by the method according to any one of [1] to [67].

[69] The method according to [68], wherein the target nucleic acid is RNA.

[70] The method according to [68] or [69], wherein, in the step (2-5), the target nucleic acid is brought into contact with a probe that can be hybridized with the target nucleic acid to detect the target nucleic acid hybridized with the probe.

[71] The method according to [70], wherein the probe is fixed to a support.

We provide a method of evaluating a quality of a dephosphorylation reagent containing an alkaline phosphatase, and a method of detecting a target nucleic acid by using a dephosphorylation reagent that has been evaluated as having a high quality by the evaluation method.

DETAILED DESCRIPTION

Figure 1:
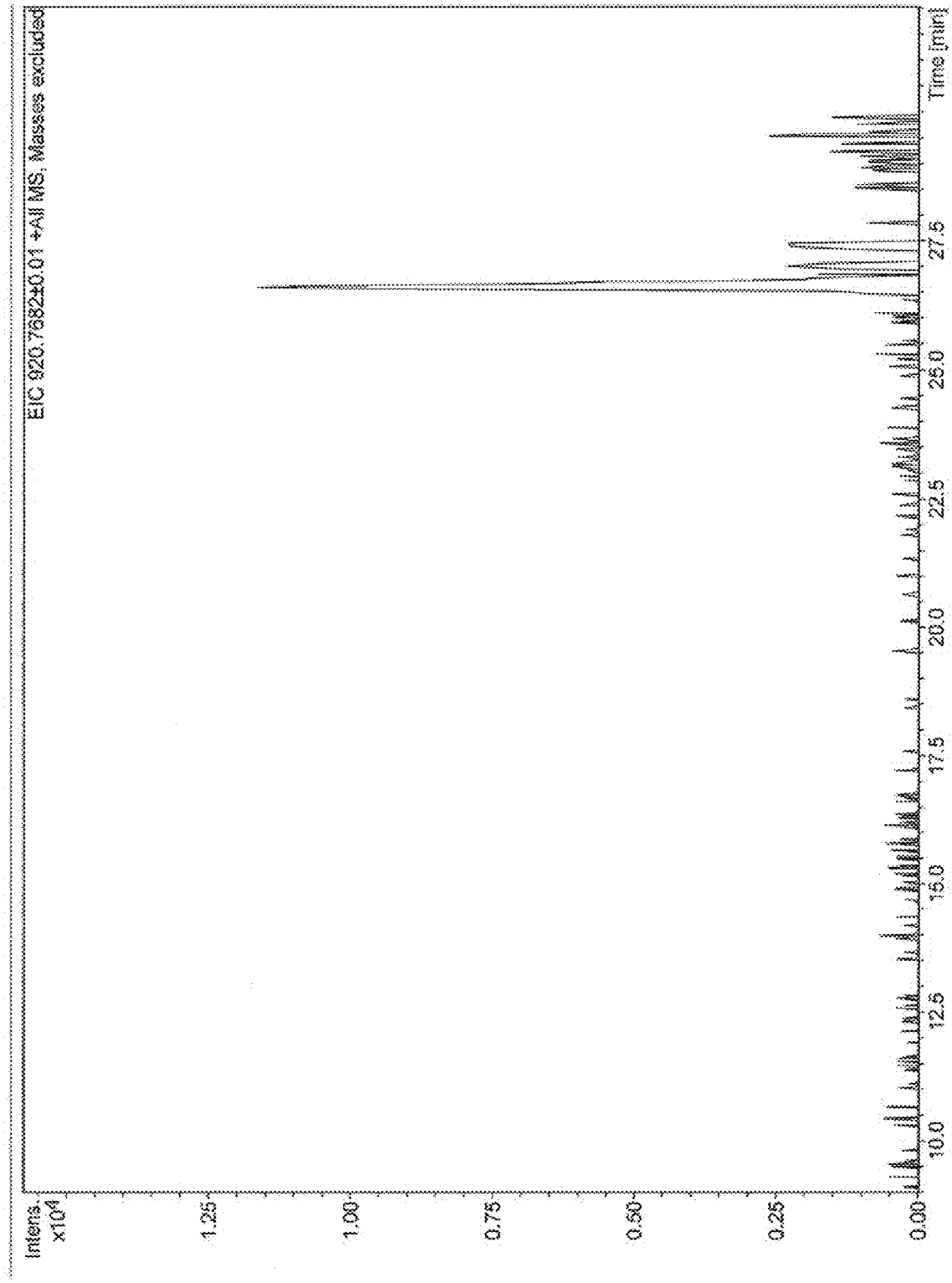
FIG. 1 shows an extracted ion chromatogram on the first peptide fragment obtained by an LC-MS/MS analysis of the composition C2 in Comparative Example 2.

Our methods will be described in detail below. It is possible to combine two or more of the methods described below, and it is possible to combine two or more of the examples described below. This disclosure also encompasses such combinations. The expression "numerical value M to numerical value N" means a range of numerical value M or more and numerical value N or less.

Description of Terms

Terms as used herein will be described below.
Alkaline Phosphatase

An alkaline phosphatase is an enzyme having alkaline phosphatase activity. The alkaline phosphatase is not particularly limited as long as it has alkaline phosphatase activity. The alkaline phosphatase activity is activity that hydrolyzes a phosphoric monoester bond in alkalinity (pH 8 to 11, e.g., pH 8 to 10 or pH 9 to 11), and the reaction form is classified into EC3.1.3.1. The alkaline phosphatase may be one alkaline phosphatase or may be a mixture of two or more alkaline phosphatases.

The structure of the alkaline phosphatase (e.g., primary structure, secondary structure, tertiary structure, quaternary structure and the like) is not particularly limited. For example, the alkaline phosphatase may have a sugar chain or may not have a sugar chain. The alkaline phosphatase may be any isozyme that can exist based on differences in the structure of a protein molecule (e.g., amino acid sequence of a protein molecule), glycosylation and the like. The alkaline phosphatase may be a monomer that is formed from one subunit or may be an oligomer that is formed from two or more subunits (e.g., dimer, tetramer and the like). The oligomer may be a homooligomer or may be a heterooligomer.

The animal from which the alkaline phosphatase is derived is not particularly limited. Examples of the animal from which the alkaline phosphatase is derived include a bovine, a shrimp, a microorganism into which a gene encoding an alkaline phosphatase has been introduced and the like. Since a bovine-derived alkaline phosphatase has high alkaline phosphatase activity, the animal from which the alkaline phosphatase is derived is preferably a bovine. When the alkaline phosphatase is derived from a bovine, the organ from which the alkaline phosphatase is derived is preferably small intestine or large intestine.

The alkaline phosphatase may be wild-type or may be mutated. The mutated alkaline phosphatase contains, for example, a protein molecule consisting of an amino acid sequence obtained by introducing deletion, substitution, insertion or addition of one or more amino acids to an amino acid sequence of a protein molecule of a wild-type alkaline phosphatase. The amino acid sequence of the protein molecule of the mutated alkaline phosphatase has preferably 70% or more, more preferably 75% or more, still more preferably 80% or more, yet more preferably 85% or more, further preferably 90% or more, and still further preferably 95% or more sequence identity to the amino acid sequence of the protein molecule of the wild-type alkaline phosphatase.

In one example, the alkaline phosphatase is selected from the following (a) and (b):
  (a) an alkaline phosphatase containing a protein molecule consisting of the amino acid sequence set forth in SEQ ID NO: 10; and
  (b) an alkaline phosphatase containing a protein molecule consisting of an amino acid sequence that has 70% or more sequence identity to the amino acid sequence set forth in SEQ ID NO: 10. In this example, the dephosphorylation reagent contains one or two or more alkaline phosphatases selected from the alkaline phosphatases (a) and (b).

In one example, the alkaline phosphatase is selected from the following (a) and (b1):
  (a) an alkaline phosphatase containing a protein molecule consisting of the amino acid sequence set forth in SEQ ID NO: 10; and
  (b1) an alkaline phosphatase containing a protein molecule consisting of an amino acid sequence that has 70% or more sequence identity to the amino acid sequence set forth in SEQ ID NO: 10 and contains positions 71 to 130 of the amino acid sequence set forth in SEQ ID NO: 10. In this example, the dephosphorylation reagent contains one or two or more alkaline phosphatases selected from the alkaline phosphatases (a) and (b1).

In one example, the alkaline phosphatase is selected from the following (a) and (b2):
  (a) an alkaline phosphatase containing a protein molecule consisting of the amino acid sequence set forth in SEQ ID NO: 10; and
  (b2) an alkaline phosphatase containing a protein molecule consisting of an amino acid sequence that has 70% or more sequence identity to the amino acid sequence set forth in SEQ ID NO: 10 and contains positions 161 to 200 of the amino acid sequence set forth in SEQ ID NO: 10. In this example, the dephosphorylation reagent contains one or two or more alkaline phosphatases selected from the alkaline phosphatases (a) and (b2).

In one example, the alkaline phosphatase is selected from the following (a) and (b3):
  (a) an alkaline phosphatase containing a protein molecule consisting of the amino acid sequence set forth in SEQ ID NO: 10; and
  (b3) an alkaline phosphatase containing a protein molecule consisting of an amino acid sequence that has 70% or more sequence identity to the amino acid sequence set forth in SEQ ID NO: 10 and contains positions 451 to 490 of the amino acid sequence set forth in SEQ ID NO: 10. In this example, the dephosphorylation reagent contains one or two or more alkaline phosphatases selected from the alkaline phosphatases (a) and (b3).

In one example, the alkaline phosphatase is selected from the following (a) and (b4):
  (a) an alkaline phosphatase containing a protein molecule consisting of the amino acid sequence set forth in SEQ ID NO: 10; and
  (b4) an alkaline phosphatase containing a protein molecule consisting of an amino acid sequence that has 70% or more sequence identity to the amino acid sequence set forth in SEQ ID NO: 10 and contains positions 501 to 578 of the amino acid sequence set forth in SEQ ID NO: 10. In this example, the dephosphorylation reagent contains one or two or more alkaline phosphatases selected from the alkaline phosphatases (a) and (b4).

In one example, the alkaline phosphatase is selected from the following (a) and (b5):
  (a) an alkaline phosphatase containing a protein molecule consisting of the amino acid sequence set forth in SEQ ID NO: 10; and
  (b5) an alkaline phosphatase containing a protein molecule consisting of an amino acid sequence that has 70% or more sequence identity to the amino acid sequence set forth in SEQ ID NO: 10 and contains positions 78 to 90, positions 177 to 187, positions 469 to 477, positions 516 to 528 and positions 534 to 551 of the amino acid sequence set forth in SEQ ID NO: 10. In this example, the dephosphorylation reagent contains one or two or more alkaline phosphatases selected from the alkaline phosphatases (a) and (b5).

Preferably, the alkaline phosphatase (b5) further contains one or two or more selected from the group consisting of positions 91 to 109, positions 93 to 105 and positions 529 to 531 of the amino acid sequence set forth in SEQ ID NO: 10.

Further preferably, the alkaline phosphatase (b5) further contains positions 91 to 109 and positions 529 to 531 of the amino acid sequence set forth in SEQ ID NO: 10.

The amino acid sequence of the protein molecule of the alkaline phosphatase (a) (i.e., the amino acid sequence set forth in SEQ ID NO: 10) corresponds to an amino acid sequence of a protein molecule of a bovine-derived alkaline phosphatase. Therefore, a bovine-derived alkaline phosphatase falls within the alkaline phosphatase (a).

The amino acid sequence of the protein molecule of the alkaline phosphatase (b) has 70% or more, preferably 75% or more, more preferably 80% or more, still more preferably 85% or more, yet more preferably 90% or more, and further preferably 95% or more sequence identity to the amino acid sequence set forth in SEQ ID NO: 10. The same applies to the amino acid sequences of the protein molecules of the alkaline phosphatases (b1) to (b5).

Both of a wild-type alkaline phosphatase (e.g., an alkaline phosphatase derived from an animal other than a bovine, a bovine-derived alkaline phosphatase having a polymorphism or the like) and a mutated alkaline phosphatase fall within the alkaline phosphatase (b). The same applies to the alkaline phosphatases (b1) to (b5).

Regarding the alkaline phosphatase (b1), the position(s) at which one or more amino acids are deleted, substituted, inserted or added in the amino acid sequence set forth in SEQ ID NO: 10 is/are a position(s) other than positions 71 to 130 of the amino acid sequence set forth in SEQ ID NO: 10.

Regarding the alkaline phosphatase (b2), the position(s) at which one or more amino acids are deleted, substituted, inserted or added in the amino acid sequence set forth in SEQ ID NO: 10 is/are a position(s) other than positions 161 to 200 of the amino acid sequence set forth in SEQ ID NO: 10.

Regarding the alkaline phosphatase (b3), the position(s) at which one or more amino acids are deleted, substituted, inserted or added in the amino acid sequence set forth in SEQ ID NO: 10 is/are a position(s) other than positions 451 to 490 of the amino acid sequence set forth in SEQ ID NO: 10.

Regarding the alkaline phosphatase (b4), the position(s) at which one or more amino acids are deleted, substituted, inserted or added in the amino acid sequence set forth in SEQ ID NO: 10 is/are a position(s) other than positions 501 to 578 of the amino acid sequence set forth in SEQ ID NO: 10.

Regarding the alkaline phosphatase (b5), the position(s) at which one or more amino acids are deleted, substituted, inserted or added in the amino acid sequence set forth in SEQ ID NO: 10 is/are a position(s) other than positions 78 to 90, positions 177 to 187, positions 469 to 477, positions 516 to 528 and positions 534 to 551 of the amino acid sequence set forth in SEQ ID NO: 10.

In an example in which the alkaline phosphatase (b5) contains one or two or more selected from the group consisting of positions 91 to 109, positions 93 to 105 and positions 529 to 531 of the amino acid sequence set forth in SEQ ID NO: 10, the position(s) at which one or more amino acids are deleted, substituted, inserted or added in the amino acid sequence set forth in SEQ ID NO: 10 is/are a position(s) other than the selected one or two or more sequences.

In an example in which the alkaline phosphatase (b5) contains positions 91 to 109 and positions 529 to 531 of the amino acid sequence set forth in SEQ ID NO: 10, the position(s) at which one or more amino acids are deleted, substituted, inserted or added in the amino acid sequence set forth in SEQ ID NO: 10 is/are a position(s) other than positions 91 to 109 and positions 529 to 531.

First Peptide Fragment

The first peptide fragment consists of the amino acid sequence set forth in SEQ ID NO: 1. The amino acid sequence of the first peptide fragment (SEQ ID NO: 1: EAEAEFLIPAEEENPAFWNRQAAQ) corresponds to positions 86 to 109 of the amino acid sequence set forth in SEQ ID NO: 10.

In an example in which the dephosphorylation reagent contains the first peptide fragment, the dephosphorylation reagent preferably further contains one or two peptide fragments selected from the group consisting of the second peptide fragment consisting of the amino acid sequence set forth in SEQ ID NO: 2 and the third peptide fragment consisting of the amino acid sequence set forth in SEQ ID NO: 3. In this example, the dephosphorylation reagent may or may not contain a peptide fragment other than the first to third peptide fragments.

The first peptide fragment can be generated by decomposition of an alkaline phosphatase containing positions 71 to 130 of the amino acid sequence set forth in SEQ ID NO: 10. The first peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the first peptide fragment, the alkaline phosphatase contained in the dephosphorylation reagent is usually an alkaline phosphatase that can generate the first peptide fragment. Preferably, the alkaline phosphatase that can generate the first peptide fragment is selected from the alkaline phosphatases (a) and (b1). In this example, the dephosphorylation reagent contains one or two or more alkaline phosphatases selected from the alkaline phosphatases (a) and (b1).

Second Peptide Fragment

The second peptide fragment consists of the amino acid sequence set forth in SEQ ID NO: 2. The amino acid sequence of the second peptide fragment (SEQ ID NO: 2: EGVSLEKREAEAE) corresponds to positions 78 to 90 of the amino acid sequence set forth in SEQ ID NO: 10.

In an example in which the dephosphorylation reagent contains the second peptide fragment, the dephosphorylation reagent preferably further contains one or two peptide fragments selected from the group consisting of the first peptide fragment consisting of the amino acid sequence set forth in SEQ ID NO: 1 and the third peptide fragment consisting of the amino acid sequence set forth in SEQ ID NO: 3. In this example, the dephosphorylation reagent may or may not contain a peptide fragment other than the first to third peptide fragments.

The second peptide fragment can be generated by decomposition of an alkaline phosphatase containing positions 71 to 130 of the amino acid sequence set forth in SEQ ID NO: 10. The second peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the second peptide fragment, the alkaline phosphatase contained in the dephosphorylation reagent is usually an alkaline phosphatase that can generate the second peptide fragment. Preferably, the alkaline phosphatase that can generate the second peptide fragment is selected from the alkaline phosphatases (a) and (b1). In this example, the dephosphorylation reagent contains one or two or more alkaline phosphatases selected from the alkaline phosphatases (a) and (b1).

Third Peptide Fragment

The third peptide fragment consists of the amino acid sequence set forth in SEQ ID NO: 3. The amino acid sequence of the third peptide fragment (SEQ ID NO: 3: IPAEEENPAFWNR) corresponds to positions 93 to 105 of the amino acid sequence set forth in SEQ ID NO: 10.

In an example in which the dephosphorylation reagent contains the third peptide fragment, the dephosphorylation reagent preferably further contains one or two peptide fragments selected from the group consisting of the first peptide fragment consisting of the amino acid sequence set forth in SEQ ID NO: 1 and the second peptide fragment consisting of the amino acid sequence set forth in SEQ ID NO: 2. In this example, the dephosphorylation reagent may or may not contain a peptide fragment other than the first to third peptide fragments.

The third peptide fragment can be generated by decomposition of an alkaline phosphatase containing positions 71 to 130 of the amino acid sequence set forth in SEQ ID NO: 10. The third peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the third peptide fragment, the alkaline phosphatase contained in the dephosphorylation reagent is usually an alkaline phosphatase that can generate the third peptide fragment. Preferably, the alkaline phosphatase that can generate the third peptide fragment is selected from the alkaline phosphatases (a) and (b1). In this example, the dephosphorylation reagent contains one or two or more alkaline phosphatases selected from the alkaline phosphatases (a) and (b1).

Fourth Peptide Fragment

The fourth peptide fragment consists of the amino acid sequence set forth in SEQ ID NO: 4. The amino acid sequence of the fourth peptide fragment (SEQ ID NO: 4: DRQVPDSAGTA) corresponds to positions 177 to 187 of the amino acid sequence set forth in SEQ ID NO: 10.

In an example in which the dephosphorylation reagent contains the fourth peptide fragment, the dephosphorylation reagent may or may not contain a peptide fragment other than the fourth peptide fragment.

The fourth peptide fragment can be generated by decomposition of an alkaline phosphatase containing positions 161 to 200 of the amino acid sequence set forth in SEQ ID NO: 10. The fourth peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the fourth peptide fragment, the alkaline phosphatase contained in the dephosphorylation reagent is usually an alkaline phosphatase that can generate the fourth peptide fragment. Preferably, the alkaline phosphatase that can generate the fourth peptide fragment is selected from the alkaline phosphatases (a) and (b2). In this example, the dephosphorylation reagent contains one or two or more alkaline phosphatases selected from the alkaline phosphatases (a) and (b2).

Fifth Peptide Fragment

The fifth peptide fragment consists of the amino acid sequence set forth in SEQ ID NO: 5. The amino acid sequence of the fifth peptide fragment (SEQ ID NO: 5: APGKALDSK) corresponds to positions 469 to 477 of the amino acid sequence set forth in SEQ ID NO: 10.

In an example in which the dephosphorylation reagent contains the fifth peptide fragment, the dephosphorylation reagent may or may not contain a peptide fragment other than the fifth peptide fragment.

The fifth peptide fragment can be generated by decomposition of an alkaline phosphatase containing positions 451 to 490 of the amino acid sequence set forth in SEQ ID NO: 10. The fifth peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the fifth peptide fragment, the alkaline phosphatase contained in the dephosphorylation reagent is usually an alkaline phosphatase that can generate the fifth peptide fragment. Preferably, the alkaline phosphatase that can generate the fifth peptide fragment is selected from the alkaline phosphatases (a) and (b3). In this example, the dephosphorylation reagent contains one or two or more alkaline phosphatases selected from the alkaline phosphatases (a) and (b3).

Sixth Peptide Fragment

The sixth peptide fragment consists of the amino acid sequence set forth in SEQ ID NO: 6. The amino acid sequence of the sixth peptide fragment (SEQ ID NO: 6: VPLASETHGGEDVAVF) corresponds to positions 516 to 531 of the amino acid sequence set forth in SEQ ID NO: 10.

In an example in which the dephosphorylation reagent contains the sixth peptide fragment, the dephosphorylation reagent preferably further contains one, two or three peptide fragments selected from the group consisting of the seventh peptide fragment consisting of the amino acid sequence set forth in SEQ ID NO: 7, the eighth peptide fragment consisting of the amino acid sequence set forth in SEQ ID NO: 8 and the ninth peptide fragment consisting of the amino acid sequence set forth in SEQ ID NO: 9. In this example, the dephosphorylation reagent may or may not contain a peptide fragment other than the sixth to ninth peptide fragments.

The sixth peptide fragment can be generated by decomposition of an alkaline phosphatase containing positions 501 to 578 of the amino acid sequence set forth in SEQ ID NO: 10. The sixth peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the sixth peptide fragment, the alkaline phosphatase contained in the dephosphorylation reagent is usually an alkaline phosphatase that can generate the sixth peptide fragment. Preferably, the alkaline phosphatase that can generate the sixth peptide fragment is selected from the alkaline phosphatases (a) and (b4). In this example, the dephosphorylation reagent contains one or two or more alkaline phosphatases selected from the alkaline phosphatases (a) and (b4).

Seventh Peptide Fragment

The seventh peptide fragment consists of the amino acid sequence set forth in SEQ ID NO: 7. The amino acid sequence of the seventh peptide fragment (SEQ ID NO: 7: VPLASETHGGEDV) corresponds to positions 516 to 528 of the amino acid sequence set forth in SEQ ID NO: 10.

In an example in which the dephosphorylation reagent contains the seventh peptide fragment, the dephosphorylation reagent preferably further contains one, two or three peptide fragments selected from the group consisting of the sixth peptide fragment consisting of the amino acid sequence set forth in SEQ ID NO: 6, the eighth peptide fragment consisting of the amino acid sequence set forth in SEQ ID NO: 8 and the ninth peptide fragment consisting of the amino acid sequence set forth in SEQ ID NO: 9. In this example, the dephosphorylation reagent may or may not contain a peptide fragment other than the sixth to ninth peptide fragments.

The seventh peptide fragment can be generated by decomposition of an alkaline phosphatase containing positions 501 to 578 of the amino acid sequence set forth in SEQ ID NO: 10. The seventh peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the seventh peptide fragment, the alkaline phosphatase contained in the dephosphorylation reagent is usually an alkaline phosphatase that can generate the seventh peptide fragment. Preferably, the alkaline phosphatase that can generate the seventh peptide fragment is selected from the alkaline phosphatases (a) and (b4). In this example, the dephosphorylation reagent contains one or two or more alkaline phosphatases selected from the alkaline phosphatases (a) and (b4).

Eighth Peptide Fragment

The eighth peptide fragment consists of the amino acid sequence set forth in SEQ ID NO: 8. The amino acid sequence of the eighth peptide fragment (SEQ ID NO: 8: GPQAHLVHGVQEETFVAH) corresponds to positions 534 to 551 of the amino acid sequence set forth in SEQ ID NO: 10.

In an example in which the dephosphorylation reagent contains the eighth peptide fragment, the dephosphorylation reagent preferably further contains one, two or three peptide fragments selected from the group consisting of the sixth peptide fragment consisting of the amino acid sequence set forth in SEQ ID NO: 6, the seventh peptide fragment consisting of the amino acid sequence set forth in SEQ ID NO: 7 and the ninth peptide fragment consisting of the amino acid sequence set forth in SEQ ID NO: 9. In this example, the dephosphorylation reagent may or may not contain a peptide fragment other than the sixth to ninth peptide fragments.

The eighth peptide fragment can be generated by decomposition of an alkaline phosphatase containing positions 501 to 578 of the amino acid sequence set forth in SEQ ID NO: 10. The eighth peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the eighth peptide fragment, the alkaline phosphatase contained in the dephosphorylation reagent is usually an alkaline phosphatase that can generate the eighth peptide fragment. Preferably, the alkaline phosphatase that can generate the eighth peptide fragment is selected from the alkaline phosphatases (a) and (b4). In this example, the dephosphorylation reagent contains one or two or more alkaline phosphatases selected from the alkaline phosphatases (a) and (b4).

Ninth Peptide Fragment

The ninth peptide fragment consists of the amino acid sequence set forth in SEQ ID NO: 9. The amino acid sequence of the ninth peptide fragment (SEQ ID NO: 9: GPQAHLVHGVQE) corresponds to positions 534 to 545 of the amino acid sequence set forth in SEQ ID NO: 10.

In an example in which the dephosphorylation reagent contains the ninth peptide fragment, the dephosphorylation reagent preferably further contains one, two or three peptide fragments selected from the group consisting of the sixth peptide fragment consisting of the amino acid sequence set forth in SEQ ID NO: 6, the seventh peptide fragment consisting of the amino acid sequence set forth in SEQ ID NO: 7 and the eighth peptide fragment consisting of the amino acid sequence set forth in SEQ ID NO: 8. In this example, the dephosphorylation reagent may or may not contain a peptide fragment other than the sixth to ninth peptide fragments.

The ninth peptide fragment can be generated by decomposition of an alkaline phosphatase containing positions 501 to 578 of the amino acid sequence set forth in SEQ ID NO: 10. The ninth peptide fragment may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the ninth peptide fragment, the alkaline phosphatase contained in the dephosphorylation reagent is usually an alkaline phosphatase that can generate the ninth peptide fragment. Preferably, the alkaline phosphatase that can generate the ninth peptide fragment is selected from the alkaline phosphatases (a) and (b4). In this example, the dephosphorylation reagent contains one or two or more alkaline phosphatases selected from the alkaline phosphatases (a) and (b4).

Peptide Fragment Group (A1)

The peptide fragment group (A1) is composed of two or more peptide fragments, and each peptide fragment constituting the peptide fragment group (A1) consists of 5 to 50 consecutive amino acid residues selected from positions 71 to 130 of the amino acid sequence set forth in SEQ ID NO: 10. The peptide fragment group (A1) is composed of, among peptide fragments contained in the dephosphorylation reagent, all peptide fragments each corresponding to a peptide fragment consisting of 5 to 50 consecutive amino acid residues selected from positions 71 to 130 of the amino acid sequence set forth in SEQ ID NO: 10. Preferably, the peptide fragment group (A1) is composed of three or more peptide fragments.

The amino acid sequence of each peptide fragment constituting the peptide fragment group (A1) is a part (moiety consisting of a plurality of consecutive amino acid residues) of positions 71 to 130 of the amino acid sequence set forth in SEQ ID NO: 10. In other words, the peptide fragment group (A1) can be generated by decomposition of positions 71 to 130 of the amino acid sequence set forth in SEQ ID NO: 10. This does not mean that the alkaline phosphatase contained in the dephosphorylation reagent is required to contain positions 71 to 130 of the amino acid sequence set forth in SEQ ID NO: 10. The alkaline phosphatase contained in the dephosphorylation reagent may not contain positions 71 to 130 of the amino acid sequence set forth in SEQ ID NO: 10. However, the alkaline phosphatase contained in the dephosphorylation reagent preferably contains positions 71 to 130 of the amino acid sequence set forth in SEQ ID NO: 10.

The amino acid sequence of each peptide fragment constituting the peptide fragment group (A1) is not particularly limited as long as the amino acid sequence is a part of positions 71 to 130 of the amino acid sequence set forth in SEQ ID NO: 10. The amino acid sequence of each peptide fragment constituting the peptide fragment group (A1) is preferably a part of positions 75 to 130 of the amino acid sequence set forth in SEQ ID NO: 10, more preferably a part of positions 75 to 125 of the amino acid sequence set forth in SEQ ID NO: 10, and still more preferably a part of positions 75 to 120 of the amino acid sequence set forth in SEQ ID NO: 10.

The number of amino acid residues constituting each peptide fragment constituting the peptide fragment group (A1) is not particularly limited as long as the number is 5 to 50, and the number is preferably 5 to 45, more preferably 10 to 40, and still more preferably 10 to 30.

Preferably, the peptide fragment group (A1) contains one, two or three peptide fragments selected from the group consisting of the first peptide fragment consisting of the amino acid sequence set forth in SEQ ID NO: 1, the second peptide fragment consisting of the amino acid sequence set forth in SEQ ID NO: 2 and the third peptide fragment consisting of the amino acid sequence set forth in SEQ ID NO: 3. In this example, the peptide fragment group (A1) may or may not contain a peptide fragment other than the first to third peptide fragments.

The amino acid sequence of the first peptide fragment (SEQ ID NO: 1: EAEAEFLIPAEEENPAFWNRQAAQ) corresponds to positions 86 to 109 of the amino acid sequence set forth in SEQ ID NO: 10. The amino acid sequence of the second peptide fragment (SEQ ID NO: 2: EGVSLEKREAEAE) corresponds to positions 78 to 90 of the amino acid sequence set forth in SEQ ID NO: 10. The amino acid sequence of the third peptide fragment (SEQ ID NO: 3: IPAEEENPAFWNR) corresponds to positions 93 to 105 of the amino acid sequence set forth in SEQ ID NO: 10.

The peptide fragment group (A1) can be generated by decomposition of an alkaline phosphatase containing positions 71 to 130 of the amino acid sequence set forth in SEQ ID NO: 10. The peptide fragment group (A1) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (A1), the alkaline phosphatase contained in the dephosphorylation reagent is usually an alkaline phosphatase that can generate the peptide fragment group (A1). Preferably, the alkaline phosphatase that can generate the peptide fragment group (A1) is selected from the alkaline phosphatases (a) and (b1). In this example, the dephosphorylation reagent contains one or two or more alkaline phosphatases selected from the alkaline phosphatases (a) and (b1).

Peptide Fragment Group (A2)

The peptide fragment group (A2) is composed of two or more peptide fragments, and each peptide fragment constituting the peptide fragment group (A2) consists of 5 to 50 consecutive amino acid residues selected from positions 71 to 130 of the amino acid sequence set forth in SEQ ID NO: 10 and contains positions 86 to 90 (EAEAE) of the amino acid sequence set forth in SEQ ID NO: 10. The peptide fragment group (A2) is composed of, among peptide fragments contained in the dephosphorylation reagent, all peptide fragments each corresponding to a peptide fragment consisting of 5 to 50 consecutive amino acid residues selected from positions 71 to 130 of the amino acid sequence set forth in SEQ ID NO: 10 and containing positions 86 to 90 of the amino acid sequence set forth in SEQ ID NO: 10.

In the amino acid sequence of each peptide fragment constituting the peptide fragment group (A2), the position at which positions 86 to 90 of the amino acid sequence set forth in SEQ ID NO: 10 are contained is not particularly limited.

The position at which positions 86 to 90 of the amino acid sequence set forth in SEQ ID NO: 10 are contained may be any of the N terminal part of a peptide fragment, the C terminal part of a peptide fragment, and a part other than the N terminal part and the C terminal part of a peptide fragment.

The amino acid sequence of each peptide fragment constituting the peptide fragment group (A2) is a part (moiety consisting of a plurality of consecutive amino acid residues) of positions 71 to 130 of the amino acid sequence set forth in SEQ ID NO: 10. In other words, the peptide fragment group (A2) can be generated by decomposition of positions 71 to 130 of the amino acid sequence set forth in SEQ ID NO: 10. This does not mean that the alkaline phosphatase contained in the dephosphorylation reagent is required to contain positions 71 to 130 of the amino acid sequence set forth in SEQ ID NO: 10. The alkaline phosphatase contained in the dephosphorylation reagent may not contain positions 71 to 130 of the amino acid sequence set forth in SEQ ID NO: 10. However, the alkaline phosphatase contained in the dephosphorylation reagent preferably contains positions 71 to 130 of the amino acid sequence set forth in SEQ ID NO: 10.

The amino acid sequence of each peptide fragment constituting the peptide fragment group (A2) is not particularly limited as long as the amino acid sequence is a part of positions 71 to 130 of the amino acid sequence set forth in SEQ ID NO: 10 and contains positions 86 to 90 of the amino acid sequence set forth in SEQ ID NO: 10. The amino acid sequence of each peptide fragment constituting the peptide fragment group (A2) is preferably a part of positions 71 to 125 of the amino acid sequence set forth in SEQ ID NO: 10, more preferably a part of positions 75 to 120 of the amino acid sequence set forth in SEQ ID NO: 10, and still more preferably a part of positions 75 to 115 of the amino acid sequence set forth in SEQ ID NO: 10.

The number of amino acid residues constituting each peptide fragment constituting the peptide fragment group (A2) is not particularly limited as long as the number is 5 to 50, and the number is preferably 5 to 40, more preferably 10 to 40, and still more preferably 10 to 30.

Preferably, the peptide fragment group (A2) contains one or two peptide fragments selected from the group consisting of the first peptide fragment consisting of the amino acid sequence set forth in SEQ ID NO: 1 and the second peptide fragment consisting of the amino acid sequence set forth in SEQ ID NO: 2. In this example, the peptide fragment group (A2) may or may not contain a peptide fragment other than the first and second peptide fragments.

The amino acid sequence of the first peptide fragment (SEQ ID NO: 1: EAEAEFLIPAEEENPAFWNRQAAQ) corresponds to positions 86 to 109 of the amino acid sequence set forth in SEQ ID NO: 10 and contains positions 86 to 90 of the amino acid sequence set forth in SEQ ID NO: 10 (the underlined part corresponds to positions 86 to 90 of the amino acid sequence set forth in SEQ ID NO: 10). The amino acid sequence of the second peptide fragment (SEQ ID NO: 2: EGVSLEKREAEAE) corresponds to positions 78 to 90 of the amino acid sequence set forth in SEQ ID NO: 10 and contains positions 86 to 90 of the amino acid sequence set forth in SEQ ID NO: 10 (the underlined part corresponds to positions 86 to 90 of the amino acid sequence set forth in SEQ ID NO: 10).

The peptide fragment group (A2) can be generated by decomposition of an alkaline phosphatase containing positions 71 to 130 of the amino acid sequence set forth in SEQ ID NO: 10. The peptide fragment group (A2) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (A2), the alkaline phosphatase contained in the dephosphorylation reagent is usually an alkaline phosphatase that can generate the peptide fragment group (A2). Preferably, the alkaline phosphatase that can generate the peptide fragment group (A2) is selected from the alkaline phosphatases (a) and (b1). In this example, the dephosphorylation reagent contains one or two or more alkaline phosphatases selected from the alkaline phosphatases (a) and (b1).

Peptide Fragment Group (A3)

The peptide fragment group (A3) is composed of two or more peptide fragments, and each peptide fragment constituting the peptide fragment group (A3) consists of 13 to 50 consecutive amino acid residues selected from positions 71 to 130 of the amino acid sequence set forth in SEQ ID NO: 10 and contains positions 93 to 105 (IPAEEENPAFWNR) of the amino acid sequence set forth in SEQ ID NO: 10. The peptide fragment group (A3) is composed of, among peptide fragments contained in the dephosphorylation reagent, all peptide fragments each corresponding to a peptide fragment consisting of 13 to 50 consecutive amino acid residues selected from positions 71 to 130 of the amino acid sequence set forth in SEQ ID NO: 10 and containing positions 93 to 105 of the amino acid sequence set forth in SEQ ID NO: 10.

In the amino acid sequence of each peptide fragment constituting the peptide fragment group (A3), the position at which positions 93 to 105 of the amino acid sequence set forth in SEQ ID NO: 10 are contained may be any of the N terminal part of a peptide fragment, the C terminal part of a peptide fragment, and a part other than the N terminal part and the C terminal part of a peptide fragment.

The amino acid sequence of each peptide fragment constituting the peptide fragment group (A3) is a part (moiety consisting of a plurality of consecutive amino acid residues) of positions 71 to 130 of the amino acid sequence set forth in SEQ ID NO: 10. In other words, the peptide fragment group (A3) can be generated by decomposition of positions 71 to 130 of the amino acid sequence set forth in SEQ ID NO: 10. This does not mean that the alkaline phosphatase contained in the dephosphorylation reagent is required to contain positions 71 to 130 of the amino acid sequence set forth in SEQ ID NO: 10. The alkaline phosphatase contained in the dephosphorylation reagent may not contain positions 71 to 130 of the amino acid sequence set forth in SEQ ID NO: 10. However, the alkaline phosphatase contained in the dephosphorylation reagent preferably contains positions 71 to 130 of the amino acid sequence set forth in SEQ ID NO: 10.

The amino acid sequence of each peptide fragment constituting the peptide fragment group (A3) is not particularly limited as long as the amino acid sequence is a part of positions 71 to 130 of the amino acid sequence set forth in SEQ ID NO: 10 and contains positions 93 to 105 of the amino acid sequence set forth in SEQ ID NO: 10. The amino acid sequence of each peptide fragment constituting the peptide fragment group (A3) is preferably a part of positions 75 to 130 of the amino acid sequence set forth in SEQ ID NO: 10, more preferably a part of positions 85 to 130 of the amino acid sequence set forth in SEQ ID NO: 10, and still more preferably a part of positions 85 to 120 of the amino acid sequence set forth in SEQ ID NO: 10.

The number of amino acid residues constituting each peptide fragment constituting the peptide fragment group (A3) is not particularly limited as long as the number is 13 to 50, and the number is preferably 13 to 45, more preferably 13 to 40, and still more preferably 13 to 30.

Preferably, the peptide fragment group (A3) contains one or two peptide fragments selected from the group consisting of the first peptide fragment consisting of the amino acid sequence set forth in SEQ ID NO: 1 and the third peptide fragment consisting of the amino acid sequence set forth in SEQ ID NO: 3. In this example, the peptide fragment group (A3) may or may not contain a peptide fragment other than the first and third peptide fragments.

The amino acid sequence of the first peptide fragment (SEQ ID NO: 1: EAEAEFLIPAEEENPAFWNRQAAQ) corresponds to positions 86 to 109 of the amino acid sequence set forth in SEQ ID NO: 10 and contains positions 93 to 105 of the amino acid sequence set forth in SEQ ID NO: 10 (the underlined part corresponds to positions 93 to 105 of the amino acid sequence set forth in SEQ ID NO: 10). The amino acid sequence of the third peptide fragment (SEQ ID NO: 3: IPAEEENPAFWNR) corresponds to positions 93 to 105 of the amino acid sequence set forth in SEQ ID NO: 10.

The peptide fragment group (A3) can be generated by decomposition of an alkaline phosphatase containing positions 71 to 130 of the amino acid sequence set forth in SEQ ID NO: 10. The peptide fragment group (A3) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (A3), the alkaline phosphatase contained in the dephosphorylation reagent is usually an alkaline phosphatase that can generate the peptide fragment group (A3). Preferably, the alkaline phosphatase that can generate the peptide fragment group (A3) is selected from the alkaline phosphatases (a) and (b1). In this example, the dephosphorylation reagent contains one or two or more alkaline phosphatases selected from the alkaline phosphatases (a) and (b1).

Peptide Fragment Group (B1)

The peptide fragment group (B1) is composed of one or more peptide fragments, and each peptide fragment constituting the peptide fragment group (B1) consists of 5 to 20 consecutive amino acid residues selected from positions 161 to 200 of the amino acid sequence set forth in SEQ ID NO: 10. The peptide fragment group (B1) is composed of, among peptide fragments contained in the dephosphorylation reagent, all peptide fragments each corresponding to a peptide fragment consisting of 5 to 20 consecutive amino acid residues selected from positions 161 to 200 of the amino acid sequence set forth in SEQ ID NO: 10.

The amino acid sequence of each peptide fragment constituting the peptide fragment group (B1) is a part (moiety consisting of a plurality of consecutive amino acid residues) of positions 161 to 200 of the amino acid sequence set forth in SEQ ID NO: 10. In other words, the peptide fragment group (B1) can be generated by decomposition of positions 161 to 200 of the amino acid sequence set forth in SEQ ID NO: 10. This does not mean that the alkaline phosphatase contained in the dephosphorylation reagent is required to contain positions 161 to 200 of the amino acid sequence set forth in SEQ ID NO: 10. The alkaline phosphatase contained in the dephosphorylation reagent may not contain positions 161 to 200 of the amino acid sequence set forth in SEQ ID NO: 10. However, the alkaline phosphatase contained in the dephosphorylation reagent preferably contains positions 161 to 200 of the amino acid sequence set forth in SEQ ID NO: 10.

The amino acid sequence of each peptide fragment constituting the peptide fragment group (B1) is not particularly limited as long as the amino acid sequence is a part of positions 161 to 200 of the amino acid sequence set forth in SEQ ID NO: 10. The amino acid sequence of each peptide fragment constituting the peptide fragment group (B1) is preferably a part of positions 161 to 195 of the amino acid sequence set forth in SEQ ID NO: 10, more preferably a part of positions 165 to 195 of the amino acid sequence set forth in SEQ ID NO: 10, and still more preferably a part of positions 165 to 190 of the amino acid sequence set forth in SEQ ID NO: 10.

The number of amino acid residues constituting each peptide fragment constituting the peptide fragment group (B1) is not particularly limited as long as the number is 5 to 20, and the number is preferably 8 to 20, more preferably 10 to 20, and still more preferably 12 to 20.

Preferably, the peptide fragment group (B1) contains the fourth peptide fragment consisting of the amino acid sequence set forth in SEQ ID NO: 4. In this example, the peptide fragment group (B1) may or may not contain a peptide fragment other than the fourth peptide fragment.

The amino acid sequence of the fourth peptide fragment (SEQ ID NO: 4: DRQVPDSAGTA) corresponds to positions 177 to 187 of the amino acid sequence set forth in SEQ ID NO: 10.

The peptide fragment group (B1) can be generated by decomposition of an alkaline phosphatase containing positions 161 to 200 of the amino acid sequence set forth in SEQ ID NO: 10. The peptide fragment group (B1) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (B1), the alkaline phosphatase contained in the dephosphorylation reagent is usually an alkaline phosphatase that can generate the peptide fragment group (B1). Preferably, the alkaline phosphatase that can generate the peptide fragment group (B1) is selected from the alkaline phosphatases (a) and (b2). In this example, the dephosphorylation reagent contains one or two or more alkaline phosphatases selected from the alkaline phosphatases (a) and (b2).

Peptide Fragment Group (B2)

The peptide fragment group (B2) is composed of one or more peptide fragments, and each peptide fragment constituting the peptide fragment group (B2) consists of 11 to 20 consecutive amino acid residues selected from positions 161 to 200 of the amino acid sequence set forth in SEQ ID NO: 10 and contains positions 177 to 187 (DRQVPDSAGTA) of the amino acid sequence set forth in SEQ ID NO: 10. The peptide fragment group (B2) may be composed of one or more peptide fragments, or may be composed of two or more peptide fragments. The peptide fragment group (B2) is composed of, among peptide fragments contained in the dephosphorylation reagent, all peptide fragments each corresponding to a peptide fragment consisting of 11 to 20 consecutive amino acid residues selected from positions 161 to 200 of the amino acid sequence set forth in SEQ ID NO: 10 and containing positions 177 to 187 of the amino acid sequence set forth in SEQ ID NO: 10.

In the amino acid sequence of each peptide fragment constituting the peptide fragment group (B2), the position at which positions 177 to 187 of the amino acid sequence set forth in SEQ ID NO: 10 are contained is not particularly limited. The position at which positions 177 to 187 of the amino acid sequence set forth in SEQ ID NO: 10 are contained may be any of the N terminal part of a peptide fragment, the C terminal part of a peptide fragment, and a part other than the N terminal part and the C terminal part of a peptide fragment.

The amino acid sequence of each peptide fragment constituting the peptide fragment group (B2) is a part (moiety consisting of a plurality of consecutive amino acid residues) of positions 161 to 200 of the amino acid sequence set forth in SEQ ID NO: 10. In other words, the peptide fragment group (B2) can be generated by decomposition of positions 161 to 200 of the amino acid sequence set forth in SEQ ID NO: 10. This does not mean that the alkaline phosphatase contained in the dephosphorylation reagent is required to contain positions 161 to 200 of the amino acid sequence set forth in SEQ ID NO: 10. The alkaline phosphatase contained in the dephosphorylation reagent may not contain positions 161 to 200 of the amino acid sequence set forth in SEQ ID NO: 10. However, the alkaline phosphatase contained in the dephosphorylation reagent preferably contains positions 161 to 200 of the amino acid sequence set forth in SEQ ID NO: 10.

The amino acid sequence of each peptide fragment constituting the peptide fragment group (B2) is not particularly limited as long as the amino acid sequence is a part of positions 161 to 200 of the amino acid sequence set forth in SEQ ID NO: 10 and contains positions 177 to 187 of the amino acid sequence set forth in SEQ ID NO: 10. The amino acid sequence of each peptide fragment constituting the peptide fragment group (B2) is preferably a part of positions 161 to 195 of the amino acid sequence set forth in SEQ ID NO: 10, more preferably a part of positions 161 to 190 of the amino acid sequence set forth in SEQ ID NO: 10, and still more preferably a part of positions 165 to 190 of the amino acid sequence set forth in SEQ ID NO: 10.

The number of amino acid residues constituting each peptide fragment constituting the peptide fragment group (B2) is not particularly limited as long as the number is 11 to 20, and the number is preferably 8 to 20, more preferably 10 to 20, and still more preferably 12 to 20.

Preferably, the peptide fragment group (B2) contains the fourth peptide fragment consisting of the amino acid sequence set forth in SEQ ID NO: 4. In this example, the peptide fragment group (B2) may or may not contain a peptide fragment other than the fourth peptide fragment.

The amino acid sequence (SEQ ID NO: 4: DRQVPDSAGTA) of the fourth peptide fragment corresponds to positions 177 to 187 of the amino acid sequence set forth in SEQ ID NO: 10.

The peptide fragment group (B2) can be generated by decomposition of an alkaline phosphatase containing positions 161 to 200 of the amino acid sequence set forth in SEQ ID NO: 10. The peptide fragment group (B2) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (B2), the alkaline phosphatase contained in the dephosphorylation reagent is usually an alkaline phosphatase that can generate the peptide fragment group (B2). Preferably, the alkaline phosphatase that can generate the peptide fragment group (B2) is selected from the alkaline phosphatases (a) and (b2). In this example, the dephosphorylation reagent contains one or two or more alkaline phosphatases selected from the alkaline phosphatases (a) and (b2).

Peptide Fragment Group (C1)

The peptide fragment group (C1) is composed of one or more peptide fragments, and each peptide fragment constituting the peptide fragment group (C1) consists of 5 to 20 consecutive amino acid residues selected from positions 451 to 490 of the amino acid sequence set forth in SEQ ID NO: 10. The peptide fragment group (C1) is composed of, among peptide fragments contained in the dephosphorylation reagent, all peptide fragments each corresponding to a peptide fragment consisting of 5 to 20 consecutive amino acid residues selected from positions 451 to 490 of the amino acid sequence set forth in SEQ ID NO: 10.

The amino acid sequence of each peptide fragment constituting the peptide fragment group (C1) is a part (moiety consisting of a plurality of consecutive amino acid residues) of positions 451 to 490 of the amino acid sequence set forth in SEQ ID NO: 10. In other words, the peptide fragment group (C1) can be generated by decomposition of positions 451 to 490 of the amino acid sequence set forth in SEQ ID NO: 10. This does not mean that the alkaline phosphatase contained in the dephosphorylation reagent is required to contain positions 451 to 490 of the amino acid sequence set forth in SEQ ID NO: 10. The alkaline phosphatase contained in the dephosphorylation reagent may not contain positions 451 to 490 of the amino acid sequence set forth in SEQ ID NO: 10. However, the alkaline phosphatase contained in the dephosphorylation reagent preferably contains positions 451 to 490 of the amino acid sequence set forth in SEQ ID NO: 10.

The amino acid sequence of each peptide fragment constituting the peptide fragment group (C1) is not particularly limited as long as the amino acid sequence is a part of positions 451 to 490 of the amino acid sequence set forth in SEQ ID NO: 10. The amino acid sequence of each peptide fragment constituting the peptide fragment group (C1) is preferably a part of positions 455 to 490 of the amino acid sequence set forth in SEQ ID NO: 10, more preferably a part of positions 461 to 490 of the amino acid sequence set forth in SEQ ID NO: 10, and still more preferably a part of positions 465 to 490 of the amino acid sequence set forth in SEQ ID NO: 10.

The number of amino acid residues constituting each peptide fragment constituting the peptide fragment group (C1) is not particularly limited as long as the number is 5 to 20, and the number is preferably 6 to 20, more preferably 7 to 20, and still more preferably 8 to 20.

Preferably, the peptide fragment group (C1) contains the fifth peptide fragment consisting of the amino acid sequence set forth in SEQ ID NO: 5. In this example, the peptide fragment group (C1) may or may not contain a peptide fragment other than the fifth peptide fragment.

The amino acid sequence of the fifth peptide fragment (SEQ ID NO: 5: APGKALDSK) corresponds to positions 469 to 477 of the amino acid sequence set forth in SEQ ID NO: 10.

The peptide fragment group (C1) can be generated by decomposition of an alkaline phosphatase containing positions 451 to 490 of the amino acid sequence set forth in SEQ ID NO: 10. The peptide fragment group (C1) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (C1), the alkaline phosphatase contained in the dephosphorylation reagent is usually an alkaline phosphatase that can generate the peptide fragment group (C1). Preferably, the alkaline phosphatase that can generate the peptide fragment group (C1) is selected from the alkaline phosphatases (a) and (b3). In this example, the dephosphorylation reagent contains one or two or more alkaline phosphatases selected from the alkaline phosphatases (a) and (b3).

Peptide Fragment Group (C2)

The peptide fragment group (C2) is composed of one or more peptide fragments, and each peptide fragment constituting the peptide fragment group (C2) consists of 9 to 20 consecutive amino acid residues selected from positions 451 to 490 of the amino acid sequence set forth in SEQ ID NO: 10 and contains positions 469 to 477 (APGKALDSK) of the amino acid sequence set forth in SEQ ID NO: 10. The peptide fragment group (C2) is composed of, among peptide fragments contained in the dephosphorylation reagent, all peptide fragments each corresponding to a peptide fragment consisting of 9 to 20 consecutive amino acid residues selected from positions 451 to 490 of the amino acid sequence set forth in SEQ ID NO: 10 and containing positions 469 to 477 of the amino acid sequence set forth in SEQ ID NO: 10.

In the amino acid sequence of each peptide fragment constituting the peptide fragment group (C2), the position at which positions 469 to 477 of the amino acid sequence set forth in SEQ ID NO: 10 are contained is not particularly limited. The position at which positions 469 to 477 of the amino acid sequence set forth in SEQ ID NO: 10 are contained may be any of the N terminal part of a peptide fragment, the C terminal part of a peptide fragment, and a part other than the N terminal part and the C terminal part of a peptide fragment.

The amino acid sequence of each peptide fragment constituting the peptide fragment group (C2) is a part (moiety consisting of a plurality of consecutive amino acid residues) of positions 451 to 490 of the amino acid sequence set forth in SEQ ID NO: 10. In other words, the peptide fragment group (C2) can be generated by decomposition of positions 451 to 490 of the amino acid sequence set forth in SEQ ID NO: 10. This does not mean that the alkaline phosphatase contained in the dephosphorylation reagent is required to contain positions 451 to 490 of the amino acid sequence set forth in SEQ ID NO: 10. The alkaline phosphatase contained in the dephosphorylation reagent may not contain positions 451 to 490 of the amino acid sequence set forth in SEQ ID NO: 10. However, the alkaline phosphatase contained in the dephosphorylation reagent preferably contains positions 451 to 490 of the amino acid sequence set forth in SEQ ID NO: 10.

The amino acid sequence of each peptide fragment constituting the peptide fragment group (C2) is not particularly limited as long as the amino acid sequence is a part of positions 451 to 490 of the amino acid sequence set forth in SEQ ID NO: 10 and contains positions 469 to 477 of the amino acid sequence set forth in SEQ ID NO: 10. The amino acid sequence of each peptide fragment constituting the peptide fragment group (C2) is preferably a part of positions 455 to 490 of the amino acid sequence set forth in SEQ ID NO: 10, more preferably a part of positions 461 to 490 of the amino acid sequence set forth in SEQ ID NO: 10, and still more preferably a part of positions 465 to 490 of the amino acid sequence set forth in SEQ ID NO: 10.

The number of amino acid residues constituting each peptide fragment constituting the peptide fragment group (C2) is not particularly limited as long as the number is 9 to 20, and the number is preferably 9 to 19, more preferably 9 to 18, and still more preferably 9 to 17.

Preferably, the peptide fragment group (C2) contains the fifth peptide fragment consisting of the amino acid sequence set forth in SEQ ID NO: 5. In this example, the peptide fragment group (C2) may or may not contain a peptide fragment other than the fifth peptide fragment.

The amino acid sequence of the fifth peptide fragment (SEQ ID NO: 5: APGKALDSK) corresponds to positions 469 to 477 of the amino acid sequence set forth in SEQ ID NO: 10.

The peptide fragment group (C2) can be generated by decomposition of an alkaline phosphatase containing positions 451 to 490 of the amino acid sequence set forth in SEQ ID NO: 10. The peptide fragment group (C2) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (C2), the alkaline phosphatase contained in the dephosphorylation reagent is an alkaline phosphatase that can generate the peptide fragment group (C2). Preferably, the alkaline phosphatase that can generate the peptide fragment group (C2) is selected from the alkaline phosphatases (a) and (b3). In this example, the dephosphorylation reagent contains one or two or more alkaline phosphatases selected from the alkaline phosphatases (a) and (b3).

Peptide Fragment Group (D1)

The peptide fragment group (D1) is composed of two or more peptide fragments, and each peptide fragment constituting the peptide fragment group (D1) consists of 5 to 50 consecutive amino acid residues selected from positions 501 to 578 of the amino acid sequence set forth in SEQ ID NO: 10. The peptide fragment group (D1) is composed of, among peptide fragments contained in the dephosphorylation reagent, all peptide fragments each corresponding to a peptide fragment consisting of 5 to 50 consecutive amino acid residues selected from positions 501 to 578 of the amino acid sequence set forth in SEQ ID NO: 10. Preferably, the peptide fragment group (D1) is composed of three or more peptide fragments. More preferably, the peptide fragment group (D1) is composed of four or more peptide fragments.

The amino acid sequence of each peptide fragment constituting the peptide fragment group (D1) is a part (moiety consisting of a plurality of consecutive amino acid residues) of positions 501 to 578 of the amino acid sequence set forth in SEQ ID NO: 10. In other words, the peptide fragment group (D1) can be generated by decomposition of positions 501 to 578 of the amino acid sequence set forth in SEQ ID NO: 10. This does not mean that the alkaline phosphatase contained in the dephosphorylation reagent is required to contain positions 501 to 578 of the amino acid sequence set forth in SEQ ID NO: 10. The alkaline phosphatase contained in the dephosphorylation reagent may not contain positions 501 to 578 of the amino acid sequence set forth in SEQ ID NO: 10. However, the alkaline phosphatase contained in the dephosphorylation reagent preferably contains positions 501 to 578 of the amino acid sequence set forth in SEQ ID NO: 10.

The amino acid sequence of each peptide fragment constituting the peptide fragment group (D1) is not particularly limited as long as the amino acid sequence is a part of positions 501 to 578 of the amino acid sequence set forth in SEQ ID NO: 10. The amino acid sequence of each peptide fragment constituting the peptide fragment group (D1) is preferably a part of positions 505 to 578 of the amino acid sequence set forth in SEQ ID NO: 10, more preferably a part of positions 511 to 578 of the amino acid sequence set forth in SEQ ID NO: 10, and still more preferably a part of positions 511 to 571 of the amino acid sequence set forth in SEQ ID NO: 10.

The number of amino acid residues constituting each peptide fragment constituting the peptide fragment group (D1) is not particularly limited as long as the number is 5 to 50, and the number is preferably 5 to 45, more preferably 10 to 40, and still more preferably 10 to 30.

Preferably, the peptide fragment group (D1) contains one, two, three or four peptide fragments selected from the group consisting of the sixth peptide fragment consisting of the amino acid sequence set forth in SEQ ID NO: 6, the seventh peptide fragment consisting of the amino acid sequence set forth in SEQ ID NO: 7, the eighth peptide fragment consisting of the amino acid sequence set forth in SEQ ID NO: 8 and the ninth peptide fragment consisting of the amino acid sequence set forth in SEQ ID NO: 9. In this example, the peptide fragment group (D1) may or may not contain a peptide fragment other than the sixth to ninth peptide fragments.

The amino acid sequence of the sixth peptide fragment (SEQ ID NO: 6: VPLASETHGGEDVAVF) corresponds to positions 516 to 531 of the amino acid sequence set forth in SEQ ID NO: 10. The amino acid sequence of the seventh peptide fragment (SEQ ID NO: 7: VPLASETHGGEDV) corresponds to positions 516 to 528 of the amino acid sequence set forth in SEQ ID NO: 10. The amino acid sequence of the eighth peptide fragment (SEQ ID NO: 8: GPQAHLVHGVQEETFVAH) corresponds to positions 534 to 551 of the amino acid sequence set forth in SEQ ID NO: 10. The amino acid sequence of the eighth peptide fragment (SEQ ID NO: 9: GPQAHLVHGVQE) corresponds to positions 534 to 545 of the amino acid sequence set forth in SEQ ID NO: 10.

The peptide fragment group (D1) can be generated by decomposition of an alkaline phosphatase containing positions 501 to 578 of the amino acid sequence set forth in SEQ ID NO: 10. The peptide fragment group (D1) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (D1), the alkaline phosphatase contained in the dephosphorylation reagent is usually an alkaline phosphatase that can generate the peptide fragment group (D1). Preferably, the alkaline phosphatase that can generate the peptide fragment group (D1) is selected from the alkaline phosphatases (a) and (b4). In this example, the dephosphorylation reagent contains one or two or more alkaline phosphatases selected from the alkaline phosphatases (a) and (b4).

Peptide Fragment Group (D2)

The peptide fragment group (D2) is composed of two or more peptide fragments, and each peptide fragment constituting the peptide fragment group (D2) consists of 13 to 50 consecutive amino acid residues selected from positions 501 to 578 of the amino acid sequence set forth in SEQ ID NO: 10 and contains positions 516 to 528 (VPLASETHGGEDV) of the amino acid sequence set forth in SEQ ID NO: 10. The peptide fragment group (D2) is composed of, among peptide fragments contained in the dephosphorylation reagent, all peptide fragments each corresponding to a peptide fragment consisting of 13 to 50 consecutive amino acid residues selected from positions 501 to 578 of the amino acid sequence set forth in SEQ ID NO: 10 and containing positions 516 to 528 of the amino acid sequence set forth in SEQ ID NO: 10.

In the amino acid sequence of each peptide fragment constituting the peptide fragment group (D2), the position at which positions 516 to 528 of the amino acid sequence set forth in SEQ ID NO: 10 are contained is not particularly limited. The position at which positions 516 to 528 of the amino acid sequence set forth in SEQ ID NO: 10 are contained may be any of the N terminal part of a peptide fragment, the C terminal part of a peptide fragment, and a part other than the N terminal part and the C terminal part of a peptide fragment.

The amino acid sequence of each peptide fragment constituting the peptide fragment group (D2) is a part (moiety consisting of a plurality of consecutive amino acid residues) of positions 501 to 578 of the amino acid sequence set forth in SEQ ID NO: 10. In other words, the peptide fragment group (D2) can be generated by decomposition of positions 501 to 578 of the amino acid sequence set forth in SEQ ID NO: 10. This does not mean that the alkaline phosphatase contained in the dephosphorylation reagent is required to contain positions 501 to 578 of the amino acid sequence set forth in SEQ ID NO: 10. The alkaline phosphatase contained in the dephosphorylation reagent may not contain positions 501 to 578 of the amino acid sequence set forth in SEQ ID NO: 10. However, the alkaline phosphatase contained in the dephosphorylation reagent preferably contains positions 501 to 578 of the amino acid sequence set forth in SEQ ID NO: 10.

The amino acid sequence of each peptide fragment constituting the peptide fragment group (D2) is not particularly limited as long as the amino acid sequence is a part of positions 501 to 578 of the amino acid sequence set forth in SEQ ID NO: 10 and contains positions 516 to 528 of the amino acid sequence set forth in SEQ ID NO: 10. The amino acid sequence of each peptide fragment constituting the peptide fragment group (D2) is preferably a part of positions 501 to 570 of the amino acid sequence set forth in SEQ ID NO: 10, more preferably a part of positions 501 to 560 of the amino acid sequence set forth in SEQ ID NO: 10, and still more preferably a part of positions 501 to 555 of the amino acid sequence set forth in SEQ ID NO: 10.

The number of amino acid residues constituting each peptide fragment constituting the peptide fragment group (D2) is not particularly limited as long as the number is 13 to 50, and the number is preferably 13 to 45, more preferably 13 to 40, and still more preferably 13 to 35.

Preferably, the peptide fragment group (D2) contains one or two peptide fragments selected from the group consisting of the sixth peptide fragment consisting of the amino acid sequence set forth in SEQ ID NO: 6 and the seventh peptide fragment consisting of the amino acid sequence set forth in SEQ ID NO: 7. In this example, the peptide fragment group (D2) may or may not contain a peptide fragment other than the sixth and seventh peptide fragments.

The amino acid sequence of the sixth peptide fragment (SEQ ID NO: 6: VPLASETHGGEDVAVF) corresponds to positions 516 to 531 of the amino acid sequence set forth in SEQ ID NO: 10 and contains positions 516 to 528 of the amino acid sequence set forth in SEQ ID NO: 10 (the underlined part corresponds to positions 516 to 528 of the amino acid sequence set forth in SEQ ID NO: 10). The amino acid sequence of the seventh peptide fragment (SEQ ID NO: 7: VPLASETHGGEDV) corresponds to positions 516 to 528 of the amino acid sequence set forth in SEQ ID NO: 10.

The peptide fragment group (D2) can be generated by decomposition of an alkaline phosphatase containing positions 501 to 578 of the amino acid sequence set forth in SEQ ID NO: 10. The peptide fragment group (D2) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (D2), the alkaline phosphatase contained in the dephosphorylation reagent is an alkaline phosphatase that can generate the peptide fragment group (D2). Preferably, the alkaline phosphatase that can generate the peptide fragment group (D2) is selected from the alkaline phosphatases (a) and (b4). In this example, the dephosphorylation reagent contains one or two or more alkaline phosphatases selected from the alkaline phosphatases (a) and (b4).

Peptide Fragment Group (D3)

The peptide fragment group (D3) is composed of two or more peptide fragments, and each peptide fragment constituting the peptide fragment group (D3) consists of 12 to 50 consecutive amino acid residues selected from positions 501 to 578 of the amino acid sequence set forth in SEQ ID NO: 10 and contains positions 534 to 545 (GPQAHLVHGVQE) of the amino acid sequence set forth in SEQ ID NO: 10. The peptide fragment group (D3) is composed of, among peptide fragments contained in the dephosphorylation reagent, all peptide fragments each corresponding to a peptide fragment consisting of 12 to 50 consecutive amino acid residues selected from positions 501 to 578 of the amino acid sequence set forth in SEQ ID NO: 10 and containing positions 534 to 545 of the amino acid sequence set forth in SEQ ID NO: 10.

In the amino acid sequence of each peptide fragment constituting the peptide fragment group (D3), the position at which positions 534 to 545 of the amino acid sequence set forth in SEQ ID NO: 10 are contained may be any of the N terminal part of a peptide fragment, the C terminal part of a peptide fragment, and a part other than the N terminal part and the C terminal part of a peptide fragment.

The amino acid sequence of each peptide fragment constituting the peptide fragment group (D3) is a part (moiety consisting of a plurality of consecutive amino acid residues) of positions 501 to 578 of the amino acid sequence set forth in SEQ ID NO: 10. In other words, the peptide fragment group (D3) can be generated by decomposition of positions 501 to 578 of the amino acid sequence set forth in SEQ ID NO: 10. This does not mean that the alkaline phosphatase contained in the dephosphorylation reagent is required to contain positions 501 to 578 of the amino acid sequence set forth in SEQ ID NO: 10. The alkaline phosphatase contained in the dephosphorylation reagent may not contain positions 501 to 578 of the amino acid sequence set forth in SEQ ID NO: 10. However, the alkaline phosphatase contained in the dephosphorylation reagent preferably contains positions 501 to 578 of the amino acid sequence set forth in SEQ ID NO: 10.

The amino acid sequence of each peptide fragment constituting the peptide fragment group (D3) is not particularly limited as long as the amino acid sequence is a part of positions 501 to 578 of the amino acid sequence set forth in SEQ ID NO: 10 and contains positions 534 to 545 of the amino acid sequence set forth in SEQ ID NO: 10. The amino acid sequence of each peptide fragment constituting the peptide fragment group (D3) is preferably a part of positions 506 to 578 of the amino acid sequence set forth in SEQ ID NO: 10, more preferably a part of positions 511 to 578 of the amino acid sequence set forth in SEQ ID NO: 10, and still more preferably a part of positions 521 to 578 of the amino acid sequence set forth in SEQ ID NO: 10.

The number of amino acid residues constituting each peptide fragment constituting the peptide fragment group (D3) is not particularly limited as long as the number is 12 to 50, and the number is preferably 12 to 45, more preferably 12 to 40, and still more preferably 12 to 35.

Preferably, the peptide fragment group (D3) contains one or two peptide fragments selected from the group consisting of the eighth peptide fragment consisting of the amino acid sequence set forth in SEQ ID NO: 8 and the ninth peptide fragment consisting of the amino acid sequence set forth in SEQ ID NO: 9. In this example, the peptide fragment group (D3) may or may not contain a peptide fragment other than the eighth and ninth peptide fragments.

The amino acid sequence of the eighth peptide fragment (SEQ ID NO: 8: GPQAHLVHGVQEETFVAH) corresponds to positions 534 to 551 of the amino acid sequence set forth in SEQ ID NO: 10 and contains positions 534 to 545 of the amino acid sequence set forth in SEQ ID NO: 10 (the underlined part corresponds to positions 534 to 545 of the amino acid sequence set forth in SEQ ID NO: 10). The amino acid sequence of the ninth peptide fragment (SEQ ID NO: 9: GPQAHLVHGVQE) corresponds to positions 534 to 545 of the amino acid sequence set forth in SEQ ID NO: 10.

The peptide fragment group (D3) can be generated by decomposition of an alkaline phosphatase containing positions 501 to 578 of the amino acid sequence set forth in SEQ ID NO: 10. The peptide fragment group (D3) may be one generated by decomposition of an alkaline phosphatase not contained in the dephosphorylation reagent, but is usually one generated by decomposition of an alkaline phosphatase contained in the dephosphorylation reagent. Therefore, in an example in which the dephosphorylation reagent contains the peptide fragment group (D3), the alkaline phosphatase contained in the dephosphorylation reagent is an alkaline phosphatase that can generate the peptide fragment group (D3). Preferably, the alkaline phosphatase that can generate the peptide fragment group (D3) is selected from the alkaline phosphatases (a) and (b4). In this example, the dephosphorylation reagent contains one or two or more alkaline phosphatases selected from the alkaline phosphatases (a) and (b4).

Description of Formulas

Formulas as used herein will be described.
Formulas as used herein are as follows.

$$(X_{A1}/Y) \times 100 \leq 5.0000 \tag{A1}$$

$$(X_{A2}/Y) \times 100 \leq 2.4000 \tag{A2}$$

$$(X_{A3}/Y) \times 100 \leq 4.5000 \tag{A3}$$

$$(X_{B1}/Y) \times 100 \leq 0.6000 \tag{B1}$$

$$(X_{B2}/Y) \times 100 \leq 0.6000 \tag{B2}$$

$$(X_{C1}/Y) \times 100 \leq 0.1800 \tag{C1}$$

$$(X_{C2}/Y) \times 100 \leq 0.1800 \tag{C2}$$

$$(X_{D1}/Y) \times 100 \leq 4.4000 \tag{D1}$$

$$(X_{D2}/Y) \times 100 \leq 3.4000 \tag{D2}$$

$$(X_{D3}/Y) \times 100 \leq 1.0000 \tag{D3}$$

$$(X_{1}/Y) \times 100 \leq 1.0000 \tag{1}$$

$$(X_{2}/Y) \times 100 \leq 0.8000 \tag{2}$$

$$(X_{3}/Y) \times 100 \leq 2.3000 \tag{3}$$

$$(X_{4}/Y) \times 100 \leq 0.6000 \tag{4}$$

$$(X_{5}/Y) \times 100 \leq 0.1800 \tag{5}$$

$$(X_{6}/Y) \times 100 \leq 1.0000 \tag{6}$$

$$(X_{7}/Y) \times 100 \leq 1.6000 \tag{7}$$

$$(X_{8}/Y) \times 100 \leq 0.2000 \tag{8}$$

$$(X_{9}/Y) \times 100 \leq 0.3500 \tag{9}$$

In formula (A1), $X_{A1}$ represents a peak area value of the peptide fragment group (A1) calculated by an automatic integration method from an extracted ion chromatogram obtained by an LC-MS/MS analysis of the dephosphorylation reagent. The "peak area value of the peptide fragment group (A1)" means a total peak area value of all peptide fragments constituting the peptide fragment group (A1).

In formula (A2), $X_{A2}$ represents a peak area value of the peptide fragment group (A2) calculated by an automatic integration method from an extracted ion chromatogram obtained by an LC-MS/MS analysis of the dephosphorylation reagent. The "peak area value of the peptide fragment group (A2)" means a total peak area value of all peptide fragments constituting the peptide fragment group (A2).

In formula (A3), $X_{A3}$ represents a peak area value of the peptide fragment group (A3) calculated by an automatic integration method from an extracted ion chromatogram obtained by an LC-MS/MS analysis of the dephosphorylation reagent. The "peak area value of the peptide fragment group (A3)" means a total peak area value of all peptide fragments constituting the peptide fragment group (A3).

In formula (B1), $X_{B1}$ represents a peak area value of the peptide fragment group (B1) calculated by an automatic integration method from an extracted ion chromatogram obtained by an LC-MS/MS analysis of the dephosphorylation reagent. The "peak area value of the peptide fragment group (B1)" means, when the peptide fragment group (B1) is composed of one peptide fragment, a peak area value of the one peptide fragment, and, when the peptide fragment group (B1) is composed of two or more peptide fragments, a total peak area value of the two or more peptide fragments (i.e., total peak area value of all peptide fragments constituting the peptide fragment group (B1)).

In formula (B2), $X_{B2}$ represents a peak area value of the peptide fragment group (B2) calculated by an automatic integration method from an extracted ion chromatogram obtained by an LC-MS/MS analysis of the dephosphorylation reagent. The "peak area value of the peptide fragment group (B2)" means, when the peptide fragment group (B2) is composed of one peptide fragment, a peak area value of the one peptide fragment, and, when the peptide fragment group (B2) is composed of two or more peptide fragments, a total peak area value of the two or more peptide fragments (i.e., total peak area value of all peptide fragments constituting the peptide fragment group (B2)).

In formula (C1), $X_{C1}$ represents a peak area value of the peptide fragment group (C1) calculated by an automatic integration method from an extracted ion chromatogram obtained by an LC-MS/MS analysis of the dephosphorylation reagent. The "peak area value of the peptide fragment group (C1)" means, when the peptide fragment group (C1) is composed of one peptide fragment, a peak area value of the one peptide fragment, and, when the peptide fragment group (C1) is composed of two or more peptide fragments, a total peak area value of the two or more peptide fragments (i.e., total peak area value of all peptide fragments constituting the peptide fragment group (C1)).

In formula (C2), $X_{C2}$ represents a peak area value of the peptide fragment group (C2) calculated by an automatic integration method from an extracted ion chromatogram obtained by an LC-MS/MS analysis of the dephosphorylation reagent. The "peak area value of the peptide fragment group (C2)" means, when the peptide fragment group (C2) is composed of one peptide fragment, a peak area value of the one peptide fragment, and, when the peptide fragment group (C2) is composed of two or more peptide fragments, a total peak area value of the two or more peptide fragments (i.e., total peak area value of all peptide fragments constituting the peptide fragment group (C2)).

In formula (D1), $X_{D1}$ represents a peak area value of the peptide fragment group (D1) calculated by an automatic integration method from an extracted ion chromatogram obtained by an LC-MS/MS analysis of the dephosphorylation reagent. The "peak area value of the peptide fragment group (D1)" means a total peak area value of all peptide fragments constituting the peptide fragment group (D1).

In formula (D2), $X_{D2}$ represents a peak area value of the peptide fragment group (D2) calculated by an automatic integration method from an extracted ion chromatogram obtained by an LC-MS/MS analysis of the dephosphorylation reagent. The "peak area value of the peptide fragment group (D2)" means a total peak area value of all peptide fragments constituting the peptide fragment group (D2).

In formula (D3), $X_{D3}$ represents a peak area value of the peptide fragment group (D3) calculated by an automatic integration method from an extracted ion chromatogram obtained by an LC-MS/MS analysis of the dephosphorylation reagent. The "peak area value of the peptide fragment group (D3)" means a total peak area value of all peptide fragments constituting the peptide fragment group (D3).

In formula (1), $X_1$ represents a peak area value of the first peptide fragment calculated by an automatic integration method from an extracted ion chromatogram obtained by an LC-MS/MS analysis of the dephosphorylation reagent.

In formula (2), $X_2$ represents a peak area value of the second peptide fragment calculated by an automatic integration method from an extracted ion chromatogram obtained by an LC-MS/MS analysis of the dephosphorylation reagent.

In formula (3), $X_3$ represents a peak area value of the third peptide fragment calculated by an automatic integration method from an extracted ion chromatogram obtained by an LC-MS/MS analysis of the dephosphorylation reagent.

In formula (4), $X_4$ represents a peak area value of the fourth peptide fragment calculated by an automatic integration method from an extracted ion chromatogram obtained by an LC-MS/MS analysis of the dephosphorylation reagent.

In formula (5), $X_5$ represents a peak area value of the fifth peptide fragment calculated by an automatic integration method from an extracted ion chromatogram obtained by an LC-MS/MS analysis of the dephosphorylation reagent.

In formula (6), $X_6$ represents a peak area value of the sixth peptide fragment calculated by an automatic integration method from an extracted ion chromatogram obtained by an LC-MS/MS analysis of the dephosphorylation reagent.

In formula (7), $X_7$ represents a peak area value of the seventh peptide fragment calculated by an automatic integration method from an extracted ion chromatogram obtained by an LC-MS/MS analysis of the dephosphorylation reagent.

In formula (8), $X_8$ represents a peak area value of the eighth peptide fragment calculated by an automatic integration method from an extracted ion chromatogram obtained by an LC-MS/MS analysis of the dephosphorylation reagent.

In formula (9), $X_9$ represents a peak area value of the ninth peptide fragment calculated by an automatic integration method from an extracted ion chromatogram obtained by an LC-MS/MS analysis of the dephosphorylation reagent.

In formulas (A1) to (A3), (B1), (B2), (C1), (C2), (D1) to (D3) and (1) to (9), Y represents a peak area value of an alkaline phosphatase calculated by an automatic integration method from a chromatogram obtained by an LC-UV analysis of the dephosphorylation reagent. The "peak area value of an alkaline phosphatase" means, when the dephosphorylation reagent contains one alkaline phosphatase, a peak area value of the one alkaline phosphatase, and, when the dephosphorylation reagent contains two or more alkaline phosphatases, a total peak area value of the two or more alkaline phosphatases (i.e., total peak area value of all alkaline phosphatases contained in the dephosphorylation reagent).

The value of $(X_{A1}/Y) \times 100$ is not particularly limited as long as it is 5.0000 or less, and the smaller the value is, the more preferable it is. The value of $(X_{A1}/Y) \times 100$ is preferably 4.5000 or less, more preferably 4.0000 or less, and still more preferably 3.5000 or less. The lower limit of $(X_{A1}/Y) \times 100$ is a detection limit. In terms of obtaining an effect that matches an effort to decrease the value of $(X_{A1}/Y) \times 100$ (e.g., removal and separation of the peptide fragment group (A1) by purification), the value of $(X_{A1}/Y) \times 100$ is preferably 0.0800 or more, more preferably 0.1000 or more, and still more preferably 0.1500 or more.

The value of $(X_{A2}/Y) \times 100$ is not particularly limited as long as it is 2.4000 or less, and the smaller the value is, the more preferable it is. The value of $(X_{A2}/Y) \times 100$ is preferably 2.2000 or less, more preferably 2.0000 or less, and still more preferably 1.5000 or less. The lower limit of $(X_{A2}/Y) \times 100$ is a detection limit. In terms of obtaining an effect that matches an effort to decrease the value of $(X_{A2}/Y) \times 100$ (e.g., removal and separation of the peptide fragment group (A2) by purification), the value of $(X_{A2}/Y) \times 100$ is preferably 0.0800 or more, more preferably 0.1000 or more, and still more preferably 0.1500 or more.

The value of $(X_{A3}/Y) \times 100$ is not particularly limited as long as it is 4.5000 or less, and the smaller the value is, the more preferable it is. The value of $(X_{A3}/Y) \times 100$ is preferably 4.0000 or less, more preferably 3.0000 or less, and still more preferably 2.5000 or less. The lower limit of $(X_{A3}/Y) \times 100$ is a detection limit. In terms of obtaining an effect that matches an effort to decrease the value of $(X_{A3}/Y) \times 100$ (e.g., removal and separation of the peptide fragment group (A3) by purification), the value of $(X_{A3}/Y) \times 100$ is preferably 0.0800 or more, more preferably 0.1000 or more, and still more preferably 0.1500 or more.

The value of $(X_{B1}/Y) \times 100$ is not particularly limited as long as it is 0.6000 or less, and the smaller the value is, the more preferable it is. The value of $(X_{B1}/Y) \times 100$ is preferably 0.5000 or less, more preferably 0.3000 or less, and still more preferably 0.2000 or less. The lower limit of $(X_{B1}/Y) \times 100$ is a detection limit. In terms of obtaining an effect that matches an effort to decrease the value of $(X_{B1}/Y) \times 100$ (e.g., removal and separation of the peptide fragment group (B1) by purification), the value of $(X_{B1}/Y) \times 100$ is preferably 0.0500 or more, more preferably 0.0600 or more, and still more preferably 0.0700 or more.

The value of $(X_{B2}/Y) \times 100$ is not particularly limited as long as it is 0.6000 or less, and the smaller the value is, the more preferable it is. The value of $(X_{B2}/Y) \times 100$ is preferably 0.5000 or less, more preferably 0.3000 or less, and still more preferably 0.2000 or less. The lower limit of $(X_{B2}/Y) \times 100$ is a detection limit. In terms of obtaining an effect that matches an effort to decrease the value of $(X_{B2}/Y) \times 100$ (e.g., removal and separation of the peptide fragment group (B2) by purification), the value of $(X_{B2}/Y) \times 100$ is preferably 0.0500 or more, more preferably 0.0600 or more, and still more preferably 0.0700 or more.

The value of $(X_{C1}/Y) \times 100$ is not particularly limited as long as it is 0.1800 or less, and the smaller the value is, the more preferable it is. The value of $(X_{C1}/Y) \times 100$ is preferably 0.1500 or less, more preferably 0.1200 or less, and still more preferably 0.1000 or less. The lower limit of $(X_{C1}/Y) \times 100$ is a detection limit. In terms of obtaining an effect that matches an effort to decrease the value of $(X_{C1}/Y) \times 100$ (e.g., removal and separation of the peptide fragment group (C1) by purification), the value of $(X_{C1}/Y) \times 100$ is preferably 0.0500 or more, more preferably 0.0600 or more, and still more preferably 0.0700 or more.

The value of $(X_{C2}/Y) \times 100$ is not particularly limited as long as it is 0.1800 or less, and the smaller the value is, the more preferable it is. The value of $(X_{C2}/Y) \times 100$ is preferably 0.1500 or less, more preferably 0.1200 or less, and still more preferably 0.1000 or less. The lower limit of $(X_{C2}/Y) \times 100$ is a detection limit. In terms of obtaining an effect that matches an effort to decrease the value of $(X_{C2}/Y) \times 100$ (e.g., removal and separation of the peptide fragment group (C2) by purification), the value of $(X_{C2}/Y) \times 100$ is preferably 0.0500 or more, more preferably 0.0600 or more, and still more preferably 0.0700 or more.

The value of $(X_{D1}/Y) \times 100$ is not particularly limited as long as it is 4.4000 or less, and the smaller the value is, the more preferable it is. The value of $(X_{D1}/Y) \times 100$ is preferably 4.0000 or less, more preferably 3.5000 or less, and still more preferably 3.0000 or less. The lower limit of $(X_{A1}/Y) \times 100$ is a detection limit. In terms of obtaining an effect that matches an effort to decrease the value of $(X_{A1}/Y) \times 100$ (e.g., removal and separation of the peptide fragment group (D1) by purification), the value of $(X_{D1}/Y) \times 100$ is preferably 0.0800 or more, more preferably 0.1000 or more, and still more preferably 0.1500 or more.

The value of $(X_{D2}/Y) \times 100$ is not particularly limited as long as it is 3.4000 or less, and the smaller the value is, the more preferable it is. The value of $(X_{D2}/Y) \times 100$ is preferably 3.0000 or less, more preferably 2.8000 or less, and still more preferably 2.5000 or less. The lower limit of $(X_{D2}/Y) \times 100$ is a detection limit. In terms of obtaining an effect that matches an effort to decrease the value of $(X_{D2}/Y) \times 100$ (e.g., removal and separation of the peptide fragment group (D2) by purification), the value of $(X_{D2}/Y) \times 100$ is preferably 0.0800 or more, more preferably 0.1000 or more, and still more preferably 0.1500 or more.

The value of $(X_{D3}/Y) \times 100$ is not particularly limited as long as it is 1.0000 or less, and the smaller the value is, the more preferable it is. The value of $(X_{D3}/Y) \times 100$ is preferably 0.9000 or less, more preferably 0.8000 or less, and still more preferably 0.7000 or less. The lower limit of $(X_{D3}/Y) \times 100$ is a detection limit. In terms of obtaining an effect that matches an effort to decrease the value of $(X_{D3}/Y) \times 100$ (e.g., removal and separation of the peptide fragment group (D3) by purification), the value of $(X_{D3}/Y) \times 100$ is preferably 0.0800 or more, more preferably 0.1000 or more, and still more preferably 0.1500 or more.

The value of $(X_1/Y) \times 100$ is not particularly limited as long as it is 1.0000 or less, and the smaller the value is, the more preferable it is. The value of $(X_1/Y) \times 100$ is preferably 0.9000 or less, more preferably 0.8000 or less, and still more preferably 0.7000 or less. The lower limit of $(X_1/Y) \times 100$ is a detection limit. In terms of obtaining an effect that matches an effort to decrease the value of $(X_1/Y) \times 100$ (e.g., removal and separation of the first peptide fragment by purification), the value of $(X_1/Y) \times 100$ is preferably 0.0800 or more, more preferably 0.1000 or more, and still more preferably 0.1500 or more.

The value of $(X_2/Y) \times 100$ is not particularly limited as long as it is 0.8000 or less, and the smaller the value is, the more preferable it is. The value of $(X_2/Y) \times 100$ is preferably 0.7000 or less, more preferably 0.6000 or less, and still more preferably 0.5000 or less. The lower limit of $(X_2/Y) \times 100$ is a detection limit. In terms of obtaining an effect that matches an effort to decrease the value of $(X_2/Y) \times 100$ (e.g., removal and separation of the second peptide fragment by purification), the value of $(X_2/Y) \times 100$ is preferably 0.0800 or more, more preferably 0.1000 or more, and still more preferably 0.1500 or more.

The value of $(X_3/Y) \times 100$ is not particularly limited as long as it is 2.3000 or less, and the smaller the value is, the more preferable it is. The value of $(X_3/Y) \times 100$ is preferably 2.0000 or less, more preferably 1.5000 or less, and still more preferably 1.0000 or less. The lower limit of $(X_3/Y) \times 100$ is a detection limit. In terms of obtaining an effect that matches an effort to decrease the value of $(X_3/Y) \times 100$ (e.g., removal and separation of the third peptide fragment by purification), the value of $(X_3/Y) \times 100$ is preferably 0.1500 or more, more preferably 0.1000 or more, and still more preferably 0.0800 or more.

The value of $(X_4/Y) \times 100$ is not particularly limited as long as it is 0.6000 or less, and the smaller the value is, the more preferable it is. The value of $(X_4/Y) \times 100$ is preferably 0.5000 or less, more preferably 0.3000 or less, and still more preferably 0.2000 or less. The lower limit of $(X_4/Y) \times 100$ is a detection limit. In terms of obtaining an effect that matches an effort to decrease the value of $(X_4/Y) \times 100$ (e.g., removal and separation of the fourth peptide fragment by purification), the value of $(X_4/Y) \times 100$ is preferably 0.0500 or more, more preferably 0.0600 or more, and still more preferably 0.0700 or more.

The value of $(X_5/Y) \times 100$ is not particularly limited as long as it is 0.1800 or less, and the smaller the value is, the more preferable it is. The value of $(X_5/Y) \times 100$ is preferably 0.1500 or less, more preferably 0.1200 or less, and still more preferably 0.1000 or less. The lower limit of $(X_5/Y) \times 100$ is a detection limit. In terms of obtaining an effect that matches an effort to decrease the value of $(X_5/Y) \times 100$ (e.g., removal and separation of the fifth peptide fragment by purification), the value of $(X_5/Y) \times 100$ is preferably 0.0500 or more, more preferably 0.0600 or more, and still more preferably 0.0700 or more.

The value of $(X_6/Y) \times 100$ is not particularly limited as long as it is 1.0000 or less, and the smaller the value is, the more preferable it is. The value of $(X_6/Y) \times 100$ is preferably 0.9000 or less, more preferably 0.8000 or less, and still more preferably 0.7000 or less. The lower limit of $(X_6/Y) \times 100$ is a detection limit. In terms of obtaining an effect that matches an effort to decrease the value of $(X_6/Y) \times 100$ (e.g., removal and separation of the sixth peptide fragment by purification), the value of $(X_6/Y) \times 100$ is preferably 0.0500 or more, more preferably 0.0600 or more, and still more preferably 0.0700 or more.

The value of $(X_7/Y) \times 100$ is not particularly limited as long as it is 1.6000 or less, and the smaller the value is, the more preferable it is. The value of $(X_7/Y) \times 100$ is preferably 1.5000 or less, more preferably 1.2000 or less, and still more preferably 1.0000 or less. The lower limit of $(X_7/Y) \times 100$ is a detection limit. In terms of obtaining an effect that matches an effort to decrease the value of $(X_7/Y) \times 100$ (e.g., removal and separation of the seventh peptide fragment by purification), the value of $(X_7/Y) \times 100$ is preferably 0.0500 or more, more preferably 0.0600 or more, and still more preferably 0.0700 or more.

The value of $(X_8/Y) \times 100$ is not particularly limited as long as it is 0.2000 or less, and the smaller the value is, the more preferable it is. The value of $(X_8/Y) \times 100$ is preferably 0.1800 or less, more preferably 0.1700 or less, and still more preferably 0.1500 or less. The lower limit of $(X_8/Y) \times 100$ is a detection limit. In terms of obtaining an effect that matches an effort to decrease the value of $(X_8/Y) \times 100$ (e.g., removal and separation of the eighth peptide fragment by purification), the value of $(X_8/Y) \times 100$ is preferably 0.0500 or more, more preferably 0.0600 or more, and still more preferably 0.0700 or more.

The value of $(X_9/Y) \times 100$ is not particularly limited as long as it is 0.3500 or less, and the smaller the value is, the more preferable it is. The value of $(X_9/Y) \times 100$ is preferably 0.3200 or less, more preferably 0.3000 or less, and still more preferably 0.2800 or less. The lower limit of $(X_9/Y) \times 100$ is a detection limit. In terms of obtaining an effect that matches an effort to decrease the value of $(X_9/Y) \times 100$ (e.g., removal and separation of the ninth peptide fragment by purification), the value of $(X_9/Y) \times 100$ is preferably 0.0800 or more, more preferably 0.1000 or more, and still more preferably 0.1500 or more.

The smaller the peak area value of the peptide fragment group (A1), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (A1) is preferably 14,000 or less, more preferably 12,000 or less, and still more preferably 10,000 or less. The lower limit of the peak area value of the peptide fragment group (A1) is a detection limit. In terms of obtaining an effect that matches an effort to decrease the peak area value of the peptide fragment group (A1) (e.g., removal and separation of the peptide fragment group (A1) by purification), the peak area value of the peptide fragment group (A1) is preferably 600 or more, more preferably 800 or more, and still more preferably 1,000 or more.

The smaller the peak area value of the peptide fragment group (A2), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (A2) is preferably 6,000 or less, more preferably 5,000 or less, and still more preferably 4,000 or less. The lower limit of the peak area value of the peptide fragment group (A2) is a detection limit. In terms of obtaining an effect that matches an effort to decrease the peak area value of the peptide fragment group (A2) (e.g., removal and separation of the peptide fragment group (A2) by purification), the peak area value of the peptide fragment group (A2) is preferably 500 or more, more preferably 800 or more, and still more preferably 1,000 or more.

The smaller the peak area value of the peptide fragment group (A3), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (A3) is preferably 12,000 or less, more preferably 10,000 or less, and still more preferably 8,000 or less. The lower limit of the peak area value of the peptide fragment group (A3) is a detection limit. In terms of obtaining an effect that matches an effort to decrease the peak area value of the peptide fragment group (A3) (e.g., removal and separation of the peptide fragment group (A3) by purification), the peak area value of the peptide fragment group (A3) is preferably 500 or more, more preferably 800 or more, and still more preferably 1,000 or more.

The smaller the peak area value of the peptide fragment group (B1), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (B1) is preferably 1,500 or less, more preferably 1,200 or less, and still more preferably 1,000 or less. The lower limit of the peak area value of the peptide fragment group (B1) is a detection limit. In terms of obtaining an effect that matches an effort to decrease the peak area value of the peptide fragment group (B1) (e.g., removal and separation of the peptide fragment group (B1) by purification), the peak area value of the peptide fragment group (B1) is preferably 100 or more, more preferably 150 or more, and still more preferably 200 or more.

The smaller the peak area value of the peptide fragment group (B2), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (B2) is preferably 1,500 or less, more preferably 1,200 or less, and still more preferably 1,000 or less. The lower limit of the peak area value of the peptide fragment group (B2) is a detection limit. In terms of obtaining an effect that matches an effort to decrease the peak area value of the peptide fragment group (B2) (e.g., removal and separation of the peptide fragment group (B2) by purification), the peak area value of the peptide fragment group (B2) is preferably 100 or more, more preferably 150 or more, and still more preferably 200 or more.

The smaller the peak area value of the peptide fragment group (C1), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (C1) is preferably 400 or less, more preferably 380 or less, and still more preferably 350 or less. The lower limit of the peak area value of the peptide fragment group (C1) is a detection limit. In terms of obtaining an effect that matches an effort to decrease the peak area value of the peptide fragment group (C1) (e.g., removal and separation of the peptide fragment group (C1) by purification), the peak area value of the peptide fragment group (C1) is preferably 100 or more, more preferably 130 or more, and still more preferably 150 or more.

The smaller the peak area value of the peptide fragment group (C2), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (C2) is preferably 400 or less, more preferably 380 or less, and still more preferably 350 or less. The lower limit of the peak area value of the peptide fragment group (C2) is a detection limit. In terms of obtaining an effect that matches an effort to decrease the peak area value of the peptide fragment group (C2) (e.g., removal and separation of the peptide fragment group (C2) by purification), the peak area value of the peptide fragment group (C2) is preferably 100 or more, more preferably 130 or more, and still more preferably 150 or more.

The smaller the peak area value of the peptide fragment group (D1), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (D1) is preferably 10,000 or less, more preferably 8,000 or less, and still more preferably 7,000 or less. The lower limit of the peak area value of the peptide fragment group (D1) is a detection limit. In terms of obtaining an effect that matches an effort to decrease the peak area value of the peptide fragment group (D1) (e.g., removal and separation of the peptide fragment group (D1) by purification), the peak area value of the peptide fragment group (D1) is preferably 600 or more, more preferably 800 or more, and still more preferably 1,000 or more.

The smaller the peak area value of the peptide fragment group (D2), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (D2) is preferably 7,500 or less, more preferably 7,000 or less, and still more preferably 6,000 or less. The lower limit of the peak area value of the peptide fragment group (D2) is a detection limit. In terms of obtaining an effect that matches an effort to decrease the peak area value of the peptide fragment group (D2) (e.g., removal and separation of the peptide fragment group (D2) by purification), the peak area value of the peptide fragment group (D2) is preferably 500 or more, more preferably 600 or more, and still more preferably 800 or more.

The smaller the peak area value of the peptide fragment group (D3), which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the peptide fragment group (D3) is preferably 2,400 or less, more preferably 2,000 or less, and still more preferably 1,500 or less. The lower limit of the peak area value of the peptide fragment group (D3) is a detection limit. In terms of obtaining an effect that matches an effort to decrease the peak area value of the peptide fragment group (D3) (e.g., removal and separation of the peptide fragment group (D3) by purification), the peak area value of the peptide fragment group (D3) is preferably 200 or more, more preferably 300 or more, and still more preferably 400 or more.

The smaller the peak area value of the first peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the first peptide fragment is preferably 3,000 or less, more preferably 2,500 or less, and still more preferably 2,000 or less. The lower limit of the peak area value of the first peptide fragment is a detection limit. In terms of obtaining an effect that matches an effort to decrease the peak area value of the first peptide fragment (e.g., removal and separation of the first peptide fragment by purification), the peak area value of the first peptide fragment is preferably 500 or more, more preferably 800 or more, and still more preferably 1,000 or more.

The smaller the peak area value of the second peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the second peptide fragment is preferably 2,000 or less, more preferably 1,800 or less, and still more preferably 1,500 or less. The lower limit of the peak area value of the second peptide fragment is a detection limit. In terms of obtaining an effect that matches an effort to decrease the peak area value of the second peptide fragment (e.g., removal and separation of the second peptide fragment by purification), the peak area value of the second peptide fragment is preferably 500 or more, more preferably 800 or more, and still more preferably 1,000 or more.

The smaller the peak area value of the third peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the third peptide fragment is preferably 6,000 or less, more preferably 3,000 or less, and still more preferably 1,000 or less. The lower limit of the peak area value of the third peptide fragment is a detection limit. In terms of obtaining an effect that matches an effort to decrease the peak area value of the third peptide fragment (e.g., removal and separation of the third peptide fragment by purification), the peak area value of the third peptide fragment is preferably 500 or more, more preferably 800 or more, and still more preferably 1,000 or more.

The smaller the peak area value of the fourth peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the fourth peptide fragment is preferably 1,500 or less, more preferably 1,200 or less, and still more preferably 1,000 or less. The lower limit of the peak area value of the fourth peptide fragment is a detection limit. In terms of obtaining an effect that matches an effort to decrease the peak area value of the fourth peptide fragment (e.g., removal and separation of the fourth peptide fragment by purification), the peak area value of the fourth peptide fragment is preferably 100 or more, more preferably 150 or more, and still more preferably 200 or more.

The smaller the peak area value of the fifth peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the fifth peptide fragment is preferably 400 or less, more preferably 380 or less, and still more preferably 350 or less. The lower limit of the peak area value of the fifth peptide fragment is a detection limit. In terms of obtaining an effect that matches an effort to decrease the peak area value of the fifth peptide fragment (e.g., removal and separation of the fifth peptide fragment by purification), the peak area value of the fifth peptide fragment is preferably 100 or more, more preferably 130 or more, and still more preferably 150 or more.

The smaller the peak area value of the sixth peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the sixth peptide fragment is preferably 3,000 or less, more preferably 2,500 or less, and still more preferably 2,000 or less. The lower limit of the peak area value of the sixth peptide fragment is a detection limit. In terms of obtaining an effect that matches an effort to decrease the peak area value of the sixth peptide fragment (e.g., removal and separation of the sixth peptide fragment by purification), the peak area value of the sixth peptide fragment is preferably 100 or more, more preferably 150 or more, and still more preferably 200 or more.

The smaller the peak area value of the seventh peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the seventh peptide fragment is preferably 4,500 or less, more preferably 3,000 or less, and still more preferably 2,500 or less. The lower limit of the peak area value of the seventh peptide fragment is a detection limit. In terms of obtaining an effect that matches an effort to decrease the peak area value of the seventh peptide fragment (e.g., removal and separation of the seventh peptide fragment by purification), the peak area value of the seventh peptide fragment is preferably 100 or more, more preferably 150 or more, and still more preferably 200 or more.

The smaller the peak area value of the eighth peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the eighth peptide fragment is preferably 500 or less, more preferably 450 or less, and still more preferably 400 or less. The lower limit of the peak area value of the eighth peptide fragment is a detection limit. In terms of obtaining an effect that matches an effort to decrease the peak area value of the eighth peptide fragment (e.g., removal and separation of the eighth peptide fragment by purification), the peak area value of the eighth peptide fragment is preferably 100 or more, more preferably 150 or more, and still more preferably 200 or more.

The smaller the peak area value of the ninth peptide fragment, which is calculated by an automatic integration method from an extracted ion chromatogram obtained by an LC-MS/MS analysis performed by using an aqueous solution prepared from the dephosphorylation reagent and with an alkaline phosphatase concentration of 10% by weight, is, the more preferable it is. The peak area value of the ninth peptide fragment is preferably 1,000 or less, more preferably 900 or less, and still more preferably 800 or less. The lower limit of the peak area value of the ninth peptide fragment is a detection limit. In terms of obtaining an effect that matches an effort to decrease the peak area value of the ninth peptide fragment (e.g., removal and separation of the ninth peptide fragment by purification), the peak area value of the ninth peptide fragment is preferably 100 or more, more preferably 150 or more, and still more preferably 200 or more.

The peak area value of an alkaline phosphatase, which is calculated by an automatic integration method from a chromatogram obtained by an LC-UV analysis performed by using an aqueous solution prepared from the dephosphorylation reagent and with an alkaline phosphatase concentration of 10% by weight, is preferably 200,000 or more, more preferably 220,000 or more, and still more preferably 240,000 or more. The upper limit of the peak area value of an alkaline phosphatase is not particularly limited. The peak area value of an alkaline phosphatase is preferably 500,000 or less, more preferably 400,000 or less, and still more preferably 350,000 or less.

LC-MS/MS Analysis and LC-UV Analysis

An LC-MS/MS analysis and an LC-UV analysis will be described.

The LC-MS/MS analysis and the LC-UV analysis are performed by using a sample in which a ratio to be obtained is the same as that of the dephosphorylation reagent. The LC-MS/MS analysis and the LC-UV analysis can be performed, for example, by using an aqueous solution prepared from the dephosphorylation reagent and with an alkaline phosphatase concentration of 10% by weight.

The LC-MS/MS analysis is one of the hyphenated methods. The hyphenated method is a method of analyzing by connecting a chromatograph such as a gas chromatograph and a liquid chromatograph to a mass spectrometer. The LC-MS/MS analysis is a method of analyzing by connecting a liquid chromatograph (LC) to a tandem mass spectrometer (MS/MS). In the LC-MS/MS analysis, analyte components separated by the liquid chromatograph are ionized, the ions thus produced are separated by the tandem mass spectrometer, and specific mass ions are fragmented and detected.

In the hyphenated method, an extracted ion chromatogram is a chromatogram expressed as a function of time obtained by measuring a mass spectrum at a certain time interval and storing it in a computer, followed by reading a relative intensity at a specific (not necessarily one type) m/z value.

The m/z value of an ion of each peptide fragment constituting the peptide fragment group (A1) used for detecting a peak of each peptide fragment constituting the peptide fragment group (A1) is preferably 50 to 2,200, more preferably 200 to 1,500, and still more preferably 300 to 1,200. The same applies to the m/z value of an ion of each peptide fragment constituting the peptide fragment group (A2), the peptide fragment group (A3), the peptide fragment group (B1), the peptide fragment group (B2), the peptide fragment group (C1), the peptide fragment group (C2), the peptide fragment group (D1), the peptide fragment group (D2) or the peptide fragment group (D3).

The m/z value of an ion of the first peptide fragment is 920.7682, the m/z value of an ion of the second peptide fragment is 723.8572, the m/z value of an ion of the third peptide fragment is 786.8757, the m/z value of an ion of the fourth peptide fragment is 558.7676, the m/z value of an ion of the fifth peptide fragment is 443.7533, the m/z value of the sixth peptide fragment is 814.4018, the m/z value of the seventh peptide fragment is 655.8148, the m/z value of the eighth peptide fragment is 652.6623, and the m/z value of the ninth peptide fragment is 636.3282.

Regarding an ion of a peptide fragment with an m/z value being specified, it is possible to create an extracted ion chromatogram of the peptide fragment based on the m/z value. Regarding a peptide fragment with an m/z value not being specified, after whether a certain peak corresponds to a peak of a predetermined peptide fragment or not is confirmed by an amino acid sequence analysis of a peptide fragment showing the peak, it is possible to create an extracted ion chromatogram of the peptide fragment based on the m/z value of the peak.

The LC-UV analysis is a method of analyzing by connecting a liquid chromatograph (LC) to an ultraviolet detector (UV detector). In the LC-UV analysis, an alkaline phosphatase is detected as a component having absorption at 214 nm.

Specific Conditions of LC-MS/MS Analysis
  Specific conditions of the LC-MS/MS analysis are as follows.
Apparatus Configuration
  Mass spectrometer: maXis impact (manufactured by Bruker Daltnics, Inc.)
  Conditions of Mass Spectrometry
  Ionization method: ESI
  Measured ion: cation
  Capillary voltage: 4,500 V
  Nebulizer: 2.0 bar
  Dry gas: 8.0 L/min
  Detector voltage: 1,823 V
  Measuring span (MS): m/z 50 to 2,200
  MS/MS Conditions
  Measuring span (MS): m/z 50 to 2,200
  Collision gas: nitrogen
  Conditions of LC-UV Analysis
  Specific conditions of the LC-UV analysis are as follows.
  Apparatus Configuration
  Liquid chromatograph: LC-30A system (manufactured by Shimadzu Corporation)
  Detector: UV-Vis (190 to 900 nm, manufactured by Shimadzu Corporation)
  Conditions of Liquid Chromatography
  Column: Acquity BEH C18 1.7 μm (manufactured by Waters Corporation)
  Column size: 2.1 mm×100 mm
  Column temperature: 50° C.
  Mobile phase flow rate: 0.2 mL/min
  Mobile phase A: mixed solution of water/formic acid (1000:1)
  Mobile phase B: mixed solution of acetonitrile/water/formic acid (900:100:1)
  Injection volume: 20 μL Gradient program:

TABLE 1

| Time (min) | Mobile phase A (vol %) | Mobile phase B (vol %) |
|---|---|---|
| 0 | 100 | 0 |
| 10 | 100 | 0 |
| 40 | 35 | 65 |
| 40.1 | 0 | 100 |
| 50 | 0 | 100 |
| 50.1 | 100 | 0 |
| 60 | 100 | 0 |

First Example

As a first example, we provide a method of evaluating a quality of a dephosphorylation reagent.

A method according to the first example includes the steps of:
  (1-1) providing a dephosphorylation reagent containing an alkaline phosphatase and a peptide fragment derived from the alkaline phosphatase; and
  (1-2) evaluating the dephosphorylation reagent as having a high quality if a content ratio of the peptide fragment to the alkaline phosphatase is a predetermined reference value or less.

The step (1-1) and the step (1-2) are sequentially performed.

The step (1-1) is a step of providing a dephosphorylation reagent containing an alkaline phosphatase and a peptide fragment derived from the alkaline phosphatase.

In the method according to the first example, one or more peptide fragments derived from the alkaline phosphatase contained in the dephosphorylation reagent are used for quality evaluation. Whether the peptide fragments are derived from the alkaline phosphatase of the dephosphorylation reagent or not can be determined by analyzing the amino acid sequences of the alkaline phosphatase and the peptide fragments.

In one example, one peptide fragment derived from the alkaline phosphatase contained in the dephosphorylation reagent is used for quality evaluation. In another example, two or more peptide fragments (peptide fragment group) derived from the alkaline phosphatase contained in the dephosphorylation reagent are used for quality evaluation.

The dephosphorylation reagent may contain one or more peptide fragments not used for quality evaluation (the peptide fragments may or may not be derived from the alkaline phosphatase contained in the dephosphorylation reagent) other than one or more peptide fragments used for quality evaluation. The dephosphorylation reagent may contain one or more components other than a peptide fragment. Examples of the other components include aqueous vehicles such as water, metal salts such as a magnesium salt and a sodium salt, surfactants, organic acids, glycerin and the like.

The dephosphorylation reagent has an alkaline phosphatase specific activity of preferably 2,000 U/mg or more, more preferably 2,500 U/mg or more, and still more preferably 3,000 U/mg or more. The alkaline phosphatase specific activity of the dephosphorylation reagent is measured as follows. By measuring the absorbance at 405 nm derived from p-nitrophenol produced by adding an alkaline phosphatase to an aqueous solution of p-nitrophenylphosphate, it is possible to calculate the specific activity of the alkaline phosphatase.

In one example, the dephosphorylation reagent contains the peptide fragment group (A1). The dephosphorylation reagent may contain one or more peptide fragments derived from the alkaline phosphatase contained in the dephosphorylation reagent other than the peptide fragment group (A1). Preferably, the peptide fragment group (A1) contains one, two or three peptide fragments selected from the group consisting of the first to third peptide fragments.

In the example in which the dephosphorylation reagent contains the peptide fragment group (A1), the dephosphorylation reagent contains an alkaline phosphatase that can generate the peptide fragment group (A1). Preferably, the alkaline phosphatase that can generate the peptide fragment group (A1) is selected from the alkaline phosphatases (a) and (b1). In this example, the dephosphorylation reagent contains one or two or more alkaline phosphatases selected from the alkaline phosphatases (a) and (b1).

In one example, the dephosphorylation reagent contains the peptide fragment group (A2). The dephosphorylation reagent may contain one or more peptide fragments derived from the alkaline phosphatase contained in the dephosphorylation reagent other than the peptide fragment group (A2). Preferably, the peptide fragment group (A2) contains one or two peptide fragments selected from the group consisting of the first and second peptide fragments.

In the example in which the dephosphorylation reagent contains the peptide fragment group (A2), the dephosphorylation reagent contains an alkaline phosphatase that can generate the peptide fragment group (A2). Preferably, the alkaline phosphatase that can generate the peptide fragment group (A2) is selected from the alkaline phosphatases (a) and (b1). In this example, the dephosphorylation reagent contains one or two or more alkaline phosphatases selected from the alkaline phosphatases (a) and (b1).

In one example, the dephosphorylation reagent contains the peptide fragment group (A3). The dephosphorylation reagent may contain one or more peptide fragments derived from the alkaline phosphatase contained in the dephosphorylation reagent other than the peptide fragment group (A3). Preferably, the peptide fragment group (A3) contains one or two peptide fragments selected from the group consisting of the first and third peptide fragments.

In the example in which the dephosphorylation reagent contains the peptide fragment group (A3), the dephosphorylation reagent contains an alkaline phosphatase that can generate the peptide fragment group (A3). Preferably, the alkaline phosphatase that can generate the peptide fragment group (A3) is selected from the alkaline phosphatases (a) and (b1). In this example, the dephosphorylation reagent contains one or two or more alkaline phosphatases selected from the alkaline phosphatases (a) and (b1).

In one example, the dephosphorylation reagent contains the second peptide fragment. The dephosphorylation reagent may contain one or more peptide fragments derived from the alkaline phosphatase contained in the dephosphorylation reagent other than the second peptide fragment. Preferably, the dephosphorylation reagent further contains one or two peptide fragments selected from the group consisting of the first and third peptide fragments.

In the example in which the dephosphorylation reagent contains the second peptide fragment, the dephosphorylation reagent contains an alkaline phosphatase that can generate the second peptide fragment. Preferably, the alkaline phosphatase that can generate the second peptide fragment is selected from the alkaline phosphatases (a) and (b1). In this example, the dephosphorylation reagent contains one or two or more alkaline phosphatases selected from the alkaline phosphatases (a) and (b1).

In one example, the dephosphorylation reagent contains the peptide fragment group (B1). The dephosphorylation reagent may contain one or more peptide fragments derived from the alkaline phosphatase contained in the dephosphorylation reagent other than the peptide fragment group (B1). Preferably, the peptide fragment group (B1) contains the fourth peptide fragment.

In the example in which the dephosphorylation reagent contains the peptide fragment group (B1), the dephosphorylation reagent contains an alkaline phosphatase that can generate the peptide fragment group (B1). Preferably, the alkaline phosphatase that can generate the peptide fragment group (B1) is selected from the alkaline phosphatases (a) and (b2). In this example, the dephosphorylation reagent contains one or two or more alkaline phosphatases selected from the alkaline phosphatases (a) and (b2).

In one example, the dephosphorylation reagent contains the peptide fragment group (B2). The dephosphorylation reagent may contain one or more peptide fragments derived from the alkaline phosphatase contained in the dephosphorylation reagent other than the peptide fragment group (B2). Preferably, the peptide fragment group (B2) contains the fourth peptide fragment.

In the example in which the dephosphorylation reagent contains the peptide fragment group (B2), the dephosphorylation reagent contains an alkaline phosphatase that can generate the peptide fragment group (B2). Preferably, the alkaline phosphatase that can generate the peptide fragment group (B2) is selected from the alkaline phosphatases (a) and (b2). In this example, the dephosphorylation reagent contains one or two or more alkaline phosphatases selected from the alkaline phosphatases (a) and (b2).

In one example, the dephosphorylation reagent contains the fourth peptide fragment. The dephosphorylation reagent may contain one or more peptide fragments derived from the alkaline phosphatase contained in the dephosphorylation reagent other than the fourth peptide fragment.

In the example in which the dephosphorylation reagent contains the fourth peptide fragment, the dephosphorylation reagent contains an alkaline phosphatase that can generate the fourth peptide fragment. Preferably, the alkaline phosphatase that can generate the fourth peptide fragment is selected from the alkaline phosphatases (a) and (b2). In this example, the dephosphorylation reagent contains one or two or more alkaline phosphatases selected from the alkaline phosphatases (a) and (b2).

In one example, the dephosphorylation reagent contains the peptide fragment group (C1). The dephosphorylation reagent may contain one or more peptide fragments derived from the alkaline phosphatase contained in the dephosphorylation reagent other than the peptide fragment group (C1). Preferably, the peptide fragment group (C1) contains the fifth peptide fragment.

In the example in which the dephosphorylation reagent contains the peptide fragment group (C1), the dephosphorylation reagent contains an alkaline phosphatase that can generate the peptide fragment group (C1). Preferably, the alkaline phosphatase that can generate the peptide fragment group (C1) is selected from the alkaline phosphatases (a) and (b3). In this example, the dephosphorylation reagent contains one or two or more alkaline phosphatases selected from the alkaline phosphatases (a) and (b3).

In one example, the dephosphorylation reagent contains the peptide fragment group (C2). The dephosphorylation reagent may contain one or more peptide fragments derived from the alkaline phosphatase contained in the dephosphorylation reagent other than the peptide fragment group (C2). Preferably, the peptide fragment group (C2) contains the fifth peptide fragment.

In the example in which the dephosphorylation reagent contains the peptide fragment group (C2), the dephosphorylation reagent contains an alkaline phosphatase that can generate the peptide fragment group (C2). Preferably, the alkaline phosphatase that can generate the peptide fragment group (C2) is selected from the alkaline phosphatases (a) and (b3). In this example, the dephosphorylation reagent contains one or two or more alkaline phosphatases selected from the alkaline phosphatases (a) and (b3).

In one example, the dephosphorylation reagent contains the fifth peptide fragment. The dephosphorylation reagent may contain one or more peptide fragments derived from the alkaline phosphatase contained in the dephosphorylation reagent other than the fifth peptide fragment.

In the example in which the dephosphorylation reagent contains the fifth peptide fragment, the dephosphorylation reagent contains an alkaline phosphatase that can generate the fifth peptide fragment. Preferably, the alkaline phosphatase that can generate the fifth peptide fragment is selected from the alkaline phosphatases (a) and (b3). In this example, the dephosphorylation reagent contains one or two or more alkaline phosphatases selected from the alkaline phosphatases (a) and (b3).

In one example, the dephosphorylation reagent contains the peptide fragment group (D1). The dephosphorylation reagent may contain one or more peptide fragments derived from the alkaline phosphatase contained in the dephosphorylation reagent other than the peptide fragment group (D1). Preferably, the peptide fragment group (D1) contains one, two, three or four peptide fragments selected from the group consisting of the sixth to ninth peptide fragments.

In the example in which the dephosphorylation reagent contains the peptide fragment group (D1), the dephosphorylation reagent contains an alkaline phosphatase that can generate the peptide fragment group (D1). Preferably, the alkaline phosphatase that can generate the peptide fragment group (D1) is selected from the alkaline phosphatases (a) and (b4). In this example, the dephosphorylation reagent contains one or two or more alkaline phosphatases selected from the alkaline phosphatases (a) and (b4).

In one example, the dephosphorylation reagent contains the peptide fragment group (D2). The dephosphorylation reagent may contain one or more peptide fragments derived from the alkaline phosphatase contained in the dephosphorylation reagent other than the peptide fragment group (D2). Preferably, the peptide fragment group (D2) contains one or two peptide fragments selected from the group consisting of the sixth and seventh peptide fragments.

In the example in which the dephosphorylation reagent contains the peptide fragment group (D2), the dephosphorylation reagent contains an alkaline phosphatase that can generate the peptide fragment group (D2). Preferably, the alkaline phosphatase that can generate the peptide fragment group (D2) is selected from the alkaline phosphatases (a) and (b4). In this example, the dephosphorylation reagent contains one or two or more alkaline phosphatases selected from the alkaline phosphatases (a) and (b4).

In one example, the dephosphorylation reagent contains the peptide fragment group (D3). The dephosphorylation reagent may contain one or more peptide fragments derived from the alkaline phosphatase contained in the dephosphorylation reagent other than the peptide fragment group (D3). Preferably, the peptide fragment group (D3) contains one or two peptide fragments selected from the group consisting of the eighth and ninth peptide fragments.

In the example in which the dephosphorylation reagent contains the peptide fragment group (D3), the dephosphorylation reagent contains an alkaline phosphatase that can generate the peptide fragment group (D3). Preferably, the alkaline phosphatase that can generate the peptide fragment group (D3) is selected from the alkaline phosphatases (a) and (b4). In this example, the dephosphorylation reagent contains one or two or more alkaline phosphatases selected from the alkaline phosphatases (a) and (b4).

In one example, the dephosphorylation reagent contains the seventh peptide fragment. The dephosphorylation reagent may contain one or more peptide fragments derived from the alkaline phosphatase contained in the dephosphorylation reagent other than the seventh peptide fragment. Preferably, the dephosphorylation reagent further contains one, two or three peptide fragments selected from the sixth, eighth and ninth peptide fragments.

In the example in which the dephosphorylation reagent contains the seventh peptide fragment, the dephosphorylation reagent contains an alkaline phosphatase that can generate the seventh peptide fragment. Preferably, the alkaline phosphatase that can generate the seventh peptide fragment is selected from the alkaline phosphatases (a) and (b4). In this example, the dephosphorylation reagent contains one or two or more alkaline phosphatases selected from the alkaline phosphatases (a) and (b4).

In one example, the dephosphorylation reagent contains the eighth peptide fragment. The dephosphorylation reagent may contain one or more peptide fragments derived from the alkaline phosphatase contained in the dephosphorylation reagent other than the eighth peptide fragment. Preferably, the dephosphorylation reagent further contains one, two or three peptide fragments selected from the sixth, seventh and ninth peptide fragments.

In the example in which the dephosphorylation reagent contains the eighth peptide fragment, the dephosphorylation reagent contains an alkaline phosphatase that can generate the eighth peptide fragment. Preferably, the alkaline phosphatase that can generate the eighth peptide fragment is selected from the alkaline phosphatases (a) and (b4). In this example, the dephosphorylation reagent contains one or two or more alkaline phosphatases selected from the alkaline phosphatases (a) and (b4).

In one example, the dephosphorylation reagent contains the ninth peptide fragment. The dephosphorylation reagent may contain one or more peptide fragments derived from the alkaline phosphatase contained in the dephosphorylation reagent other than the ninth peptide fragment. Preferably, the dephosphorylation reagent further contains one, two or three peptide fragments selected from the sixth, seventh and eighth peptide fragments.

In the example in which the dephosphorylation reagent contains the ninth peptide fragment, the dephosphorylation reagent contains an alkaline phosphatase that can generate the ninth peptide fragment. Preferably, the alkaline phosphatase that can generate the ninth peptide fragment is selected from the alkaline phosphatases (a) and (b4). In this example, the dephosphorylation reagent contains one or two or more alkaline phosphatases selected from the alkaline phosphatases (a) and (b4).

In one example, the dephosphorylation reagent contains the second, fourth, fifth, seventh, eighth and ninth peptide fragments. The dephosphorylation reagent may contain one or more peptide fragments derived from the alkaline phosphatase contained in the dephosphorylation reagent other than the second, fourth, fifth, seventh, eighth and ninth peptide fragments. Preferably, the dephosphorylation reagent further contains one, two or three peptide fragments selected from the first, third and sixth peptide fragments.

In an example in which the dephosphorylation reagent contains the second, fourth, fifth, seventh, eighth and ninth peptide fragments, the dephosphorylation reagent contains an alkaline phosphatase that can generate the second, fourth, fifth, seventh, eighth and ninth peptide fragments. Preferably, the alkaline phosphatase that can generate the second, fourth, fifth, seventh, eighth and ninth peptide fragments is selected from the alkaline phosphatases (a) and (b5). In this example, the dephosphorylation reagent contains one or two or more alkaline phosphatases selected from the alkaline phosphatases (a) and (b5). Preferably, the alkaline phosphatase (b5) contains one or two or more selected from the group consisting of positions 91 to 109, positions 93 to 105 and positions 529 to 531 of the amino acid sequence set forth in SEQ ID NO: 10. In the example in which the alkaline phosphatase (b5) contains one or two or more selected from the group consisting of positions 91 to 109, positions 93 to 105 and positions 529 to 531 of the amino acid sequence set forth in SEQ ID NO: 10, the alkaline phosphatase can generate one, two or three peptide fragments selected from the first, third and sixth peptide fragments. Further preferably, the alkaline phosphatase (b5) contains positions 91 to 109 and positions 529 to 531 of the amino acid sequence set forth in SEQ ID NO: 10. In the example in which the alkaline phosphatase (b5) contains positions 91 to 109 and positions 529 to 531 of the amino acid sequence set forth in SEQ ID NO: 10, the alkaline phosphatase can generate three peptide fragments of the first, third and sixth peptide fragments.

The dephosphorylation reagent provided in the step (1-1) may be a dephosphorylation reagent that has been subjected in advance to treatment that reduces the content(s) of one or more of the following impurities:
the peptide fragment group (A1);
the peptide fragment group (A2);
the peptide fragment group (A3);
the peptide fragment group (B1);
the peptide fragment group (B2);
the peptide fragment group (C1);
the peptide fragment group (C2);
the peptide fragment group (D1);
the peptide fragment group (D2);
the peptide fragment group (D3);
the second peptide fragment (preferably, the second peptide fragment, and one or two peptide fragments selected from the group consisting of the first and third peptide fragments);
the fourth peptide fragment;
the fifth peptide fragment;
the seventh peptide fragment (preferably, the seventh peptide fragment, and one, two or three peptide fragments selected from the group consisting of the sixth, eighth and ninth peptide fragments);
the eighth peptide fragment (preferably, the eighth peptide fragment, and one, two or three peptide fragments selected from the group consisting of the sixth, seventh and ninth peptide fragments);
the ninth peptide fragment (preferably, the ninth peptide fragment, and one, two or three peptide fragments selected from the group consisting of the sixth, seventh and eighth peptide fragments); and
the second, fourth, fifth, seventh, eighth and ninth peptide fragments (preferably, the second, fourth, fifth, seventh, eighth and ninth peptide fragments, and one, two or three peptide fragments selected from the group consisting of the first, third and sixth peptide fragments).

For example, by separating one or more of the abovementioned impurities from an alkaline phosphatase extract from an organ of a bovine, a shrimp and the like, an alkaline phosphatase extract from a microorganism into which a gene encoding an alkaline phosphatase has been introduced, a bacterial cell homogenate of a microorganism into which a gene encoding an alkaline phosphatase has been introduced, a commercially available alkaline phosphatase product and the like, it is possible to reduce the content(s) of one or more of the abovementioned impurities. Examples of the separation method include dialysis, salting out, gel filtration, ultrafiltration, membrane separation, ion exchange, column chromatography, electrophoresis and the like. One separation method may be used alone, or two or more separation methods may be used in combination. For example, by purifying a commercially available alkaline phosphatase product by column chromatography and the like, it is possible to reduce the content(s) of one or more of the abovementioned impurities to a desired range. The column chromatography is, for example, liquid chromatography. The column and the mobile phase used in liquid chromatography is not particularly limited as long as one or more of the abovementioned impurities can be separated, and it is preferable to use a C18-supported reverse-phase column.

The step (1-2) is a step of evaluating the dephosphorylation reagent as having a high quality if the content ratio of the peptide fragment group to the alkaline phosphatase is a predetermined reference value or less.

The content of the alkaline phosphatase in the dephosphorylation reagent can be measured in accordance with a known method. The content of the alkaline phosphatase in the dephosphorylation reagent can be measured as an amount reflecting the content of the alkaline phosphatase. Examples of the amount reflecting the content of the alkaline phosphatase include a peak area value of the alkaline phosphatase calculated from a chromatogram obtained by an LC-UV analysis. By using a calibration curve showing a relationship between the content of the alkaline phosphatase and the peak area of the alkaline phosphatase, it is possible to obtain the content of the alkaline phosphatase in the dephosphorylation reagent from the peak area value of the alkaline phosphatase.

The content of the peptide fragment in the dephosphorylation reagent can be measured in accordance with a known method. The content of the peptide fragment in the dephosphorylation reagent can be measured as an amount reflecting the content of the peptide fragment. Examples of the amount reflecting the content of the peptide fragment include a peak area value of the peptide fragment calculated from an extracted ion chromatogram obtained by an LC-MS/MS analysis. By using a calibration curve showing a relationship between the content of the peptide fragment and the peak area of the peptide fragment, it is possible to obtain the content of the peptide fragment in the dephosphorylation reagent from the peak area value of the peptide fragment.

The predetermined reference value can be appropriately determined according to the type of the peptide fragment.

In an example in which the dephosphorylation reagent contains the peptide fragment group (A1), the dephosphorylation reagent can be evaluated as having a high quality if the content ratio of the peptide fragment group (A1) to the alkaline phosphatase satisfies formula (A1).

In an example in which the peptide fragment group (A1) contains the first peptide fragment, the dephosphorylation reagent can be evaluated as having a high quality if the content ratio of the peptide fragment group (A1) to the alkaline phosphatase satisfies formula (A1) and the content ratio of the first peptide fragment to the alkaline phosphatase satisfies formula (1).

In an example in which the peptide fragment group (A1) contains the second peptide fragment, the dephosphorylation reagent can be evaluated as having a high quality if the content ratio of the peptide fragment group (A1) to the alkaline phosphatase satisfies formula (A1) and the content ratio of the second peptide fragment to the alkaline phosphatase satisfies formula (2).

In an example in which the peptide fragment group (A1) contains the third peptide fragment, the dephosphorylation reagent can be evaluated as having a high quality if the content ratio of the peptide fragment group (A1) to the alkaline phosphatase satisfies formula (A1) and the content ratio of the third peptide fragment to the alkaline phosphatase satisfies formula (3).

In an example in which the peptide fragment group (A1) contains two or more peptide fragments selected from the group consisting of the first, second and third peptide fragments, the dephosphorylation reagent can be evaluated as having a high quality if the content ratio of the peptide fragment group (A1) to the alkaline phosphatase satisfies formula (A1) and the content ratios of the selected two or more peptide fragments to the alkaline phosphatase satisfy the above predetermined formulas, respectively.

In an example in which the dephosphorylation reagent contains the peptide fragment group (A2), the dephosphorylation reagent can be evaluated as having a high quality if the content ratio of the peptide fragment group (A2) to the alkaline phosphatase satisfies formula (A2).

In an example in which the peptide fragment group (A2) contains the first peptide fragment, the dephosphorylation reagent can be evaluated as having a high quality if the content ratio of the peptide fragment group (A2) to the alkaline phosphatase satisfies formula (A2) and the content ratio of the first peptide fragment to the alkaline phosphatase satisfies formula (1).

In an example in which the peptide fragment group (A2) contains the second peptide fragment, the dephosphorylation reagent can be evaluated as having a high quality if the content ratio of the peptide fragment group (A2) to the alkaline phosphatase satisfies formula (A2) and the content ratio of the second peptide fragment to the alkaline phosphatase satisfies formula (2).

In an example in which the peptide fragment group (A2) contains the first and second peptide fragments, the dephosphorylation reagent can be evaluated as having a high quality if the content ratio of the peptide fragment group (A2) to the alkaline phosphatase satisfies formula (A2) and the content ratios of the first and second peptide fragments to the alkaline phosphatase satisfy formulas (1) and (2), respectively.

In an example in which the dephosphorylation reagent contains the peptide fragment group (A3), the dephosphorylation reagent can be evaluated as having a high quality if the content ratio of the peptide fragment group (A3) to the alkaline phosphatase satisfies formula (A3).

In an example in which the peptide fragment group (A3) contains the first peptide fragment, the dephosphorylation reagent can be evaluated as having a high quality if the content ratio of the peptide fragment group (A3) to the alkaline phosphatase satisfies formula (A3) and the content ratio of the first peptide fragment to the alkaline phosphatase satisfies formula (1).

In an example in which the peptide fragment group (A3) contains the third peptide fragment, the dephosphorylation reagent can be evaluated as having a high quality if the content ratio of the peptide fragment group (A3) to the alkaline phosphatase satisfies formula (A3) and the content ratio of the third peptide fragment to the alkaline phosphatase satisfies formula (3).

In an example in which the peptide fragment group (A3) contains the first and third peptide fragments, the dephosphorylation reagent can be evaluated as having a high quality if the content ratio of the peptide fragment group (A3) to the alkaline phosphatase satisfies formula (A3) and the content ratios of the first and third peptide fragments to the alkaline phosphatase satisfy formulas (1) and (3), respectively.

In an example in which the dephosphorylation reagent contains the second peptide fragment, the dephosphorylation reagent can be evaluated as having a high quality if the content ratio of the second peptide fragment to the alkaline phosphatase satisfies formula (2).

In an example in which the dephosphorylation reagent contains the first and second peptide fragments, the dephosphorylation reagent can be evaluated as having a high quality if the content ratio of the second peptide fragment to the alkaline phosphatase satisfies formula (2) and the content ratio of the first peptide fragment to the alkaline phosphatase satisfies formula (1).

In an example in which the dephosphorylation reagent contains the second and third peptide fragments, the dephosphorylation reagent can be evaluated as having a high quality if the content ratio of the second peptide fragment to the alkaline phosphatase satisfies formula (2) and the content ratio of the third peptide fragment to the alkaline phosphatase satisfies formula (3).

In an example in which the dephosphorylation reagent contains the first, second and third peptide fragments, the dephosphorylation reagent can be evaluated as having a high quality if the content ratio of the second peptide fragment to the alkaline phosphatase satisfies formula (2) and the content ratios of the first and third peptide fragments to the alkaline phosphatase satisfy formulas (1) and (3), respectively.

In an example in which the dephosphorylation reagent contains the peptide fragment group (B1), the dephosphorylation reagent can be evaluated as having a high quality if the content ratio of the peptide fragment group (B1) to the alkaline phosphatase satisfies formula (B1).

In an example in which the peptide fragment group (B1) contains the fourth peptide fragment, the dephosphorylation reagent can be evaluated as having a high quality if the content ratio of the peptide fragment group (B1) to the alkaline phosphatase satisfies formula (B1) and the content ratio of the fourth peptide fragment to the alkaline phosphatase satisfies formula (4).

In an example in which the dephosphorylation reagent contains the peptide fragment group (B2), the dephosphorylation reagent can be evaluated as having a high quality if the content ratio of the peptide fragment group (B2) to the alkaline phosphatase satisfies formula (B2).

In an example in which the peptide fragment group (B2) contains the fourth peptide fragment, the dephosphorylation reagent can be evaluated as having a high quality if the content ratio of the peptide fragment group (B2) to the alkaline phosphatase satisfies formula (B2) and the content ratio of the fourth peptide fragment to the alkaline phosphatase satisfies formula (4).

In an example in which the dephosphorylation reagent contains the fourth peptide fragment, the dephosphorylation reagent can be evaluated as having a high quality if the content ratio of the fourth peptide fragment to the alkaline phosphatase satisfies formula (4).

In an example in which the dephosphorylation reagent contains the peptide fragment group (C1), the dephosphorylation reagent can be evaluated as having a high quality if the content ratio of the peptide fragment group (C1) to the alkaline phosphatase satisfies formula (C1).

In an example in which the peptide fragment group (C1) contains the fifth peptide fragment, the dephosphorylation reagent can be evaluated as having a high quality if the content ratio of the peptide fragment group (C1) to the alkaline phosphatase satisfies formula (C1) and the content ratio of the fifth peptide fragment to the alkaline phosphatase satisfies formula (5).

In an example in which the dephosphorylation reagent contains the peptide fragment group (C2), the dephosphorylation reagent can be evaluated as having a high quality if the content ratio of the peptide fragment group (C2) to the alkaline phosphatase satisfies formula (C2).

In an example in which the peptide fragment group (C2) contains the fifth peptide fragment, the dephosphorylation reagent can be evaluated as having a high quality if the content ratio of the peptide fragment group (C2) to the alkaline phosphatase satisfies formula (C2) and the content ratio of the fifth peptide fragment to the alkaline phosphatase satisfies formula (5).

In an example in which the dephosphorylation reagent contains the fifth peptide fragment, the dephosphorylation reagent can be evaluated as having a high quality if the content ratio of the fifth peptide fragment to the alkaline phosphatase satisfies formula (5).

In an example in which the dephosphorylation reagent contains the peptide fragment group (D1), the dephosphorylation reagent can be evaluated as having a high quality if the content ratio of the peptide fragment group (D1) to the alkaline phosphatase satisfies formula (D1).

In an example in which the peptide fragment group (D1) contains the sixth peptide fragment, the dephosphorylation reagent can be evaluated as having a high quality if the content ratio of the peptide fragment group (D1) to the alkaline phosphatase satisfies formula (D1) and the content ratio of the sixth peptide fragment to the alkaline phosphatase satisfies formula (6).

In an example in which the peptide fragment group (D1) contains the seventh peptide fragment, the dephosphorylation reagent can be evaluated as having a high quality if the content ratio of the peptide fragment group (D1) to the alkaline phosphatase satisfies formula (D1) and the content ratio of the seventh peptide fragment to the alkaline phosphatase satisfies formula (7).

In an example in which the peptide fragment group (D1) contains the eighth peptide fragment, the dephosphorylation reagent can be evaluated as having a high quality if the content ratio of the peptide fragment group (D1) to the alkaline phosphatase satisfies formula (D1) and the content ratio of the eighth peptide fragment to the alkaline phosphatase satisfies formula (8).

In an example in which the peptide fragment group (D1) contains the ninth peptide fragment, the dephosphorylation reagent can be evaluated as having a high quality if the content ratio of the peptide fragment group (D1) to the alkaline phosphatase satisfies formula (D1) and the content ratio of the ninth peptide fragment to the alkaline phosphatase satisfies formula (9).

In an example in which the dephosphorylation reagent contains two or more peptide fragments selected from the group consisting of the sixth, seventh, eighth and ninth peptide fragments, the dephosphorylation reagent can be evaluated as having a high quality if the content ratio of the peptide fragment group (D1) to the alkaline phosphatase satisfies formula (D1) and the content ratios of the selected two or more peptide fragments to the alkaline phosphatase satisfy the above predetermined formulas, respectively.

In an example in which the dephosphorylation reagent contains the peptide fragment group (D2), the dephosphorylation reagent can be evaluated as having a high quality if the content ratio of the peptide fragment group (D2) to the alkaline phosphatase satisfies formula (D2).

In an example in which the peptide fragment group (D2) contains the sixth peptide fragment, the dephosphorylation reagent can be evaluated as having a high quality if the content ratio of the peptide fragment group (D2) to the alkaline phosphatase satisfies formula (D2) and the content ratio of the sixth peptide fragment to the alkaline phosphatase satisfies formula (6).

In an example in which the peptide fragment group (D2) contains the seventh peptide fragment, the dephosphorylation reagent can be evaluated as having a high quality if the content ratio of the peptide fragment group (D2) to the alkaline phosphatase satisfies formula (D2) and the content ratio of the seventh peptide fragment to the alkaline phosphatase satisfies formula (7).

In an example in which the peptide fragment group (D2) contains the sixth and seventh peptide fragments, the dephosphorylation reagent can be evaluated as having a high quality if the content ratio of the peptide fragment group (D2) to the alkaline phosphatase satisfies formula (D2) and the content ratios of the sixth and seventh peptide fragments to the alkaline phosphatase satisfy formulas (6) and (7), respectively.

In an example in which the dephosphorylation reagent contains the peptide fragment group (D3), the dephosphorylation reagent can be evaluated as having a high quality if the content ratio of the peptide fragment group (D3) to the alkaline phosphatase satisfies formula (D3).

In an example in which the peptide fragment group (D3) contains the eighth peptide fragment, the dephosphorylation reagent can be evaluated as having a high quality if the content ratio of the peptide fragment group (D3) to the alkaline phosphatase satisfies formula (D3) and the content ratio of the eighth peptide fragment to the alkaline phosphatase satisfies formula (8).

In an example in which the peptide fragment group (D3) contains the ninth peptide fragment, the dephosphorylation reagent can be evaluated as having a high quality if the content ratio of the peptide fragment group (D3) to the alkaline phosphatase satisfies formula (D3) and the content ratio of the ninth peptide fragment to the alkaline phosphatase satisfies formula (9).

In an example in which the peptide fragment group (D3) contains the eighth and ninth peptide fragments, the dephosphorylation reagent can be evaluated as having a high quality if the content ratio of the peptide fragment group (D3) to the alkaline phosphatase satisfies formula (D3) and the content ratios of the eighth and ninth peptide fragments to the alkaline phosphatase satisfy formulas (8) and (9), respectively.

In an example in which the dephosphorylation reagent contains the seventh peptide fragment, the dephosphorylation reagent can be evaluated as having a high quality if the content ratio of the seventh peptide fragment to the alkaline phosphatase satisfies formula (7).

In an example in which the dephosphorylation reagent contains the sixth and seventh peptide fragments, the dephosphorylation reagent can be evaluated as having a high quality if the content ratio of the seventh peptide fragment to the alkaline phosphatase satisfies formula (7) and the content ratio of the sixth peptide fragment to the alkaline phosphatase satisfies formula (6).

In an example in which the dephosphorylation reagent contains the seventh and eighth peptide fragments, the dephosphorylation reagent can be evaluated as having a high quality if the content ratio of the seventh peptide fragment to the alkaline phosphatase satisfies formula (7) and the content ratio of the eighth peptide fragment to the alkaline phosphatase satisfies formula (8).

In an example in which the dephosphorylation reagent contains the seventh and ninth peptide fragments, the dephosphorylation reagent can be evaluated as having a high quality if the content ratio of the seventh peptide fragment to the alkaline phosphatase satisfies formula (7) and the content ratio of the ninth peptide fragment to the alkaline phosphatase satisfies formula (9).

In an example in which the dephosphorylation reagent contains the seventh peptide fragment and two or more peptide fragments selected from the group consisting of the sixth, eighth and ninth peptide fragments, the dephosphorylation reagent can be evaluated as having a high quality if the content ratio of the seventh peptide fragment to the alkaline phosphatase satisfies formula (7) and the content ratios of the two or more peptide fragments to the alkaline phosphatase satisfy the above predetermined formulas, respectively.

In an example in which the dephosphorylation reagent contains the eighth peptide fragment, the dephosphorylation reagent can be evaluated as having a high quality if the content ratio of the eighth peptide fragment to the alkaline phosphatase satisfies formula (8).

In an example in which the dephosphorylation reagent contains the sixth and eighth peptide fragments, the dephosphorylation reagent can be evaluated as having a high quality if the content ratio of the eighth peptide fragment to the alkaline phosphatase satisfies formula (8) and the content ratio of the sixth peptide fragment to the alkaline phosphatase satisfies formula (6).

In an example in which the dephosphorylation reagent contains the seventh and eighth peptide fragments, the dephosphorylation reagent can be evaluated as having a high quality if the content ratio of the eighth peptide fragment to the alkaline phosphatase satisfies formula (8) and the content ratio of the seventh peptide fragment to the alkaline phosphatase satisfies formula (7).

In an example in which the dephosphorylation reagent contains the eighth and ninth peptide fragments, the dephosphorylation reagent can be evaluated as having a high quality if the content ratio of the eighth peptide fragment to the alkaline phosphatase satisfies formula (8) and the content ratio of the ninth peptide fragment to the alkaline phosphatase satisfies formula (9).

In an example in which the dephosphorylation reagent contains the eighth peptide fragment and two or more peptide fragments selected from the group consisting of the sixth, seventh and ninth peptide fragments, the dephosphorylation reagent can be evaluated as having a high quality if the content ratio of the eighth peptide fragment to the alkaline phosphatase satisfies formula (8) and the content ratios of the selected two or more peptide fragments to the alkaline phosphatase satisfy the above predetermined formulas, respectively.

In an example in which the dephosphorylation reagent contains the ninth peptide fragment, the dephosphorylation reagent can be evaluated as having a high quality if the content ratio of the ninth peptide fragment to the alkaline phosphatase satisfies formula (9).

In an example in which the dephosphorylation reagent contains the sixth and ninth peptide fragments, the dephosphorylation reagent can be evaluated as having a high quality if the content ratio of the ninth peptide fragment to the alkaline phosphatase satisfies formula (9) and the content ratio of the sixth peptide fragment to the alkaline phosphatase satisfies formula (6).

In an example in which the dephosphorylation reagent contains the seventh and ninth peptide fragments, the dephosphorylation reagent can be evaluated as having a high quality if the content ratio of the alkaline phosphatase satisfies formula (9) and the content ratio of the seventh peptide fragment to the alkaline phosphatase satisfies formula (7).

In an example in which the dephosphorylation reagent contains the eighth and ninth peptide fragments, the dephosphorylation reagent can be evaluated as having a high quality if the content ratio of the ninth peptide fragment to the alkaline phosphatase satisfies formula (9) and the content ratio of the eighth peptide fragment to the alkaline phosphatase satisfies formula (8).

In an example in which the dephosphorylation reagent contains the ninth peptide fragment and two or more peptide fragments selected from the group consisting of the sixth, seventh and eighth peptide fragments, the dephosphorylation reagent can be evaluated as having a high quality if the content ratio of the ninth peptide fragment to the alkaline phosphatase satisfies formula (9) and the content ratios of the selected two or more peptide fragments to the alkaline phosphatase satisfy the above predetermined formulas, respectively.

In an example in which the dephosphorylation reagent contains the second, fourth, fifth, seventh, eighth and ninth peptide fragments, the dephosphorylation reagent can be evaluated as having a high quality if the content ratios of the second, fourth, fifth, seventh, eighth and ninth peptide fragments to the alkaline phosphatase satisfy formulas (2), (4), (5), (7), (8) and (9), respectively.

In an example in which the dephosphorylation reagent contains the second, fourth, fifth, seventh, eighth and ninth peptide fragments and the first peptide fragment, the dephosphorylation reagent can be evaluated as having a high quality if the content ratios of the second, fourth, fifth, seventh, eighth and ninth peptide fragments to the alkaline phosphatase satisfy formulas (2), (4), (5), (7), (8) and (9), respectively, and the content ratio of the first peptide fragment to the alkaline phosphatase satisfies formula (1).

In an example in which the dephosphorylation reagent contains the second, fourth, fifth, seventh, eighth and ninth peptide fragments and the third peptide fragment, the dephosphorylation reagent can be evaluated as having a high quality if the content ratios of the second, fourth, fifth, seventh, eighth and ninth peptide fragments to the alkaline phosphatase satisfy formulas (2), (4), (5), (7), (8) and (9), respectively, and the content ratio of the third peptide fragment to the alkaline phosphatase satisfies formula (3).

In an example in which the dephosphorylation reagent contains the second, fourth, fifth, seventh, eighth and ninth peptide fragments and the sixth peptide fragment, the dephosphorylation reagent can be evaluated as having a high quality if the content ratios of the second, fourth, fifth, seventh, eighth and ninth peptide fragments to the alkaline phosphatase satisfy formulas (2), (4), (5), (7), (8) and (9), respectively, and the content ratio of the sixth peptide fragment to the alkaline phosphatase satisfies formula (6).

In an example in which the dephosphorylation reagent contains the second, fourth, fifth, seventh, eighth and ninth peptide fragments and two or more peptide fragments selected from the group consisting of the first, third and sixth peptide fragments, the dephosphorylation reagent can be evaluated as having a high quality if the content ratios of the second, fourth, fifth, seventh, eighth and ninth peptide fragments to the alkaline phosphatase satisfy formulas (2), (4), (5), (7), (8) and (9), respectively, and the content ratios of the selected two or more peptide fragments to the alkaline phosphatase satisfy the above predetermined formulas, respectively.

In step (1-2), the dephosphorylation reagent that has been evaluated as not having a high quality may be subjected to treatment that reduces the content(s) of one or more of the abovementioned impurities so that the quality is evaluated as high in accordance with the abovementioned reference(s). As a result, it is possible to obtain a dephosphorylation reagent that is evaluated as having a high quality in accordance with the abovementioned reference(s).

For example, by separating one or more of the abovementioned impurities from the dephosphorylation reagent that has been evaluated as not having a high quality, it is possible to reduce the content(s) of one or more of the abovementioned impurities. Examples of the separation method include dialysis, salting out, gel filtration, ultrafiltration, membrane separation, ion exchange, column chromatography, electrophoresis and the like. One separation method may be used alone, or two or more separation methods may be used in combination. For example, by purifying a commercially available alkaline phosphatase product by column chromatography and the like, it is possible to reduce the content(s) of one or more of the abovementioned impurities to a desired range. The column chromatography is, for example, liquid chromatography. The column and the mobile phase used in liquid chromatography is not particularly limited as long as one or more of the abovementioned impurities can be separated, and it is preferable to use a C18-supported reverse-phase column.

Second Example

A method according to a second example relates to a method of detecting a target nucleic acid. When quantitative determination of a target nucleic acid is performed, detection of the target nucleic acid is also necessarily performed. Thus, the method according to the second example also encompasses detection of the target nucleic acid in association with quantitative determination of the target nucleic acid. Quantitative determination of the target nucleic acid can be performed, for example, based on the intensity of the detected target nucleic acid (e.g., intensity of the detected labeling substance).

A method according to the second example includes the steps of:
(2-1) providing a sample containing a target nucleic acid;
(2-2) providing a dephosphorylation reagent containing an alkaline phosphatase and a peptide fragment derived from the alkaline phosphatase;
(2-3) treating the sample with the dephosphorylation reagent to dephosphorylate the target nucleic acid;
(2-4) labeling the dephosphorylated target nucleic acid; and
(2-5) detecting the labeled target nucleic acid.

The order of the steps (2-1) and (2-2) is not particularly limited, and the step (2-1) may be performed before the step (2-2) or may be performed after the step (2-2). The steps (2-3), (2-4) and (2-5) are sequentially performed after the steps (2-1) (2-2).

The step (2-1) is a step of providing a sample containing a target nucleic acid.

The target nucleic acid is a nucleic acid to be detected, and is appropriately determined according to an object of detecting the target nucleic acid and the like. Examples of the object of detecting the target nucleic acid include detection of viruses, detection of bacteria, detection of fungi, detection of single nucleotide polymorphism (SNP), detection of mRNA, detection of miRNA, comparative genomic hybridization (CGH), copy number variation, detection of deletion/duplication/fusion of genomic DNA sequences, detection of deletion/duplication/fusion of transcription products and the like.

Examples of the target nucleic acid include nucleic acids such as DNA, RNA, peptide nucleic acid (PNA) and locked nucleic acid (LNA) or a nucleic acid derivative. Examples of the nucleic acid derivative include a nucleic acid derivative containing a modified nucleotide (e.g., a nucleotide that has undergone reconstitution of a nucleotide or base containing a halogen group, an alkyl group such as a methyl group, an alkoxy group such as a methoxy group, a thio group and a carboxymethyl group and the like, saturation of a double bond, deamination, substitution of an oxygen molecule with a sulfur molecule and the like). The target nucleic acid may be single-stranded or double-stranded. Examples of the DNA include chromosomal DNA, viral DNA, DNA of a bacterium, a fungus and the like, cDNA, fragments thereof and the like. Examples of the RNA include mRNA, rRNA, small RNA, fragments thereof and the like. The target nucleic acid may be chemically synthesized DNA, RNA and the like. Specific examples of the target nucleic acid include a gene of a pathogen, a virus and the like, or a part thereof, a causative gene for genetic disease or a part thereof and the like.

The sample containing the target nucleic acid can be prepared by extracting a nucleic acid by a conventional method from, for example, a biomaterial, a virus, a bacterium, a fungus, a food and drink and the like. Examples of the biomaterial include body fluids such as blood, serum, plasma, urine, stool, spinal fluid, saliva, swab and tissue fluid, a cell, a tissue and the like. The biomaterial may be animal-derived or plant-derived.

The sample may contain a component other than the target nucleic acid. The sample may contain a nucleic acid other than the target nucleic acid. When the sample is prepared, at least a part of the component other than the target nucleic acid may be removed or may not be removed.

The content of the target nucleic acid in the sample is not particularly limited as long as the target nucleic acid can be detected. For example, by performing a nucleic acid amplification method such as PCR, by using the target nucleic acid as a template, it is possible to amplify the target nucleic acid. In other words, the sample may contain an amplification product of the target nucleic acid. This enables improvement in the detection sensitivity of the target nucleic acid.

The length (number of bases) of the target nucleic acid contained in the sample is not particularly limited. The length of the target nucleic acid is usually 10 to 300 bases, preferably 10 to 100 bases, and more preferably 15 to 100 bases. The length of the target nucleic acid can be appropriately adjusted by fragmentation treatment. The length of the target nucleic acid is, for example, a length at which the target nucleic acid can be hybridized with a probe. When the target nucleic acid is long (e.g., 1,500 bases or more, particularly 4,000 bases or more), it is preferable to perform fragmentation treatment of the target nucleic acid and to adjust the length of the target nucleic acid to an appropriate length. When fragmentation treatment is performed, it is not necessarily that a specific nucleic acid fragment is selected from the generated nucleic acid fragments, and the fragmentation product can be used as it is.

Examples of a method of cleaving the target nucleic acid for fragmentation include a method of cleaving by irradiation with ultrasonic waves, a method of cleaving with an enzyme, a method of cleaving with a restriction enzyme, a method using a nebulizer, a method of cleaving with an acid or an alkali and the like. In the method of cleaving with ultrasonic waves, by controlling the output intensity and the irradiation time of the ultrasonic waves with which the target nucleic acid is irradiated, it is possible to cleavage the target nucleic acid into a desired length.

The step (2-2) is a step of providing a dephosphorylation reagent containing an alkaline phosphatase and a peptide fragment group derived from the alkaline phosphatase.

The dephosphorylation reagent provided in the step (2-2) is a dephosphorylation reagent that has been evaluated as having a high quality by the method according to the first example.

Even a dephosphorylation reagent that has been evaluated as not having a high quality by the method according to the first example can be used as the dephosphorylation reagent provided in the step (2-2) after being subjected to treatment that reduces the content(s) of one or more of the abovementioned impurities so that the quality is evaluated as high in accordance with the abovementioned reference(s).

For example, by separating one or more of the abovementioned impurities from the dephosphorylation reagent that has been evaluated as not having a high quality, it is possible to reduce the content(s) of one or more of the abovementioned impurities. Examples of the separation method include dialysis, salting out, gel filtration, ultrafiltration, membrane separation, ion exchange, column chromatography, electrophoresis and the like. One separation method may be used alone, or two or more separation methods may be used in combination. For example, by purifying a commercially available alkaline phosphatase product by column chromatography and the like, it is possible to reduce the content(s) of one or more of the abovementioned impurities to a desired range. The column chromatography is, for example, liquid chromatography. The column and the mobile phase used in liquid chromatography is not particularly limited as long as one or more of the abovementioned impurities can be separated, and it is preferable to use a C18-supported reverse-phase column.

The step (2-3) is a step of treating the sample with the dephosphorylation reagent to dephosphorylate the target nucleic acid.

By treating the sample with the dephosphorylation reagent, the 5' end and/or the 3' end of the target nucleic acid is/are dephosphorylated. When a nucleic acid other than the target nucleic acid is contained in the sample, the 5' end and/or the 3' end of the nucleic acid other than the target nucleic acid is/are also dephosphorylated.

The reaction conditions when the target nucleic acid is dephosphorylated can be appropriately adjusted. The reaction time is usually 10 to 60 minutes, and preferably 20 to 50 minutes. The reaction temperature is usually 20 to 60° C., and preferably 25 to 45° C. The reaction is usually performed in an aqueous vehicle such as water.

One or more of the abovementioned impurities coexisting in the alkaline phosphatase have a possibility of adversely influencing when the nucleic acid is dephosphorylated by the alkaline phosphatase.

In this regard, in the dephosphorylation reagent that has been evaluated as having a high quality by the method according to the first example, the content ratio(s) of one or more of the abovementioned impurities to the alkaline phosphatase satisfies/satisfy the above predetermined formula(s). In other words, in the dephosphorylation reagent that has been evaluated as having a high quality by the method according to the first example, the relative content(s) of one or more of the abovementioned impurities has/have been reduced. Therefore, by using the dephosphorylation reagent that has been evaluated as having a high quality by the method according to the first example, it is possible to reduce the adverse influence of one or more of the abovementioned impurities that can occur when the nucleic acid is dephosphorylated by the alkaline phosphatase, thus enabling improvement in the dephosphorylation efficiency of the nucleic acid.

The step (2-4) is a step of labeling the dephosphorylated target nucleic acid.

The dephosphorylated target nucleic acid has a 5' end and/or a 3' end, each of which has been dephosphorylated by the alkaline phosphatase. By binding a labeling substance to the dephosphorylated 5' end and/or 3' end, it is possible to label the target nucleic acid. When a nucleic acid other than the target nucleic acid is contained in the sample, the nucleic acid other than the labeled nucleic acid is also labeled.

As the labeling substance, for example, a fluorescent dye, a fluorescent protein, a chemiluminescent body, a metal complex, a metal fine particle, biotin, a radioisotope and the like, can be used. The reaction conditions when the target nucleic acid is labeled can be appropriately adjusted according to the type of the labeling substance. When the labeling substance is a fluorescent dye, the fluorescent dye can be detected by using a fluorescence microscope, a fluorescence scanner and the like.

Examples of the fluorescent dye include organic fluorescent dyes such as a fluorescein-based dye, a rhodamine-based dye, an Alexa Fluor (manufactured by Invitrogen)-based dye, a BODIPY (manufactured by Invitrogen)-based dye, a cascade-based dye, a coumarin-based dye, an eosin-based dye, an NBD-based dye, a pyrene-based dye, a Texas Red-based dye and a cyanine-based dye.

Specific examples of the organic fluorescent dye include 5-carboxy-fluorescein, 6-carboxy-fluorescein, 5,6-dicarboxy-fluorescein, 6-carboxy-2',4,4',5',7,7'-hexachloro-fluorescein, 6-carboxy-2',4,7,7'-tetrachloro-fluorescein, 6-carboxy-4',5'-dichloro-2',7'-dimethoxy-fluorescein, naphthofluorescein, 5-carboxy-rhodamine, 6-carboxy-rhodamine, 5,6-dicarboxy-rhodamine, rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all of which are manufactured by Invitrogen), methoxycoumarin, eosin, NBD, pyrene, Cy5, Cy5.5, Cy7 and the like.

One or more of the abovementioned impurities coexisting in the alkaline phosphatase have a possibility of adversely influencing when the labeling substance is bound to the dephosphorylated nucleic acid.

In this regard, in the dephosphorylation reagent that has been evaluated as having a high quality by the method according to the first example, the content ratio(s) of one or more of the abovementioned impurities to the alkaline phosphatase satisfies/satisfy the above predetermined formula(s). In other words, in the dephosphorylation reagent that has been evaluated as having a high quality by the method according to the first example, the relative content(s) of one or more of the abovementioned impurities has/have been reduced. Therefore, by using the dephosphorylation reagent that has been evaluated as having a high quality by the method according to the first example, it is possible to reduce the adverse influence of the abovementioned impurities that can occur when the labeling substance is bound to the dephosphorylated nucleic acid, thus enabling improvement in the labeling efficiency of the dephosphorylated nucleic acid. Particularly, when $^{32}P$ is used as the labeling substance, this effect is remarkable.

The step (2-5) is a step of detecting the labeled target nucleic acid.

The target nucleic acid is detected by using the labeling substance bound to the target nucleic acid as an index. In other words, the target nucleic acid is detected by detecting the labeling substance bound to the target nucleic acid. A method of detecting the labeling substance is not particularly limited, and can be appropriately selected from known methods according to the type of the labeling substance. Quantitative determination of the target nucleic acid can also be performed based on the detected signal (e.g., intensity of the detected labeling substance).

The target nucleic acid can be detected, for example, by using the hybridization method. In the hybridization method, the target nucleic acid can be detected by using a probe that can be hybridized with the target nucleic acid. In one example of the nucleic acid detection method using a probe, the labeled target nucleic acid is brought into contact with a probe that can be hybridized with the target nucleic acid, and the target nucleic acid hybridized with the probe can be detected by using the labeling substance bound to the target nucleic acid as an index. When a nucleic acid other than the target nucleic acid is contained in the sample, it is preferable that, after the target nucleic acid is brought into contact with the probe, the nucleic acid that has not been hybridized with the probe is removed by washing or the like.

The reaction conditions when the target nucleic acid is hybridized with the probe can be appropriately adjusted according to chain length of the target nucleic acid, the chain length of the probe and the like. The reaction time is usually 30 to 1,200 minutes, and preferably 60 to 360 minutes. The reaction temperature is usually 25 to 60° C., and preferably 30 to 40° C. The reaction is usually performed in an aqueous vehicle such as water.

The amount of the target nucleic acid or probe used is not particularly limited as long as the hybridization between the target nucleic acid and the probe can occur and the labeling substance bound to the target nucleic acid can be detected, and the amount can be appropriately adjusted according to the chain length of the target nucleic acid, the chain length of the probe, the type of the labeling substance and the like.

As the probe, for example, nucleic acids such as DNA, RNA, peptide nucleic acid (PNA) and locked nucleic acid (LNA) or a nucleic acid derivative can be used. Examples of the nucleic acid derivative include a nucleic acid derivative containing a modified nucleotide (e.g., a nucleotide that has undergone reconstitution of a nucleotide or base containing a halogen group, an alkyl group such as a methyl group, an alkoxy group such as a methoxy group, a thio group and a carboxymethyl group and the like, saturation of a double bond, deamination, substitution of an oxygen molecule with a sulfur molecule and the like).

The probe has a base sequence complementary to at least a part of the base sequence of the target nucleic acid, and can be hybridized with the target nucleic acid. When the target nucleic acid is double-stranded, the probe may be hybridized with a sense strand or may be hybridized with an antisense strand. The base sequence of the probe may be complementary to any part of the base sequence of the target nucleic acid, and is preferably complementary to a highly-specific part of the base sequence of the target nucleic acid. In other words, the base sequence of the probe is preferably complementary to a base sequence which other nucleic acids contained in the sample do not have, of the base sequence of the target nucleic acid.

Of the base sequence of the probe, the length (number of bases) of the part complementary to the base sequence of the target nucleic acid is not particularly limited, and is usually 10 to 150 bases, preferably 20 to 100 bases, and more preferably 20 to 70 bases. The probe may be composed of a base sequence complementary to the base sequence of the target nucleic acid, or may include a base sequence not complementary to the base sequence of the target nucleic acid. The full length (total number of bases) of the probe is usually 10 to 300 bases, preferably 20 to 200 bases, and more preferably 15 to 100 bases.

The probe may be any of a commercially available product, a synthetic product, a prepared product from a living body and the like. A nucleic acid having a length of up to 200 bases, which is referred to as an oligonucleic acid, can be easily artificially synthesized with a synthesizer.

The probe is preferably fixed to a support. In other words, in a preferred example, the nucleic acid detection method is a nucleic acid detection method using a nucleic acid microarray. The nucleic acid microarray has a support and a plurality of probes fixed to the surface of the support. In the nucleic acid detection method using a nucleic acid microarray, the labeled target nucleic acid is brought into contact with a nucleic acid microarray provided with a probe that can be hybridized with the target nucleic acid, and the target nucleic acid hybridized with the probe can be detected by using the labeling substance bound to the target nucleic acid as an index. When a nucleic acid other than the target nucleic acid is contained in the sample, it is preferable that, after the target nucleic acid is brought into contact with the nucleic acid microarray, the nucleic acid that has not been hybridized with the probe on the nucleic acid microarray is removed by washing or the like. By using a nucleic acid microarray provided with a plurality of probes, two or more target nucleic acids can be simultaneously detected.

The support is not particularly limited as long as it can fix the probe. Examples of the support include a slide, a membrane, a bead and the like. Examples of the material of the support include inorganic materials such as glass, ceramic and silicon, and polymers such as polyethylene terephthalate, cellulose acetate, polycarbonate, polystyrene, polymethyl methacrylate and silicone rubber and the like.

Fixation of the probe to the support can be performed in accordance with a conventional method. As a method of fixing the probe to the support, a method of synthesizing an oligonucleic acid on the top surface of the support, a method of adding dropwise an oligonucleic acid synthesized in advance to the top surface of the support to fix and the like, are known. Examples of the former method include the method of U.S. Pat. No. 5,705,610 A, the method of U.S. Pat. No. 7,037,659 A and the like. In those methods, since an organic solvent is used during DNA synthesis reaction, the support is desirably a material that is resistant to an organic solvent. For example, it is possible to use a glass support having an irregular structure fabricated by using the method disclosed in JP H10-503841 A. Particularly, in the method of U.S. Pat. No. 7,037,659 A, since the back of the support is irradiated with light to control DNA synthesis, the support is preferably a material having translucency. Examples of the latter method include the method of JP 3922454 B2, a method using a glass capillary and the like. As an example of the glass capillary, it is possible to use a self-made glass capillary, commercially available products such as a micropipette (manufactured by Micro Support Co., Ltd.; MP-005) and the like.

As a method of detecting the target nucleic acid, the sandwich hybridization method can be used. In the sandwich hybridization method, a first probe (capture probe) fixed to the support and a second probe (detection probe) not fixed to the support are used. The capture probe and the detection probe each have a base sequence complementary to different parts of the target nucleic acid, and can be hybridized with different parts of the target nucleic acid. The target nucleic acid is hybridized with the detection probe and the capture probe, thus forming a complex. By detecting a labeling substance contained in this complex, the target nucleic acid can be detected.

The sequence identity between the base sequence of the detection probe and the base sequence of the capture probe is preferably low. The sequence identity is preferably 20% or less, and more preferably 10% or less. In this regard, the identity between two base sequences is a numerical value obtained by aligning two sequences (inserting a gap, if necessary) so that bases are matched as many as possible, and then by dividing the number of matched bases by total number of bases (the higher number of bases when the number of bases of two base sequences is different), and the identity can be easily calculated with commercially available software such as FASTA and BLAST (also provided via the internet).

The signal detected in the method of detecting the target nucleic acid (e.g., intensity of the detected labeling substance) is compared with a surrounding noise. Specifically, the signal value obtained from a position on the support at which a probe is fixed is compared with the signal value (noise value) obtained from a position of the support at which no probe is fixed, and a ratio of the former numerical value to the noise value is defined as an S/N ratio. The detection accuracy can be represented by the S/N ratio. In other words, the larger the S/N ratio is, the higher the detection accuracy is, and the smaller the S/N ratio is, the lower the detection accuracy is.

One or more of the abovementioned impurities coexisting in the alkaline phosphatase have a possibility of adversely influencing the detection sensitivity of the target nucleic acid. In this regard, in the dephosphorylation reagent that has been evaluated as having a high quality by the method according to the first example, the content ratio(s) of one or more of the abovementioned impurities to the alkaline phosphatase satisfies/satisfy the above predetermined formula(s). In other words, in the dephosphorylation reagent that has been evaluated as having a high quality by the method according to the first example, the relative content(s) of one or more of the abovementioned impurities has/have been reduced. Therefore, by using the dephosphorylation reagent that has been evaluated as having a high quality by the method according to the first example, it is possible to reduce the adverse influence of one or more of the abovementioned impurities on the detection sensitivity of the target nucleic acid, thus enabling improvement in the detection sensitivity of the target nucleic acid. This effect is remarkable in a nucleic acid detection method using an extremely small amount (preferably 5 to 1,000 µL, more preferably 5 to 500 µL) of a sample, for example, a nucleic acid detection method using a nucleic acid microarray.

EXAMPLES

Our methods will be described in detail by way of Examples, but this disclosure is not limited to the following Examples.

Conditions of LC-MS/MS Analysis

Conditions of the LC-MS/MS analysis used in Examples and Comparative Examples were as follows.

Apparatus Configuration

Mass spectrometer: maXis impact (manufactured by Bruker Daltnics, Inc.)

Conditions of Mass Spectrometry

Ionization method: ESI

Measured ion: cation

Capillary voltage: 4,500 V

Nebulizer: 2.0 bar

Dry gas: 8.0 L/min

Detector voltage: 1,823 V

Measuring span (MS): m/z 50 to 2,200

MS/MS Conditions

Measuring span (MS): m/z 50 to 2,200

Collision gas: nitrogen

Conditions of LC-UV Analysis

Conditions of the LC-UV analysis used in Examples and Comparative Examples were as follows.

Apparatus Configuration

Liquid chromatograph: LC-30A system (manufactured by Shimadzu Corporation)

Detector: UV-Vis (190 to 900 nm, manufactured by Shimadzu Corporation)

Conditions of Liquid Chromatography

Column: Acquity BEH C18 1.7 µm (manufactured by Waters Corporation)

Column size: 2.1 mm×100 mm

Column temperature: 50° C.

Mobile phase flow rate: 0.2 mL/min

Mobile phase A: mixed solution of water/formic acid (1000:1)

Mobile phase B: mixed solution of acetonitrile/water/formic acid (900:100:1)

Injection volume: 20 µL

Gradient program:

TABLE 2

| Time (min) | Mobile phase A (vol %) | Mobile phase B (vol %) |
|---|---|---|
| 0 | 100 | 0 |
| 10 | 100 | 0 |
| 40 | 35 | 65 |
| 40.1 | 0 | 100 |
| 50 | 0 | 100 |
| 50.1 | 100 | 0 |
| 60 | 100 | 0 |

Nucleic Acid Detection Method

The nucleic acid detection method used in Examples and Comparative Examples was as follows.

Detection of a nucleic acid was performed by using a DNA chip (DNA microarray). Specifically, detection was performed by using "3D-Gene" human miRNA oligo chip (compatible with miRBase release 21) manufactured by Toray Industries, Inc.

Comparative Examples 1 to 8

Eight alkaline phosphatase products purchased from five companies (hereinafter referred to as "composition C1" to "composition C8") were used as the alkaline phosphatase compositions of Comparative Examples 1 to 8. The alkaline phosphatase contained in each of the compositions C1 to C8 was an alkaline phosphatase derived from the intestinal tract of a bovine. When the alkaline phosphatase specific activities of the compositions C1 to C8 were measured, they were 2,238 U/mg for the composition C1, 2,492 U/mg for the composition C2, 2,431 U/mg for the composition C3, 2,519 U/mg for the composition C4, 2,411 U/mg for the composition C5, 2,552 U/mg for the composition C6, 2,448 U/mg for the composition C7, and 2,490 U/mg for the composition C8. The alkaline phosphatase specific activities were measured by a method using p-nitrophenylphosphate. Specifically, the method was as follows.

The following solutions A and B were provided.
Solution A: 1M diethanolamine buffer (pH 9.8)
Solution B: aqueous 0.67M p-nitrophenolphosphate solution 2.9 mL of the solution A and 0.1 mL of the solution B were prepared in a cuvette (optical path length=1 cm), and warmed at 37° C. for 5 minutes. Then, 0.1 mL of an aqueous alkaline phosphatase solution was added, and the absorbance change at 405 nm (37° C.) was measured with a spectrophotometer for 3 to 5 minutes to obtain an absorbance change per unit time (ΔOD). By using as a control, a sample to which water was added in place of the aqueous alkaline phosphatase solution, the absorbance change was obtained (ΔOD blank). The alkaline phosphatase activity (U/mL) was calculated from the following formula:

Alkaline phosphatase activity(U/mL)=(ΔOD−ΔOD blank)×3.1/(18.2×0.1×1.0).

The concentration of the alkaline phosphatase in the aqueous alkaline phosphatase solution was calculated by measuring the absorbance at 214 nm. The aqueous alkaline phosphatase solution was diluted with distilled water so that the absorbance at 214 nm became 0.1 to 1.0, and 1 Abs was approximated to 1 mg/mL, and then the value obtained by multiplying by the dilution rate was regarded as the concentration of the alkaline phosphatase. The specific activity represents an activity (U/mg) per 1 mg of the alkaline phosphatase, and was calculated by the abovementioned measurement method.

An aqueous 10% by weight alkaline phosphatase solution was prepared from each of the compositions C1 to C8, and by using this aqueous solution, an LC-UV analysis and an LC-MS/MS analysis were performed. Based on the extracted ion chromatogram obtained by the LC-MS/MS analysis, the peak area value of each of the first peptide fragment consisting of the amino acid sequence set forth in SEQ ID NO: 1 (EAEAEFLIPAEEENPAFWNRQAAQ), the second peptide fragment consisting of the amino acid sequence set forth in SEQ ID NO: 2 (EGVSLEKREAEAE), and the third peptide fragment consisting of the amino acid sequence set forth in SEQ ID NO: 3 (IPAEEENPAFWNR), the fourth peptide fragment consisting of the amino acid sequence set forth in SEQ ID NO: 4 (DRQVPDSAGTA), the fifth peptide fragment consisting of the amino acid sequence set forth in SEQ ID NO: 5 (APGKALDSK), the sixth peptide fragment consisting of the amino acid sequence set forth in SEQ ID NO: 6 (VPLASETHGGEDVAVF), the seventh peptide fragment consisting of the amino acid sequence set forth in SEQ ID NO: 7 (VPLASETHGGEDV), the eighth peptide fragment consisting of the amino acid sequence set forth in SEQ ID NO: 8 (GPQAHLVHGVQEETFVAH), and the ninth peptide fragment consisting of the amino acid sequence set forth in SEQ ID NO: 9 (GPQAHLVHGVQE) was calculated by an automatic integration method. Based on the chromatogram obtained by the LC-UV analysis, the peak area value of the alkaline phosphatase was calculated by an automatic integration method. In the LC-UV analysis, the alkaline phosphatase was detected as a component having absorption at 214 nm.

FIG. 1 shows an extracted ion chromatogram on the first peptide fragment obtained by an LC-MS/MS analysis of the composition C2 in Comparative Example 2.

Figure 2:
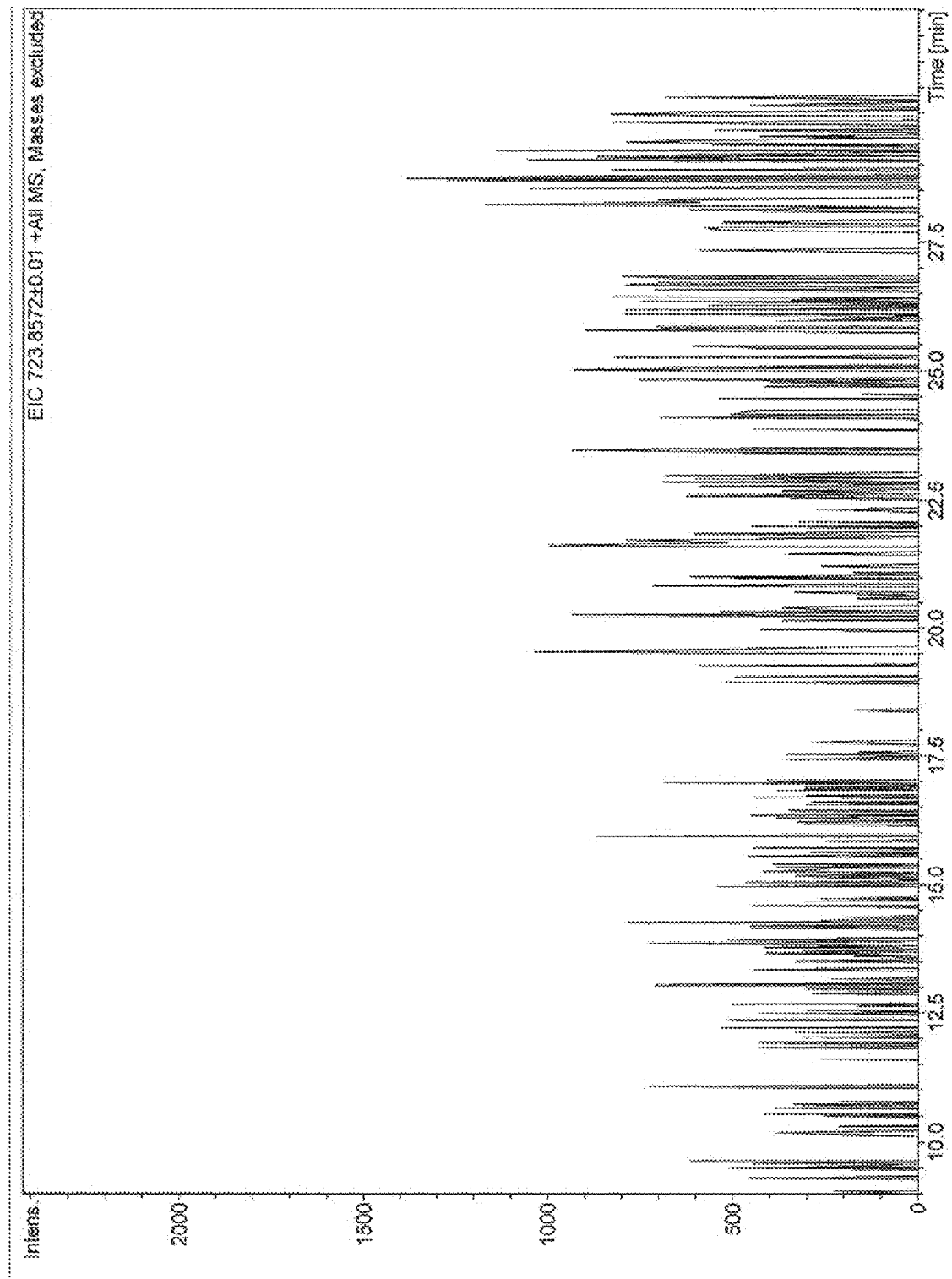
FIG. 2 shows an extracted ion chromatogram on the second peptide fragment obtained by an LC-MS/MS analysis of the composition C2 in Comparative Example 2.

FIG. 2 shows an extracted ion chromatogram on the second peptide fragment obtained by an LC-MS/MS analysis of the composition C2 in Comparative Example 2.

Figure 3:
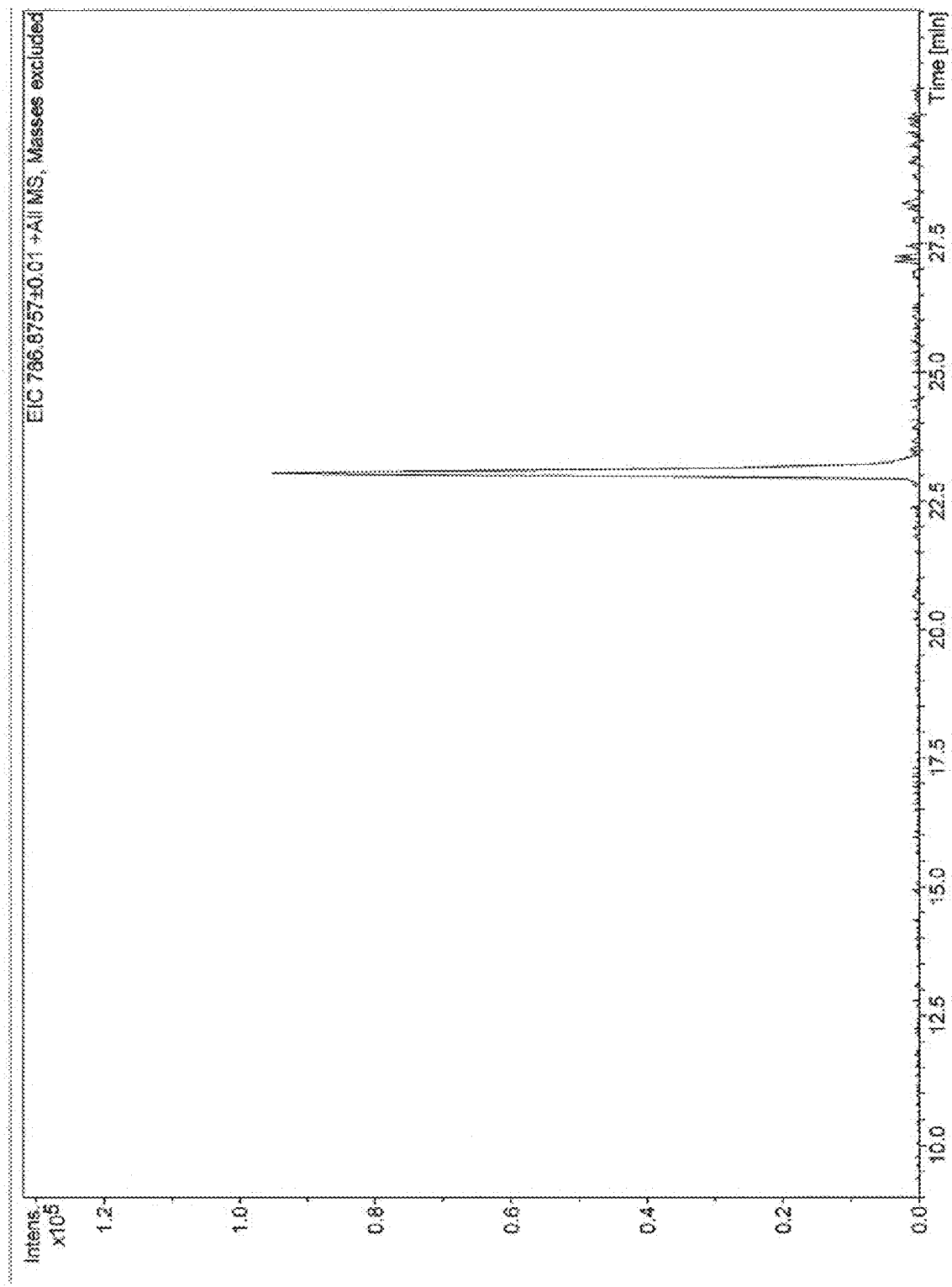
FIG. 3 shows an extracted ion chromatogram on the third peptide fragment obtained by an LC-MS/MS analysis of the composition C2 in Comparative Example 2.

FIG. 3 shows an extracted ion chromatogram on the third peptide fragment obtained by an LC-MS/MS analysis of the composition C2 in Comparative Example 2.

Figure 4:
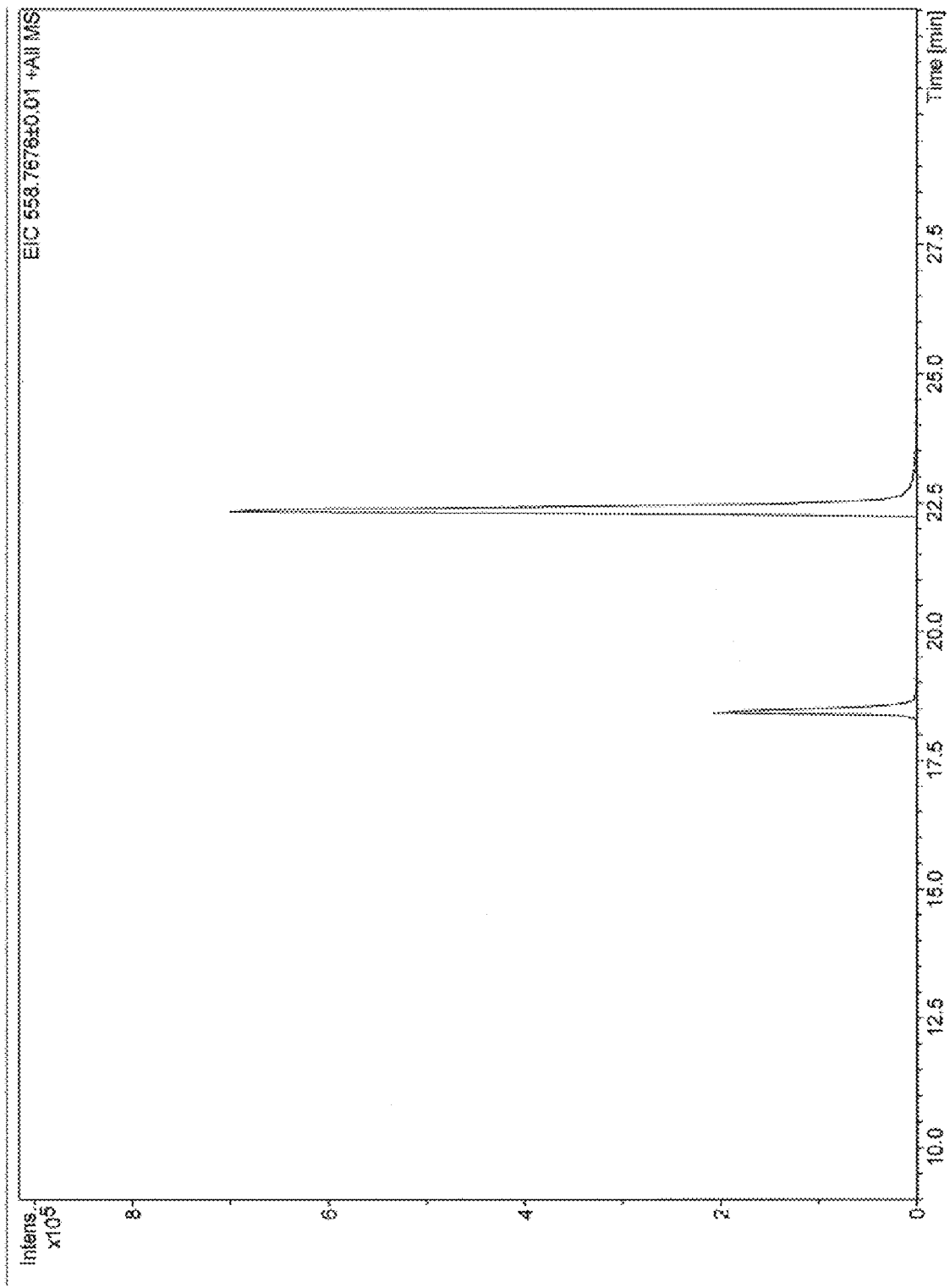
FIG. 4 shows an extracted ion chromatogram on the fourth peptide fragment obtained by an LC-MS/MS analysis of the composition C2 in Comparative Example 2.

FIG. 4 shows an extracted ion chromatogram on the fourth peptide fragment obtained by an LC-MS/MS analysis of the composition C2 in Comparative Example 2.

Figure 5:
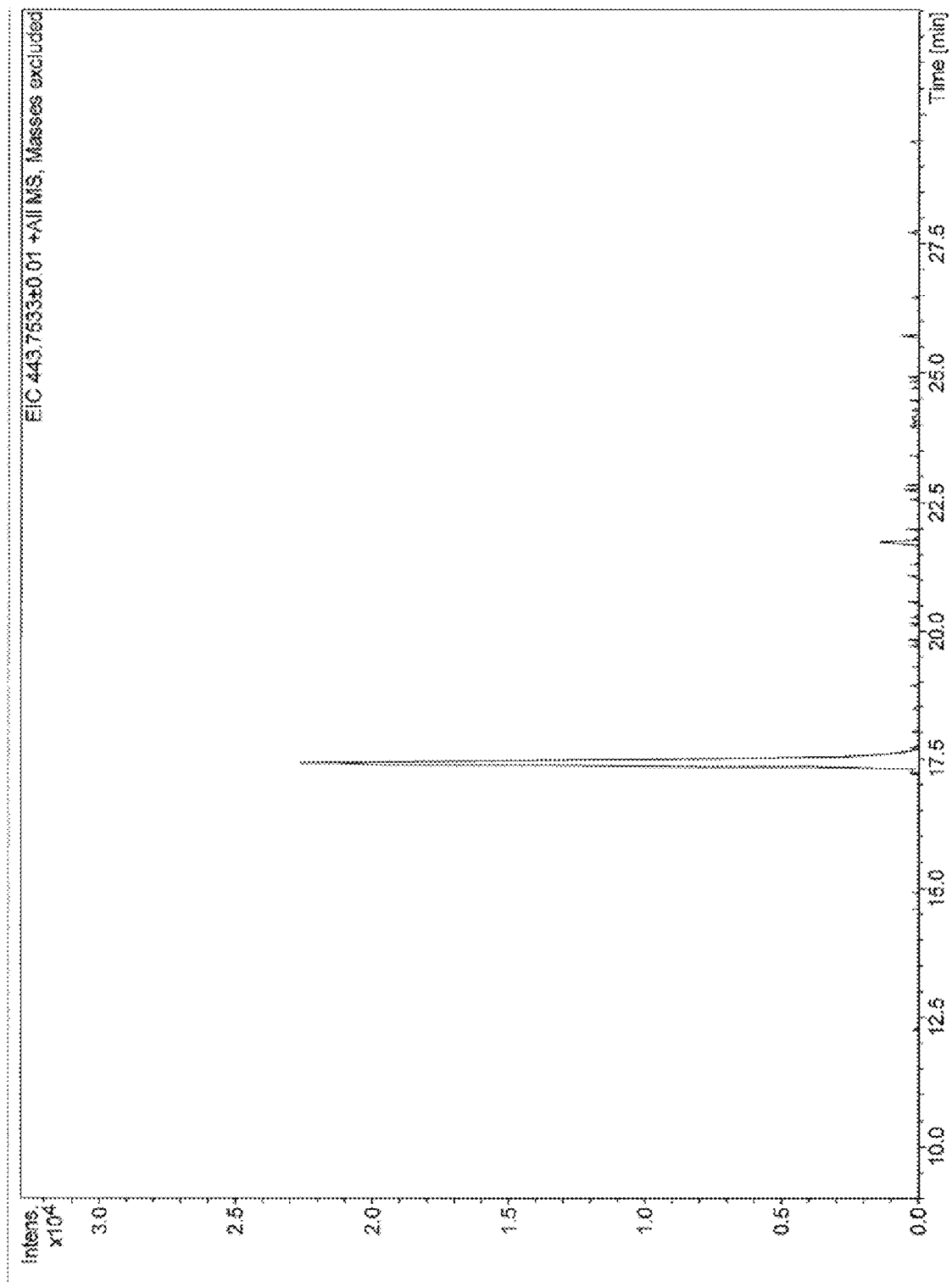
FIG. 5 shows an extracted ion chromatogram on the fifth peptide fragment obtained by an LC-MS/MS analysis of the composition C2 in Comparative Example 2.

FIG. 5 shows an extracted ion chromatogram on the fifth peptide fragment obtained by an LC-MS/MS analysis of the composition C2 in Comparative Example 2.

Figure 6:
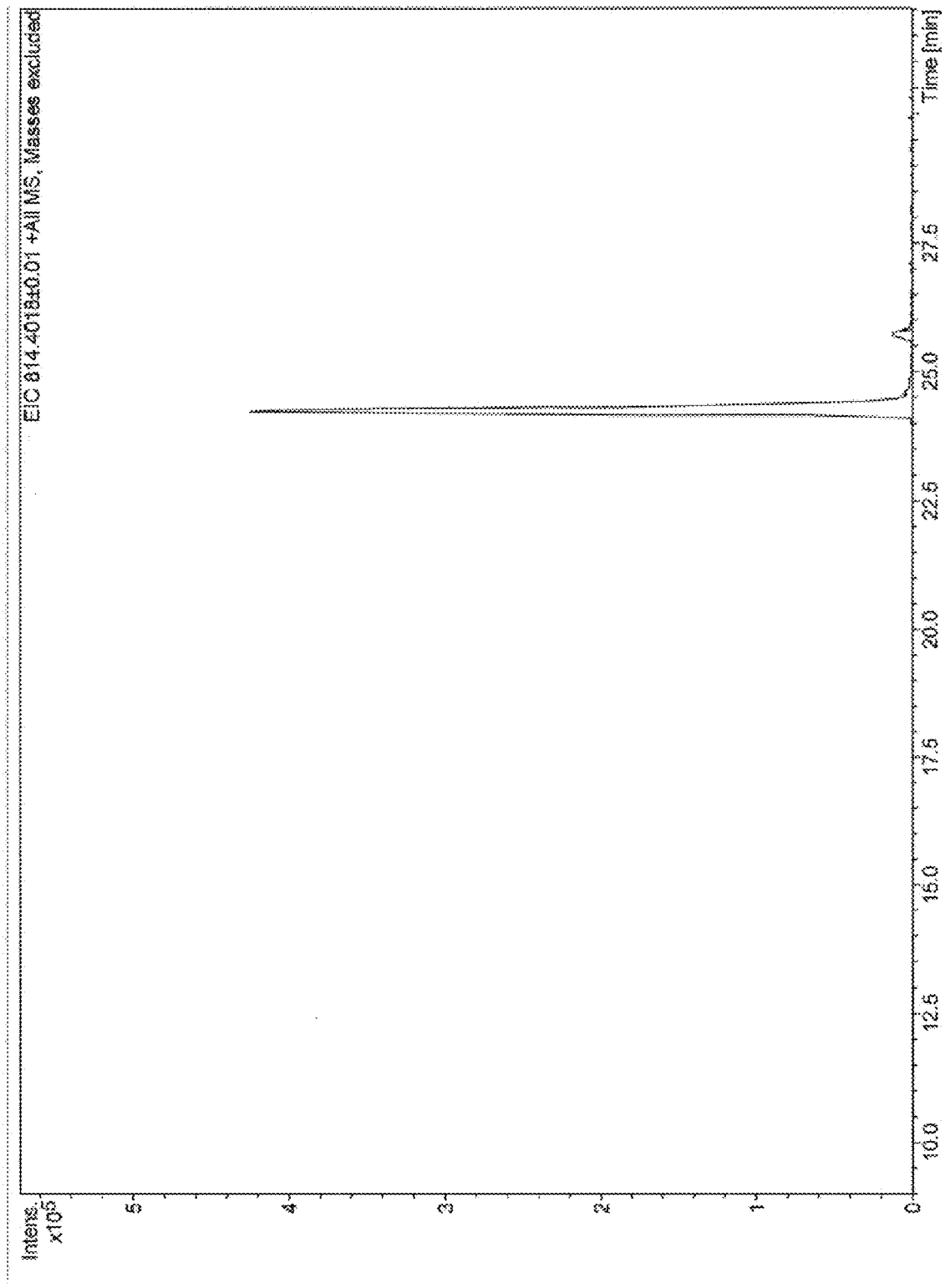
FIG. 6 shows an extracted ion chromatogram on the sixth peptide fragment obtained by an LC-MS/MS analysis of the composition C2 in Comparative Example 2.

FIG. 6 shows an extracted ion chromatogram on the sixth peptide fragment obtained by an LC-MS/MS analysis of the composition C2 in Comparative Example 2.

Figure 7:
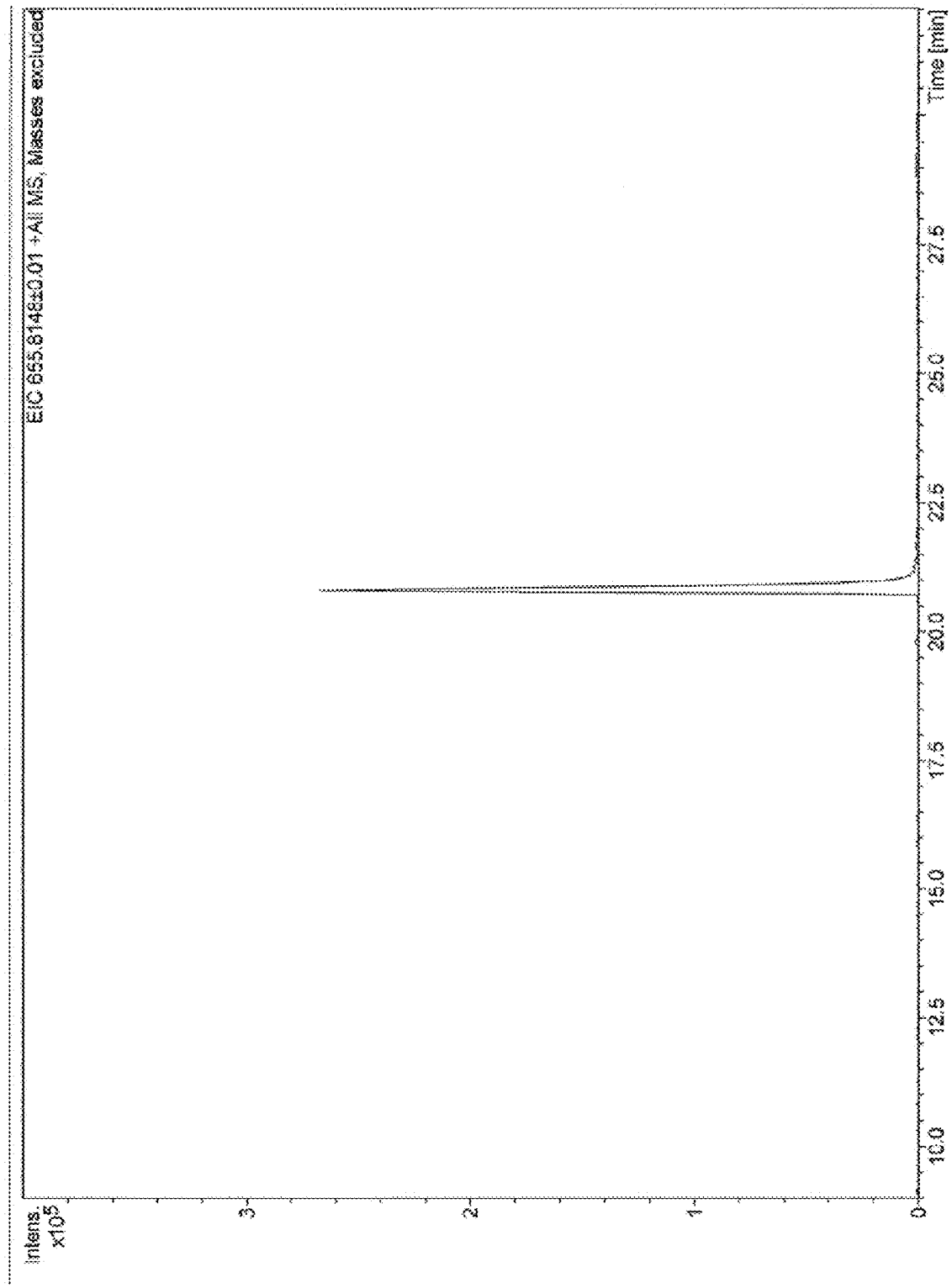
FIG. 7 shows an extracted ion chromatogram on the seventh peptide fragment obtained by an LC-MS/MS analysis of the composition C2 in Comparative Example 2.

FIG. 7 shows an extracted ion chromatogram on the seventh peptide fragment obtained by an LC-MS/MS analysis of the composition C2 in Comparative Example 2.

Figure 8:
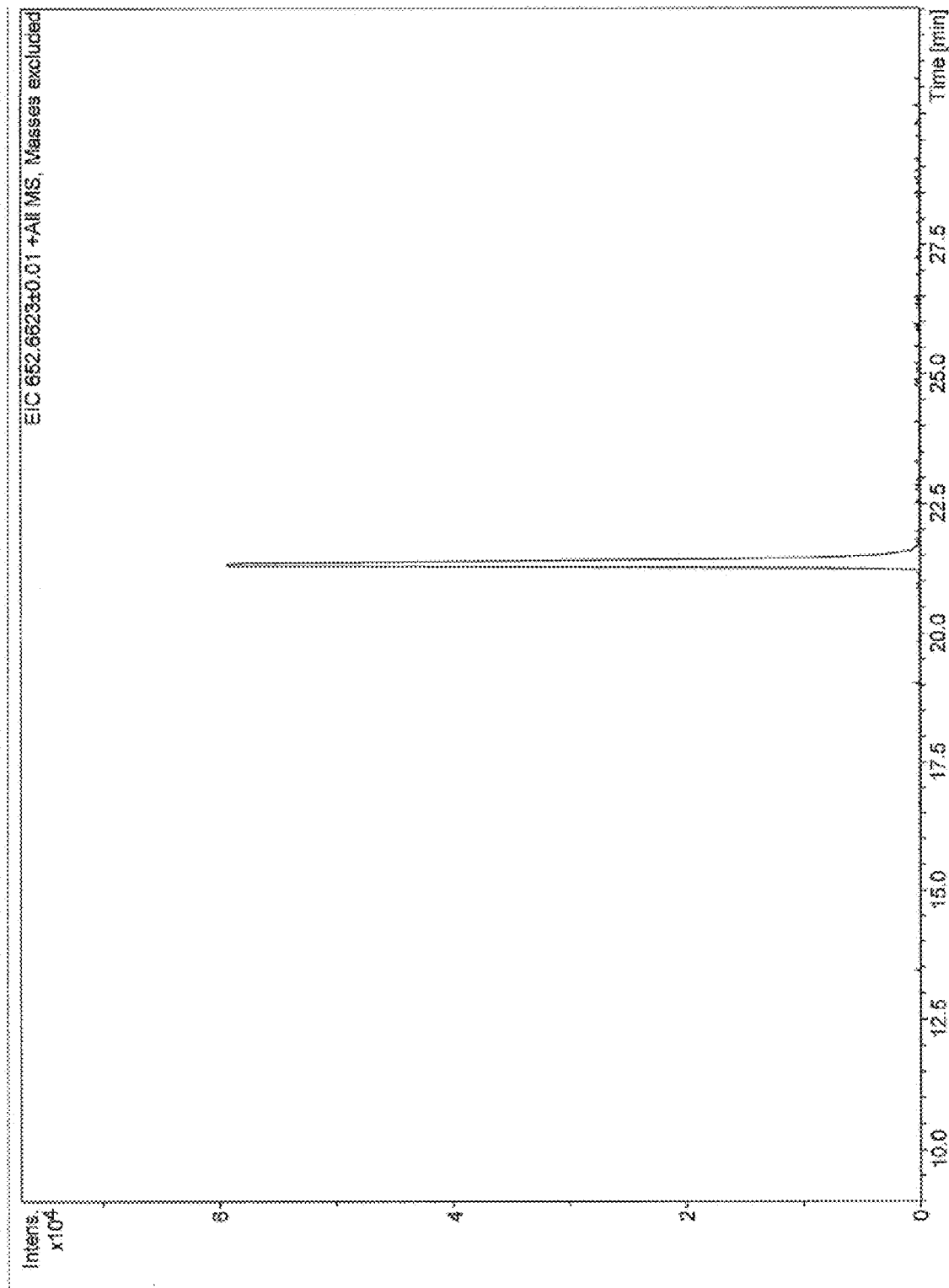
FIG. 8 shows an extracted ion chromatogram on the eighth peptide fragment obtained by an LC-MS/MS analysis of the composition C2 in Comparative Example 2.

FIG. 8 shows an extracted ion chromatogram on the eighth peptide fragment obtained by an LC-MS/MS analysis of the composition C2 in Comparative Example 2.

Figure 9:
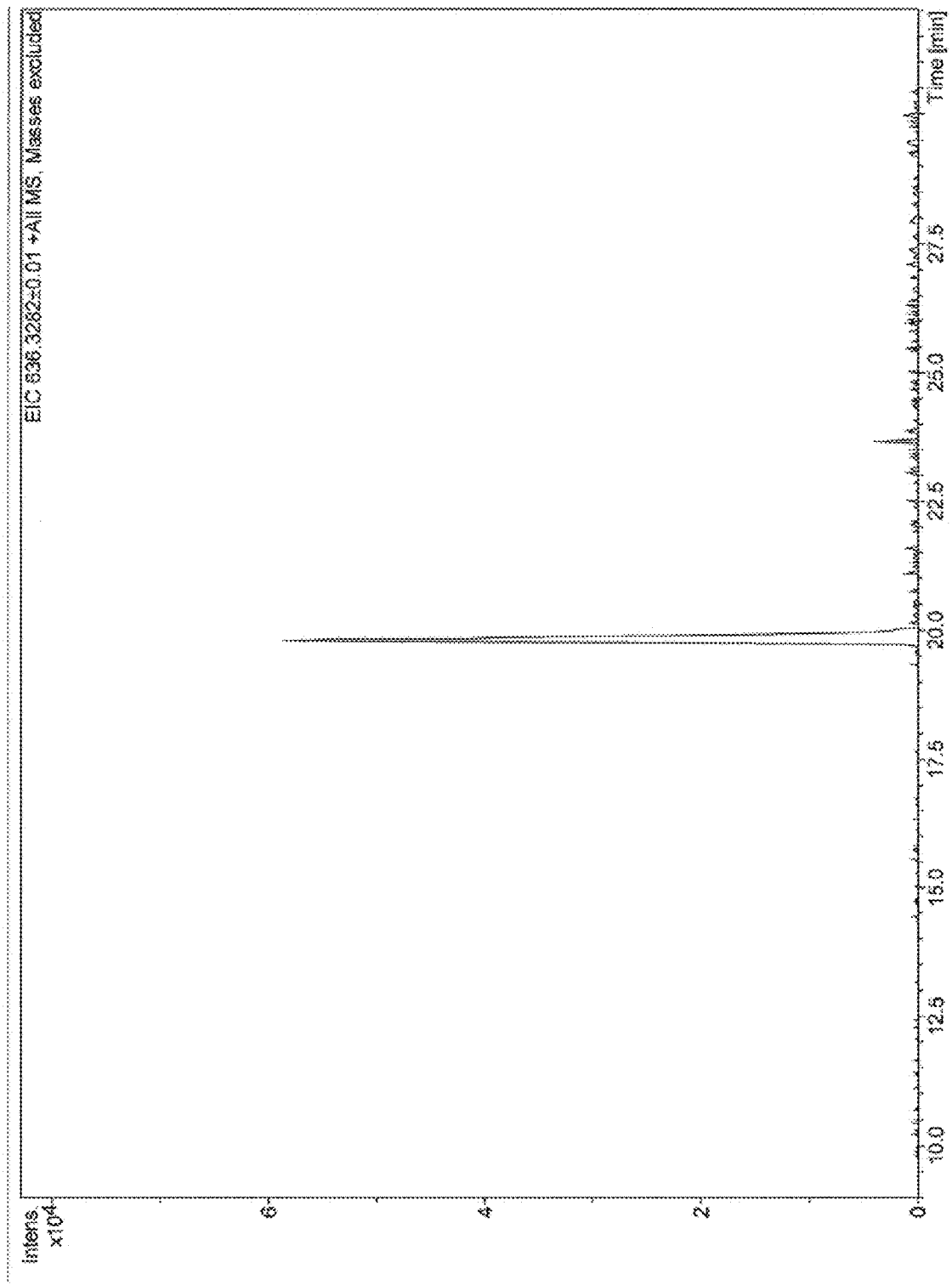
FIG. 9 shows an extracted ion chromatogram on the ninth peptide fragment obtained by an LC-MS/MS analysis of the composition C2 in Comparative Example 2.

FIG. 9 shows an extracted ion chromatogram on the ninth peptide fragment obtained by an LC-MS/MS analysis of the composition C2 in Comparative Example 2.

By using each of the alkaline phosphatase compositions of Comparative Examples 1 to 8, a nucleic acid was dephosphorylated, and the obtained dephosphorylated nucleic acid was labeled with a cyanine-based organic fluorescent dye. Specifically, dephosphorylation reaction and labeling reaction were performed as follows.

Whole blood collected from a healthy individual was centrifuged to obtain 1 mL of serum. From the serum, microRNA was extracted by using the "3D-Gene" RNA extraction reagent from liquid sample kit (manufactured by Toray Industries, Inc.). The obtained extracted microRNA was regarded as a mother liquor and was labeled by using "3D-Gene" miRNA labeling kit (manufactured by Toray Industries, Inc.). Specifically, 5 µL of the obtained extracted microRNA was added to a mixed solution of 0.4 µL of AP buffer and 1.0 µL of Spike Control of the abovementioned kit, and 0.4 µL of the composition C1 was further added to prepare a solution. Then, the prepared solution was incubated at 37° C. for 40 minutes, followed by allowing to stand on ice for 2 minutes. Then, 1.2 µL of LE Buffer, 3.0 µL of 3D-Gene Fluorescent Label, 2.5 µL of Nuclease free water and 1.0 µL of Labeling enzyme were added, and the obtained solution was incubated at 16° C. for 1 hour, followed by incubation at 65° C. for 15 minutes to obtain a labeled nucleic acid. Dephosphorylation reaction and labeling reaction were performed by using the same method as mentioned above, in which the compositions C2 to C8 and the same extracted microRNA mother liquor were used.

By using the obtained labeled nucleic acid, detection of a nucleic acid was performed. Specifically, for the labeled sample RNA, hybridization was performed by using a DNA chip ("3D-Gene" miRNA chip, manufactured by Toray Industries, Inc.) in accordance with the standard protocol thereof. The DNA chip after hybridization was subjected to a microarray scanner (manufactured by Toray Industries, Inc.) to measure the fluorescence intensity. Regarding the setting of the scanner, the laser output was set at 100%, and the voltage setting of the photomultiplier was set at AUTO setting. Detection of a nucleic acid was performed by using a DNA chip (DNA microarray) as mentioned above. The number of valid spots in the DNA chip was determined to calculate the detection rate (%). Specifically, of a total of 2,588 spots on the DNA chip, spots with a value obtained by subtracting the noise (signal value at a site having no spot) from the detection signal value being 100 or more were regarded as valid spots, and the value obtained by dividing the number of valid spots by the number of all spots and by multiplying by 100 was regarded as the detection rate. The results are shown in Tables 4-2 and 5-2.

Examples 1 to 4

The alkaline phosphatase compositions of Comparative Examples 2 to 4 and 8 (compositions C2 to C4 and C8) were purified by the following method to obtain alkaline phosphatase compositions of Examples 1 to 4 (hereinafter referred to as "composition E1" to "composition E4"). The purification method was as follows.

Dialysis Step

The composition C2 (30 μL) was dialyzed three times with a dialysis buffer (1 mL, 50 mM Tris-HCl, 2 mM MgCl$_2$, 0.2 mM ZnCl$_2$) by using a dialysis cup (cutoff molecular weight of 3.5 K), and the concentrate was collected.

Gel Filtration Step

The concentrate after dialysis treatment was collected by filtration with a buffer (2.5 mL, 10 mM Tris-HCl, 1 mM MgCl$_2$, 0.1 mM ZnCl$_2$, 50 mM KCl, 55% by weight glycerin) by using a gel filtration column.

Hydrophobic Column Step

From the collected solution after gel filtration, the alkaline phosphatase fraction was collected by using a hydrophobic column under the following conditions.

Mobile phase flow rate: 1.0 mL/min
Mobile phase A: 20 mM disodium hydrogenphosphate, 3M ammonium sulfate (50/50)
Mobile phase B: 20 mM disodium hydrogenphosphate
Detector: UV 214 nm
Gradient program:

TABLE 3

| Time (min) | Mobile phase A (vol %) | Mobile phase B (vol %) |
|---|---|---|
| 0 | 100 | 0 |
| 3 | 100 | 0 |
| 40 | 0 | 100 |
| 50 | 0 | 100 |
| 55 | 100 | 0 |
| 65 | 100 | 0 |

Dialysis Step

The collected alkaline phosphatase fraction was dialyzed three times under the same conditions as for the abovementioned dialysis, and the concentrate was collected.

Ultrafiltration Step

The collected concentrate was collected by filtration with a buffer (2.5 mL, 10 mM Tris-HCl, 1 mM MgCl$_2$, 0.1 mM ZnCl$_2$, 50 mM KCl, 55% by weight glycerin) by using an ultrafiltration column (cutoff molecular weight of 10 K) to obtain the composition E1.

The compositions E2, E3 and E4 were also obtained from the compositions C3, C4 and C8, respectively, by using the same method as mentioned above.

When the alkaline phosphatase specific activities of the alkaline phosphatase compositions of Examples 1 to 4 were measured, they were 2,490 U/mg for the composition E1, 2,420 U/mg for the composition E2, 2,522 U/mg for the composition E3, and 2,470 U/mg for the composition E4. The alkaline phosphatase specific activities were measured in the same manner as mentioned above.

An aqueous 10% by weight alkaline phosphatase solution was prepared from each of the compositions E1 to E4, and by using this aqueous solution, an LC-UV analysis and an LC-MS/MS analysis were performed. Based on the extracted ion chromatogram obtained by the LC-MS/MS analysis, the peak area value of each of the first peptide fragment consisting of the amino acid sequence set forth in SEQ ID NO: 1 (EAEAEFLIPAEEENPAFWNRQAAQ), the second peptide fragment consisting of the amino acid sequence set forth in SEQ ID NO: 2 (EGVSLEKREAEAE), and the third peptide fragment consisting of the amino acid sequence set forth in SEQ ID NO: 3 (IPAEEENPAFWNR), the fourth peptide fragment consisting of the amino acid sequence set forth in SEQ ID NO: 4 (DRQVPDSAGTA), the fifth peptide fragment consisting of the amino acid sequence set forth in SEQ ID NO: 5 (APGKALDSK), the sixth peptide fragment consisting of the amino acid sequence set forth in SEQ ID NO: 6 (VPLASETHGGEDVAVF), the seventh peptide fragment consisting of the amino acid sequence set forth in SEQ ID NO: 7 (VPLASETHGGEDV), the eighth peptide fragment consisting of the amino acid sequence set forth in SEQ ID NO: 8 (GPQAHLVHGVQEETFVAH), and the ninth peptide fragment consisting of the amino acid sequence set forth in SEQ ID NO: 9 (GPQAHLVHGVQE) was calculated by an automatic integration method. Based on the chromatogram obtained by the LC-UV analysis, the peak area value of the alkaline phosphatase was calculated by an automatic integration method. In the LC-UV analysis, the alkaline phosphatase was detected as a component having absorption at 214 nm.

Figure 10:
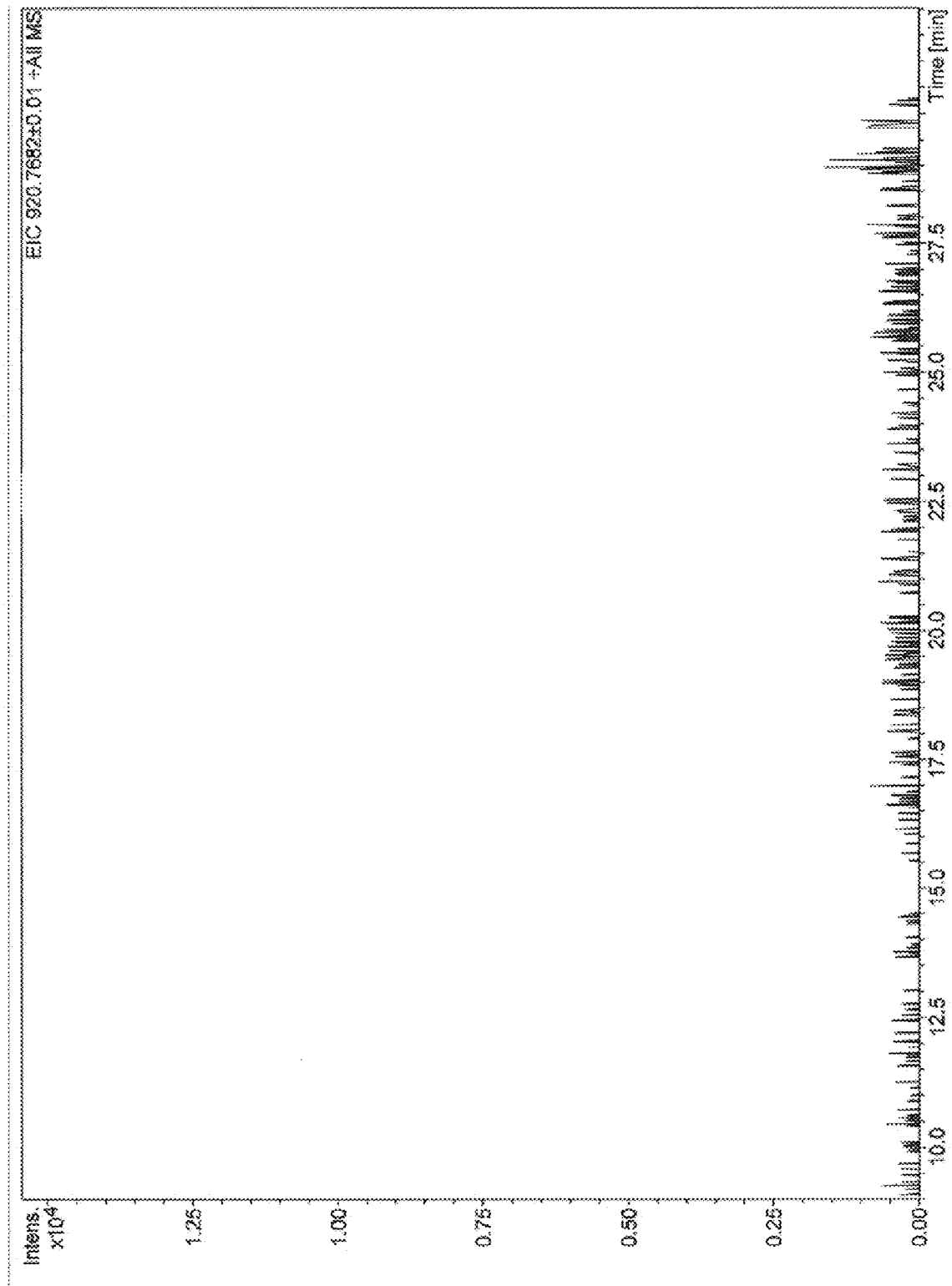
FIG. 10 shows an extracted ion chromatogram on the first peptide fragment obtained by an LC-MS/MS analysis of the composition E1 (purified product of the composition C2) in Example 1.

FIG. 10 shows an extracted ion chromatogram on the first peptide fragment obtained by an LC-MS/MS analysis of the composition E1 (purified product of the composition C2) in Example 1.

Figure 11:
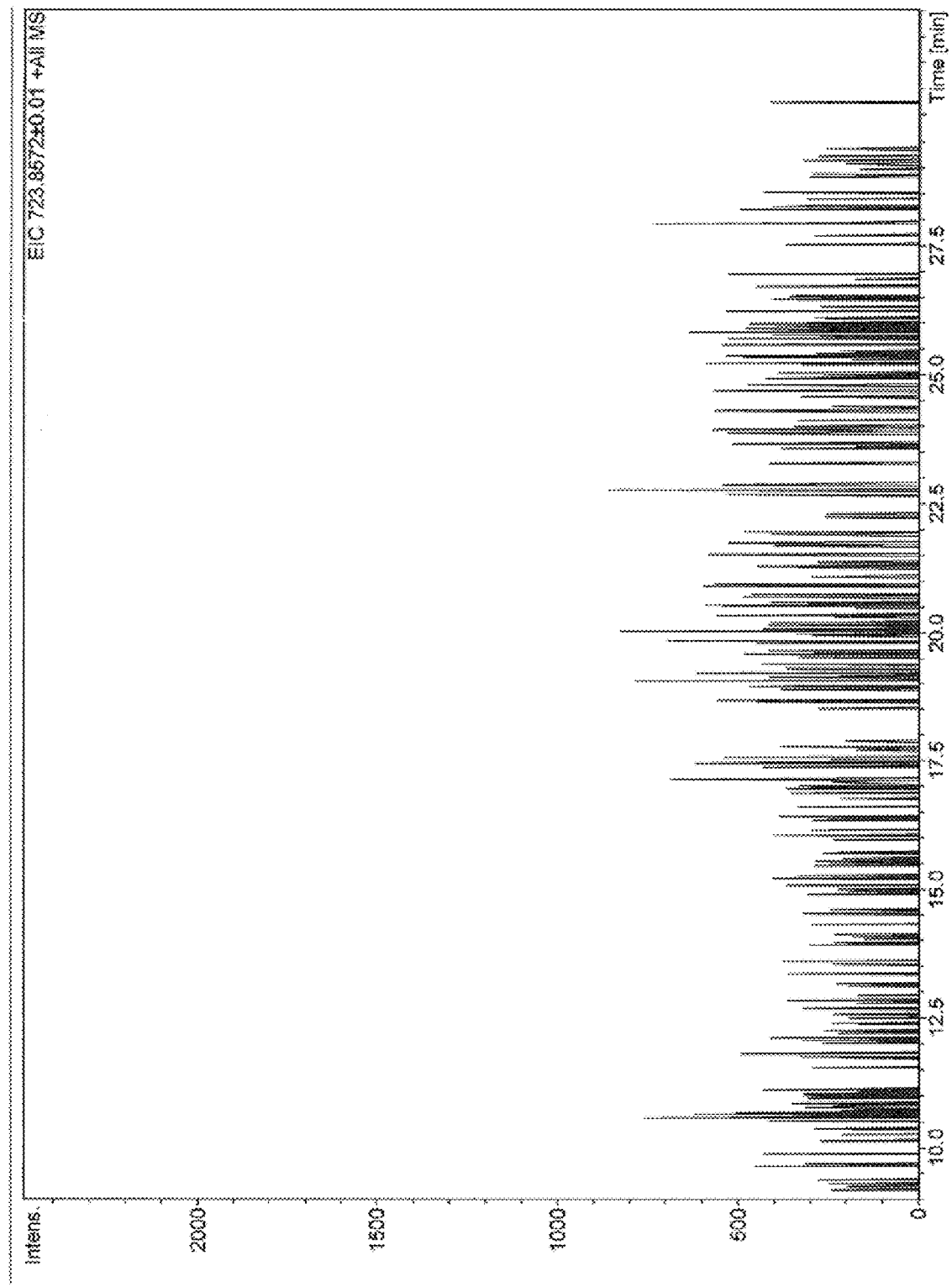
FIG. 11 shows an extracted ion chromatogram on the second peptide fragment obtained by an LC-MS/MS analysis of the composition E1 (purified product of the composition C2) in Example 1.

FIG. 11 shows an extracted ion chromatogram on the second peptide fragment obtained by an LC-MS/MS analysis of the composition E1 (purified product of the composition C2) in Example 1.

Figure 12:
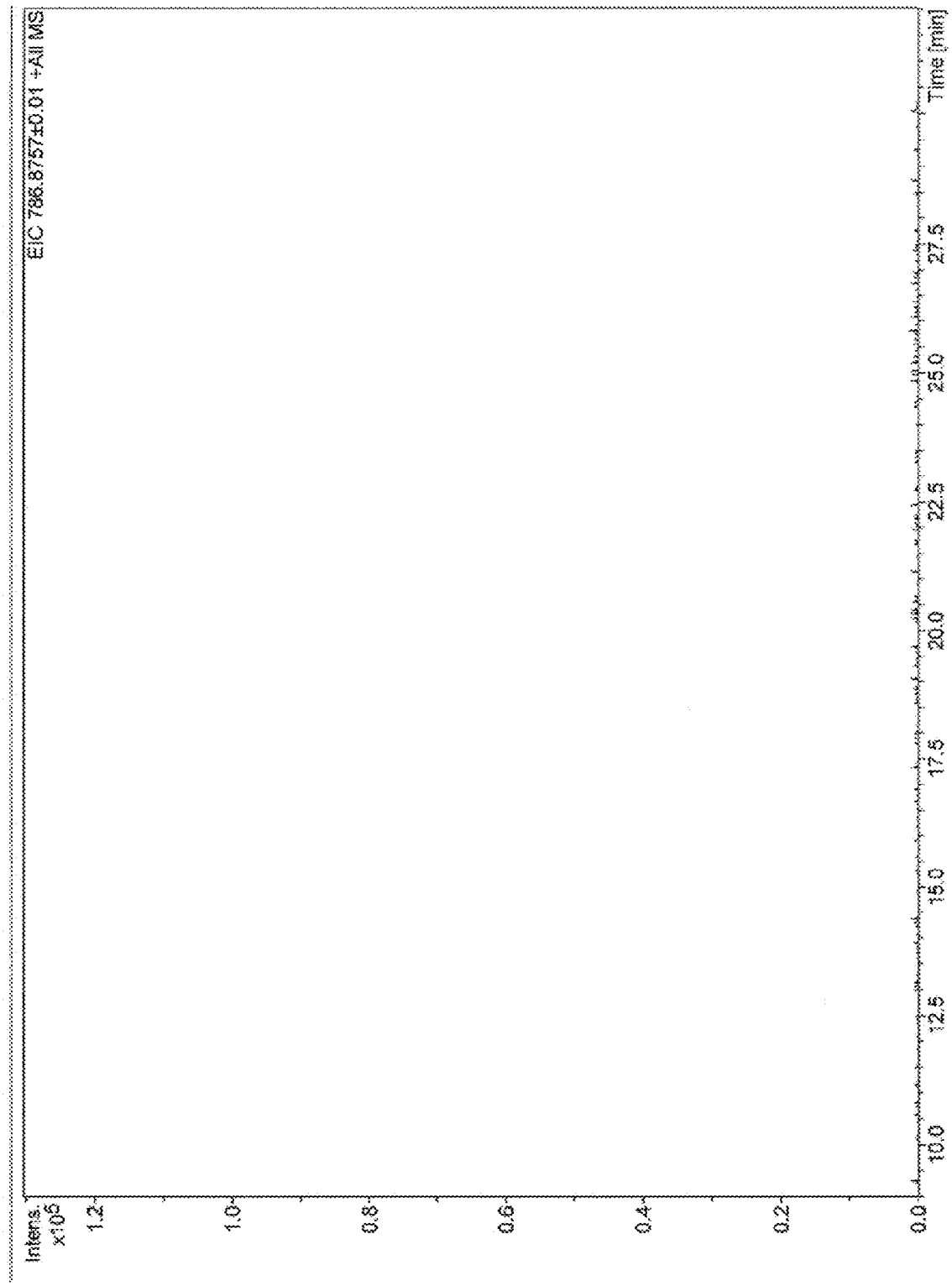
FIG. 12 shows an extracted ion chromatogram on the third peptide fragment obtained by an LC-MS/MS analysis of the composition E1 (purified product of the composition C2) in Example 1.

FIG. 12 shows an extracted ion chromatogram on the third peptide fragment obtained by an LC-MS/MS analysis of the composition E1 (purified product of the composition C2) in Example 1.

Figure 13:
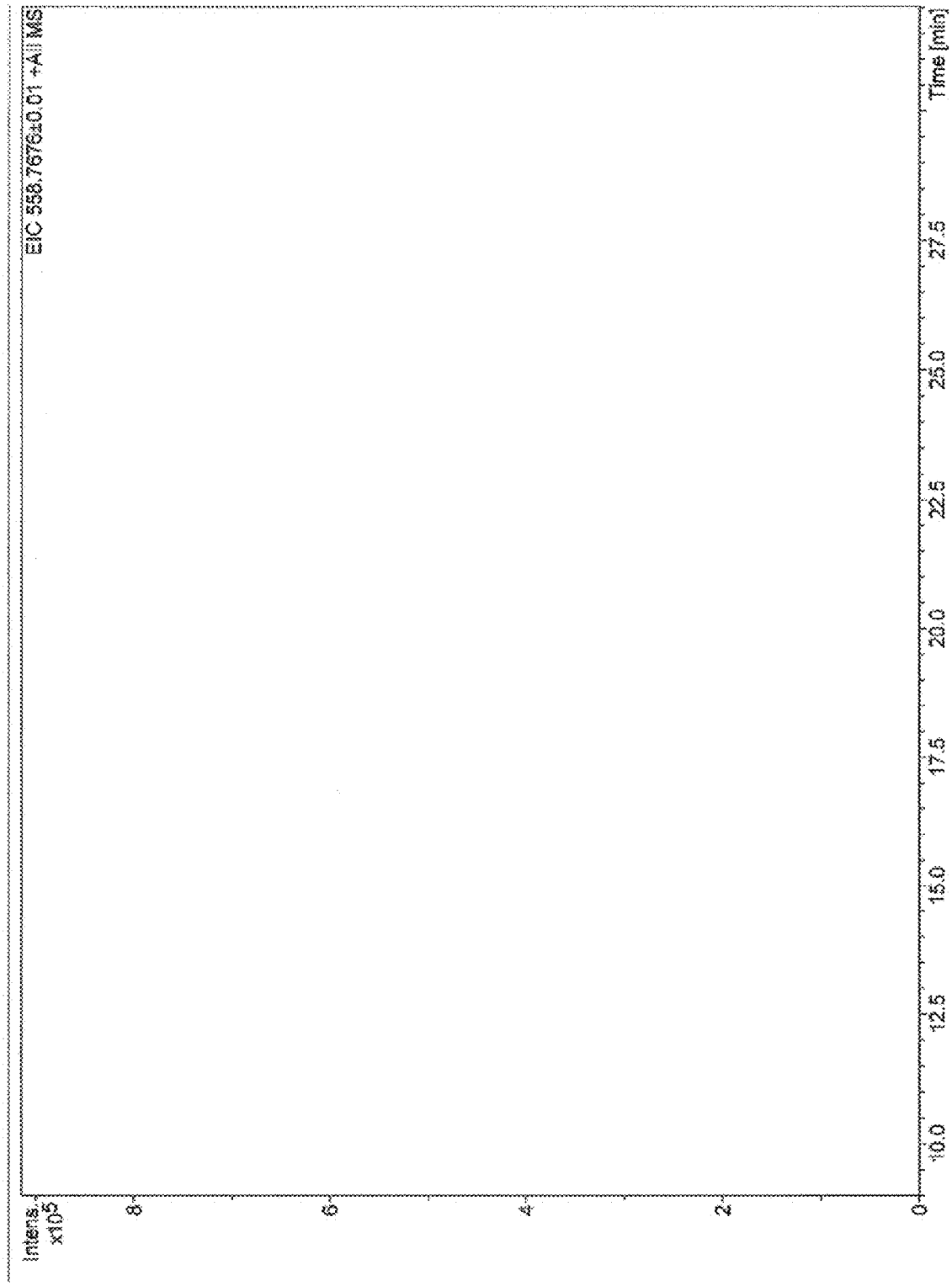
FIG. 13 shows an extracted ion chromatogram on the fourth peptide fragment obtained by an LC-MS/MS analysis of the composition E1 (purified product of the composition C2) in Example 1.

FIG. 13 shows an extracted ion chromatogram on the fourth peptide fragment obtained by an LC-MS/MS analysis of the composition E1 (purified product of the composition C2) in Example 1.

Figure 14:
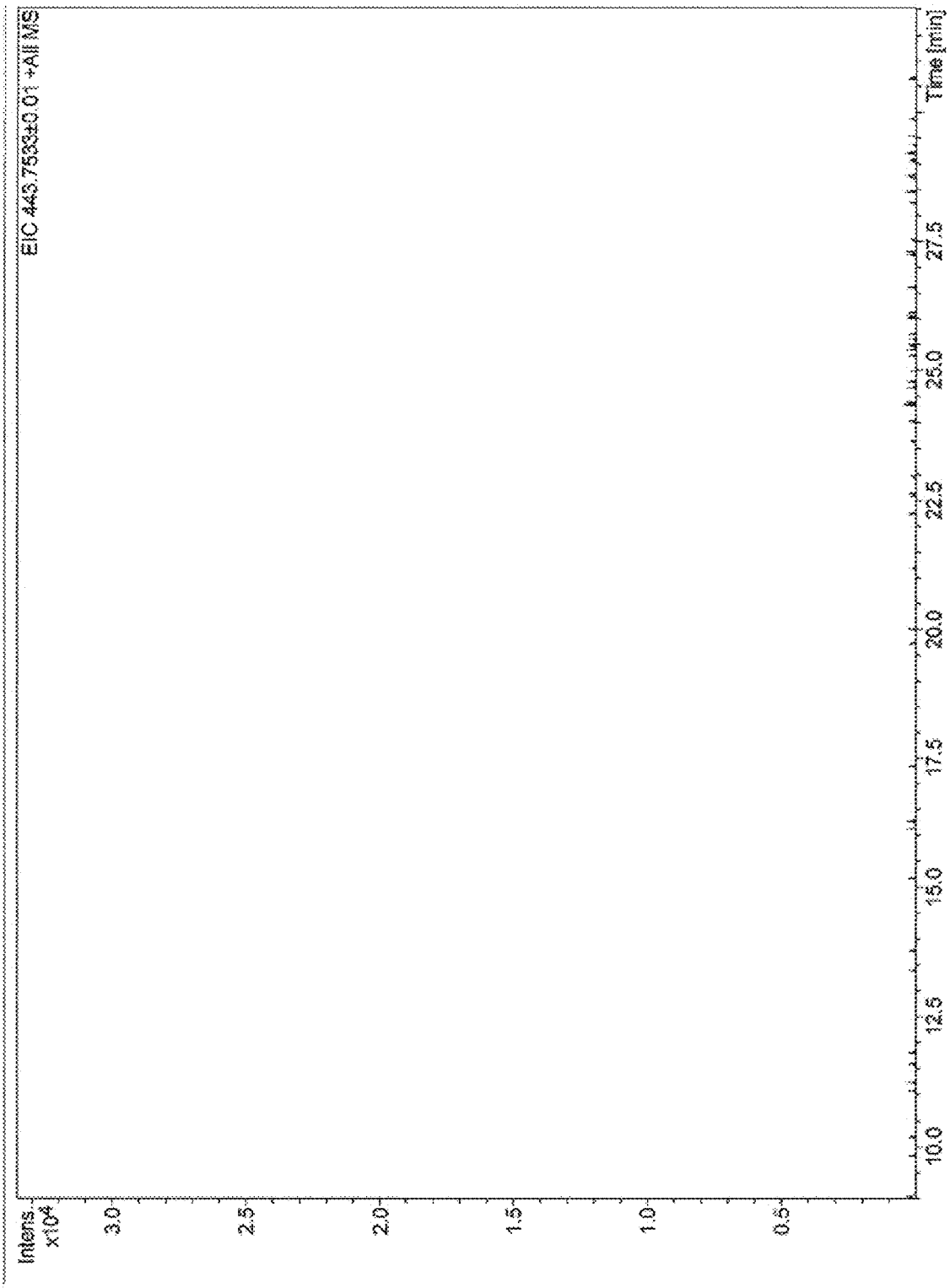
FIG. 14 shows an extracted ion chromatogram on the fifth peptide fragment obtained by an LC-MS/MS analysis of the composition E1 (purified product of the composition C2) in Example 1.

FIG. 14 shows an extracted ion chromatogram on the fifth peptide fragment obtained by an LC-MS/MS analysis of the composition E1 (purified product of the composition C2) in Example 1.

Figure 15:
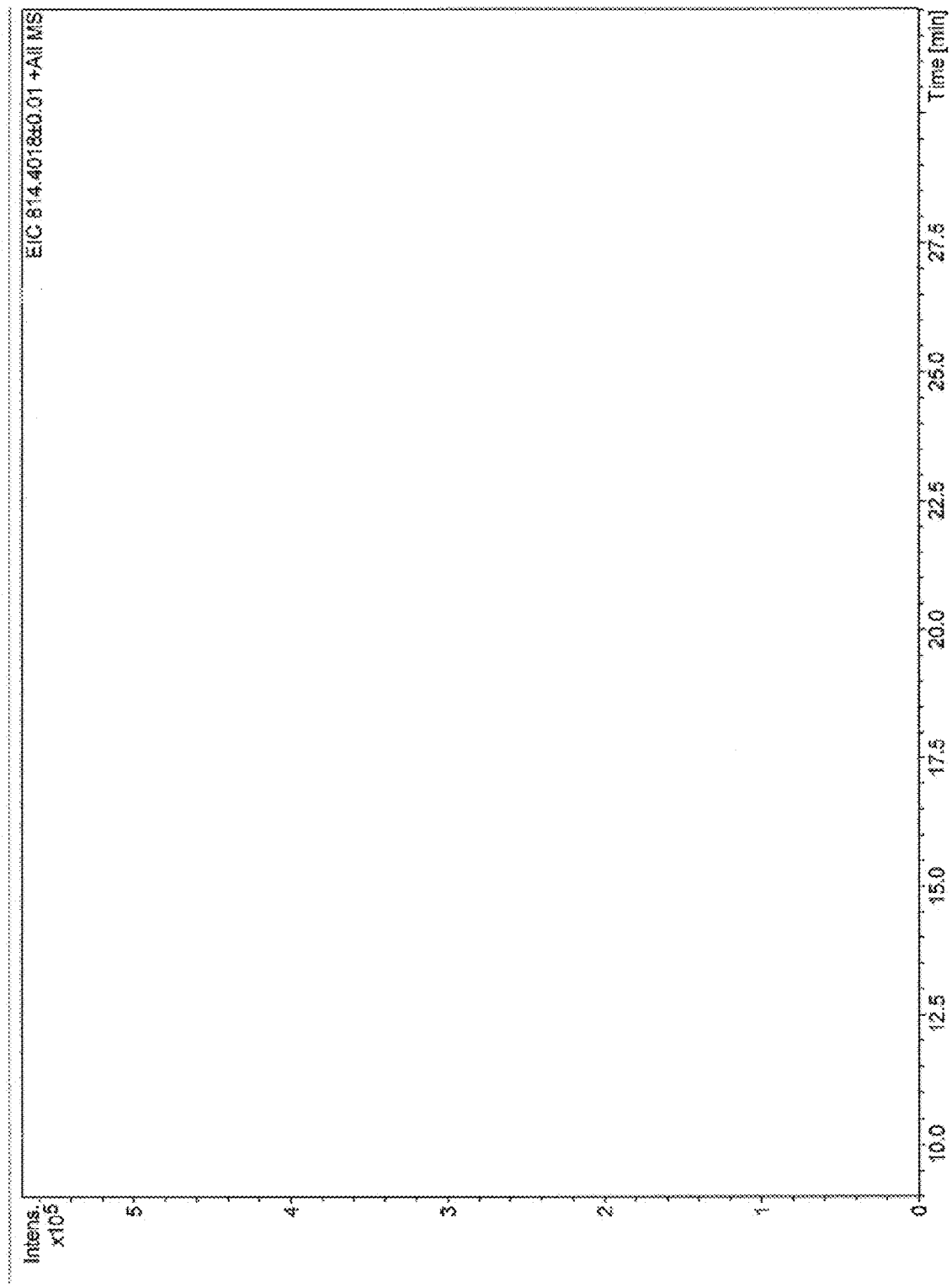
FIG. 15 shows an extracted ion chromatogram on the sixth peptide fragment obtained by an LC-MS/MS analysis of the composition E1 (purified product of the composition C2) in Example 1.

FIG. 15 shows an extracted ion chromatogram on the sixth peptide fragment obtained by an LC-MS/MS analysis of the composition E1 (purified product of the composition C2) in Example 1.

Figure 16:
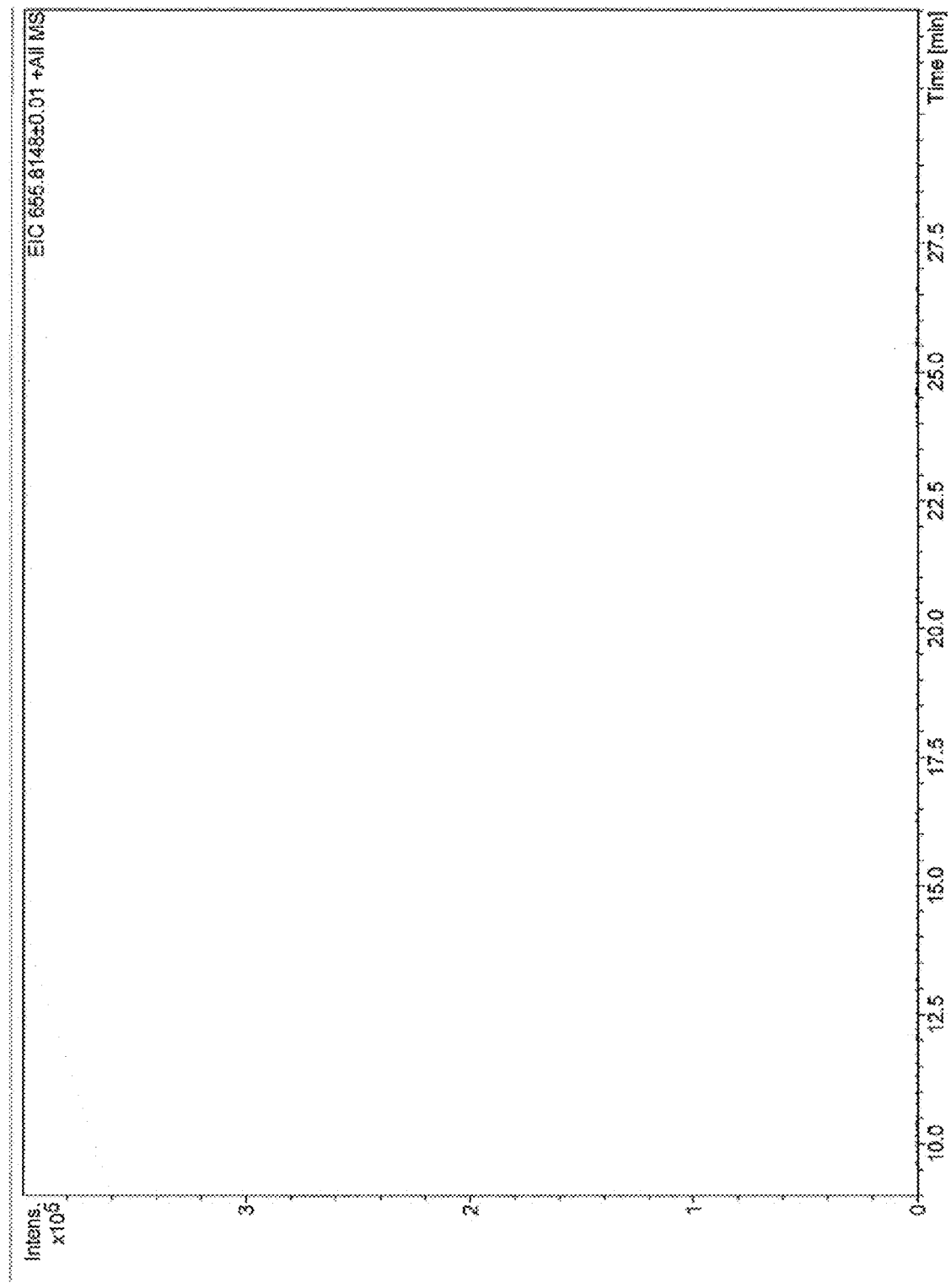
FIG. 16 shows an extracted ion chromatogram on the seventh peptide fragment obtained by an LC-MS/MS analysis of the composition E1 (purified product of the composition C2) in Example 1.

FIG. 16 shows an extracted ion chromatogram on the seventh peptide fragment obtained by an LC-MS/MS analysis of the composition E1 (purified product of the composition C2) in Example 1.

Figure 17:
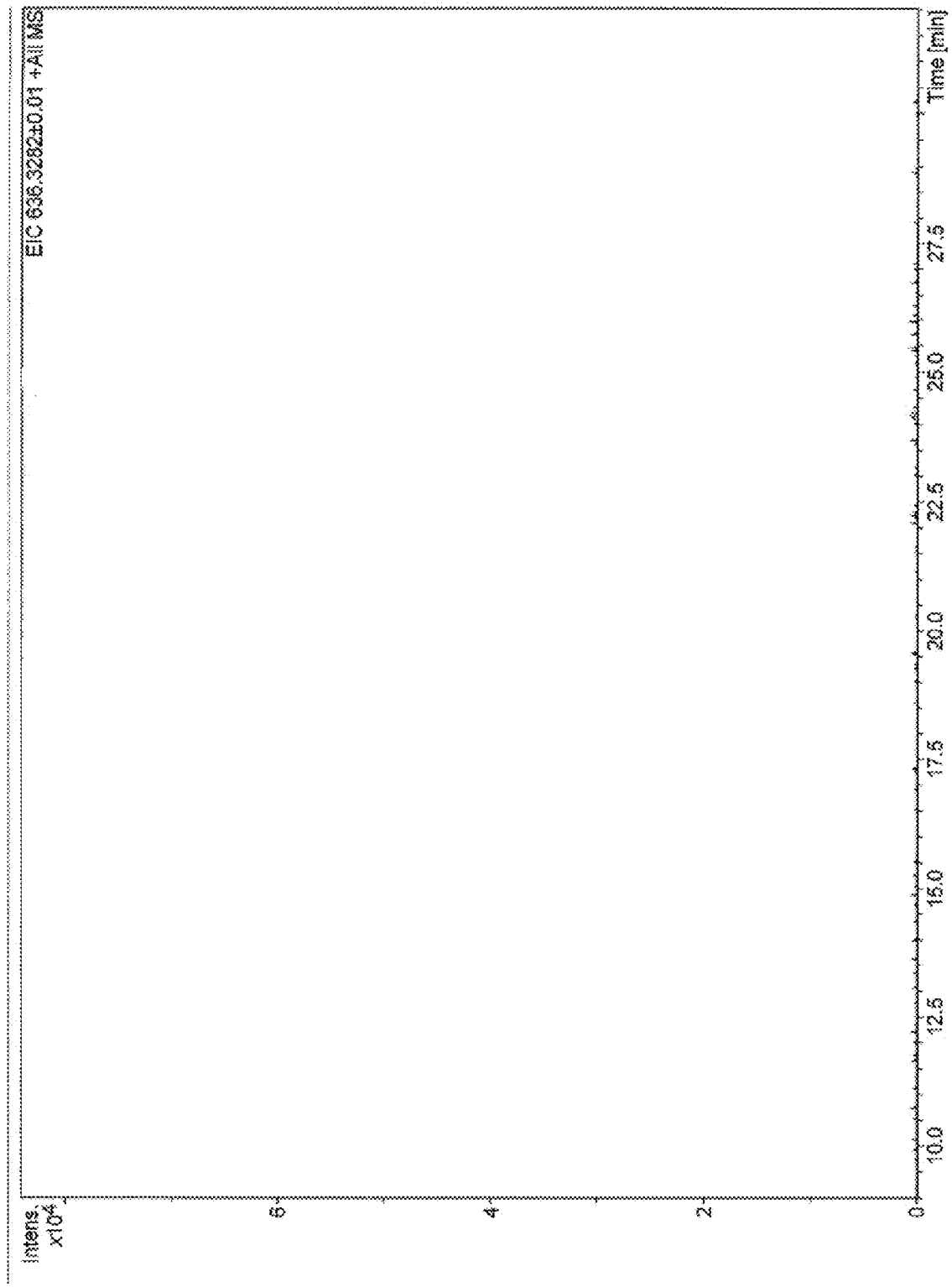
FIG. 17 shows an extracted ion chromatogram on the eighth peptide fragment obtained by an LC-MS/MS analysis of the composition E1 (purified product of the composition C2) in Example 1.

FIG. 17 shows an extracted ion chromatogram on the eighth peptide fragment obtained by an LC-MS/MS analysis of the composition E1 (purified product of the composition C2) in Example 1.

Figure 18:
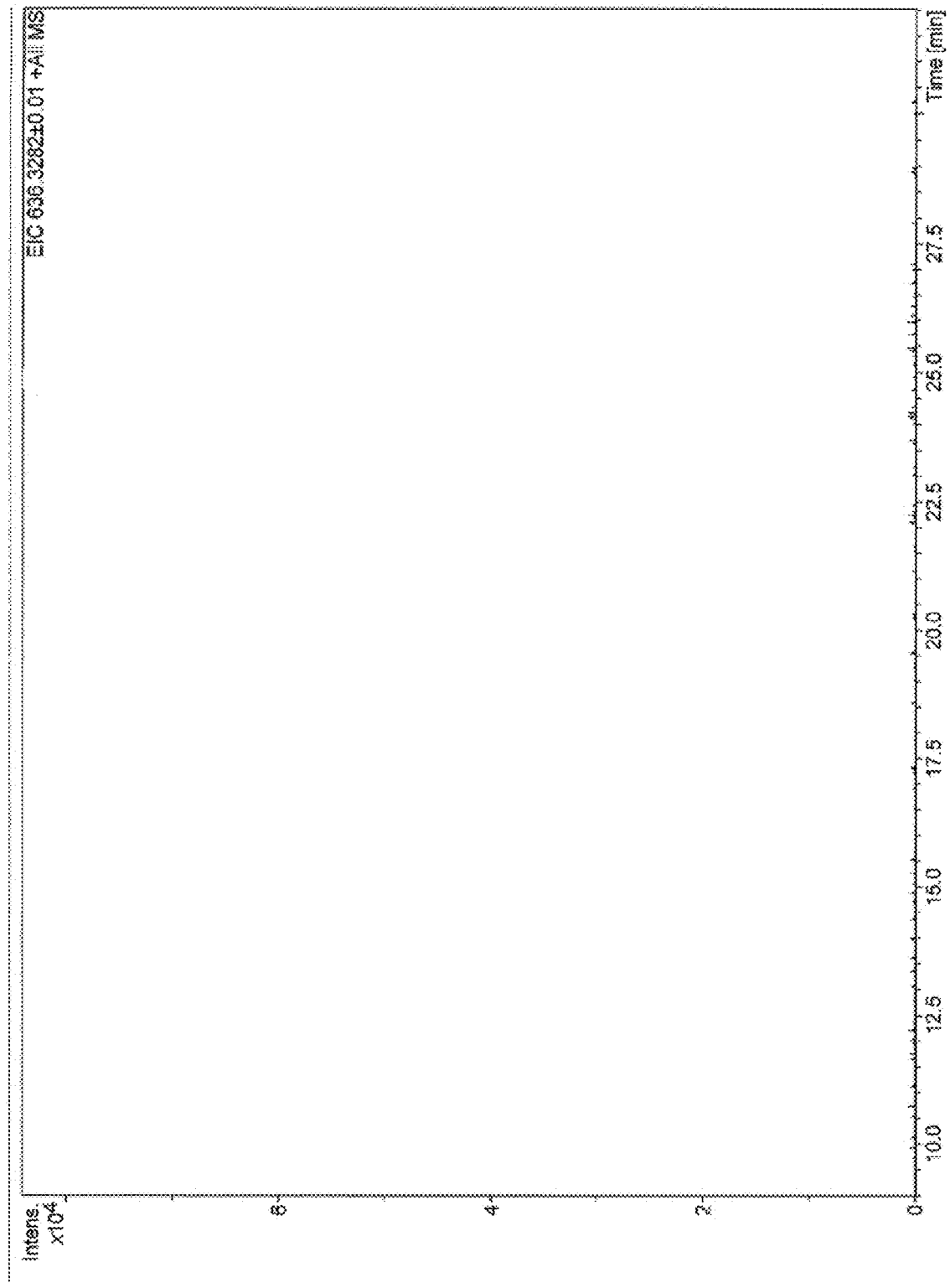
FIG. 18 shows an extracted ion chromatogram on the ninth peptide fragment obtained by an LC-MS/MS analysis of the composition E1 (purified product of the composition C2) in Example 1.

FIG. 18 shows an extracted ion chromatogram on the ninth peptide fragment obtained by an LC-MS/MS analysis of the composition E1 (purified product of the composition C2) in Example 1.

Figure 19:
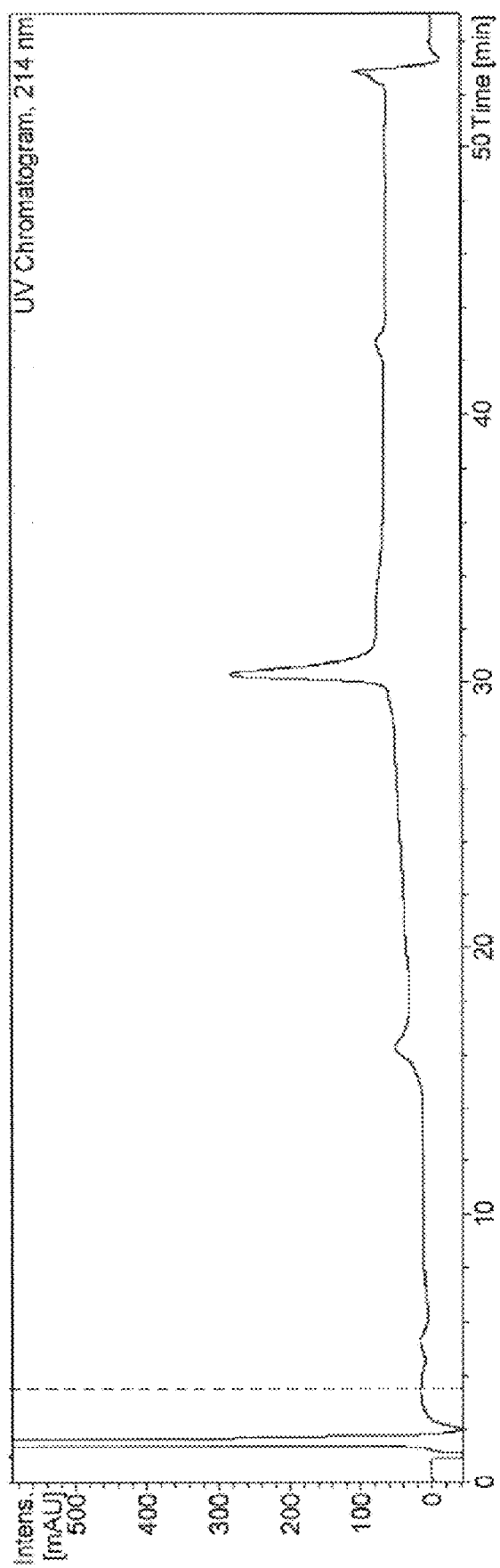
FIG. 19 shows a chromatogram on an alkaline phosphatase obtained by an LC-UV analysis of the composition E1 (purified product of the composition C2) in Example 1.

FIG. 19 shows a chromatogram on an alkaline phosphatase obtained by an LC-UV analysis of the composition E1 (purified product of the composition C2) in Example 1. It is noted that a chromatogram on an alkaline phosphatase obtained by an LC-UV analysis of each composition in Examples 2 to 4 and Comparative Examples 1 to 8 was the same as FIG. 19.

By using the alkaline phosphatase compositions of Examples 1 to 4, a nucleic acid was dephosphorylated, and the obtained dephosphorylated nucleic acid was labeled with a cyanine-based organic fluorescent dye. Dephosphorylation reaction and labeling reaction were performed in the same manner as mentioned above.

By using the obtained labeled nucleic acid, detection of a nucleic acid was performed. Detection of a nucleic acid was performed by using a DNA chip (DNA microarray) as mentioned above. The number of valid spots in the DNA chip was determined to calculate the detection rate (%). The results are shown in Tables 4-1 and 5-1.

TABLE 4-1

|  | Examples | | | |
| --- | --- | --- | --- | --- |
|  | 1 | 2 | 3 | 4 |
| Peak area value of First peptide fragment ($X_1$) | 1056 | 2637 | 513 | 798 |
| Peak area value of Second peptide fragment ($X_2$) | 1272 | 884 | 1616 | 280 |
| Peak area value of Third peptide fragment ($X_3$) | 376 | 940 | 5964 | 793 |
| Peak area value of Fourth peptide fragment ($X_4$) | 230 | 200 | 200 | 200 |
| Peak area value of Fifth peptide fragment ($X_5$) | 200 | 200 | 200 | 200 |
| Peak area value of Sixth peptide fragment ($X_6$) | 1783 | 517 | 2416 | 246 |
| Peak area value of Seventh peptide fragment ($X_7$) | 1766 | 949 | 1769 | 585 |
| Peak area value of Eighth peptide fragment ($X_8$) | 226 | 226 | 360 | 200 |
| Peak area value of Ninth peptide fragment ($X_9$) | 668 | 367 | 736 | 278 |
| Peak area value of Alkaline phosphatase (Y) | 263754 | 268264 | 267135 | 258635 |

TABLE 4-2

|  | Comparative Examples | | | | | | | |
| --- | --- | --- | --- | --- | --- | --- | --- | --- |
|  | 1 | 2 | 3 | 4 | 5 | 6 | 7 | 8 |
| Peak area value of First peptide fragment ($X_1$) | 8692 | 16816 | 2394 | 101556 | 13991 | 24543 | 84877 | 18875 |
| Peak area value of Second peptide fragment ($X_2$) | 2279 | 3389 | 3647 | 1887 | 10718 | 2944 | 9570 | 6445 |
| Peak area value of Third peptide fragment ($X_3$) | 3777 | 66744 | 49478 | 7674 | 5324 | 1529 | 32848 | 37098 |
| Peak area value of Fourth peptide fragment ($X_4$) | 10940 | 1594116 | 145105 | 16140 | 1543 | 1765 | 13135 | 311710 |
| Peak area value of Fifth peptide fragment ($X_5$) | 670 | 5794 | 2942 | 377 | 1367 | 472 | 4549 | 4550 |
| Peak area value of Sixth peptide fragment ($X_6$) | 7534 | 23335 | 125531 | 1405 | 16063 | 1406 | 37705 | 33511 |
| Peak area of Seventh peptide fragment ($X_7$) | 4536 | 2811195 | 5945 | 124326 | 17235 | 6523 | 118914 | 672270 |
| Peak area value of Eighth peptide fragment ($X_8$) | 5580 | 637579 | 37977 | 78293 | 2662 | 481 | 12520 | 107131 |
| Peak area value of Ninth peptide fragment ($X_9$) | 1050 | 564467 | 2922 | 22250 | 1197 | 2012 | 18566 | 464618 |
| Peak area value of Alkaline phosphatase (Y) | 268197 | 288388 | 245377 | 208272 | 232234 | 232042 | 272193 | 276191 |

TABLE 5-1

|  | Examples | | | |
| --- | --- | --- | --- | --- |
|  | 1 | 2 | 3 | 4 |
| ($X_1$/Y) × 100 | 0.4002 | 0.9830 | 0.1920 | 0.3085 |
| ($X_2$/Y) × 100 | 0.4822 | 0.3293 | 0.6048 | 0.1083 |
| ($X_3$/Y) × 100 | 0.1425 | 0.3506 | 2.2327 | 0.3066 |
| (($X_1$ + $X_2$)/Y) × 100 | 0.8824 | 1.3123 | 0.7968 | 0.4168 |
| (($X_1$ + $X_3$)/Y) × 100 | 0.5427 | 1.3335 | 2.4247 | 0.6152 |
| (($X_1$ + $X_2$ + $X_3$)/Y) × 100 | 1.0249 | 1.6628 | 3.0295 | 0.7234 |
| ($X_4$/Y) × 100 | 0.0874 | 0.0746 | 0.0749 | 0.0773 |
| ($X_5$/Y) × 100 | 0.0758 | 0.0746 | 0.0749 | 0.0773 |
| ($X_6$/Y) × 100 | 0.6762 | 0.1928 | 0.9044 | 0.0951 |
| ($X_7$/Y) × 100 | 0.6697 | 0.3536 | 0.6624 | 0.2262 |

TABLE 5-1-continued

| | Examples | | | |
|---|---|---|---|---|
| | 1 | 2 | 3 | 4 |
| $(X_8/Y) \times 100$ | 0.0856 | 0.0843 | 0.1346 | 0.0773 |
| $(X_9/Y) \times 100$ | 0.2534 | 0.1367 | 0.2756 | 0.1075 |
| $((X_6 + X_7)/Y) \times 100$ | 1.3459 | 0.5463 | 1.5668 | 0.3213 |
| $((X_8 + X_9)/Y) \times 100$ | 0.3390 | 0.2210 | 0.4102 | 0.1848 |
| $((X_6 + X_7 + X_8 + X_9)/Y) \times 100$ | 1.6849 | 0.7673 | 1.9770 | 0.5061 |
| Number of valid spots | 1632 | 1582 | 1577 | 1693 |
| Detection rate (%) | 63 | 61 | 61 | 65 |

TABLE 5-2

| | Comparative Examples | | | | | | | |
|---|---|---|---|---|---|---|---|---|
| | 1 | 2 | 3 | 4 | 5 | 6 | 7 | 8 |
| $(X_1/Y) \times 100$ | 3.2409 | 5.8310 | 0.9756 | 48.7612 | 6.0247 | 10.5768 | 31.1827 | 6.8341 |
| $(X_2/Y) \times 100$ | 0.8497 | 1.1752 | 1.4863 | 0.9060 | 4.6150 | 1.2687 | 3.5158 | 2.3335 |
| $(X_3/Y) \times 100$ | 1.4083 | 23.1438 | 20.1641 | 3.6846 | 2.2923 | 0.6588 | 12.0681 | 13.4320 |
| $((X_1 + X_2)/Y) \times 100$ | 4.0907 | 7.0062 | 2.4619 | 49.6672 | 10.6397 | 11.8455 | 34.6985 | 9.1676 |
| $((X_1 + X_3)/Y) \times 100$ | 4.6492 | 28.9748 | 21.1398 | 52.4458 | 8.3170 | 11.2356 | 43.2508 | 20.2661 |
| $((X_1 + X_2 + X_3)/Y) \times 100$ | 5.4989 | 30.1500 | 22.6260 | 53.3518 | 12.9320 | 12.5043 | 46.7666 | 22.5996 |
| $(X_4/Y) \times 100$ | 4.0791 | 552.7672 | 59.1357 | 7.7495 | 0.6646 | 0.7606 | 4.8257 | 112.8605 |
| $(X_5/Y) \times 100$ | 0.2498 | 2.0091 | 1.1990 | 0.1810 | 0.5888 | 0.2035 | 1.6713 | 1.6474 |
| $(X_6/Y) \times 100$ | 2.8091 | 8.0915 | 51.1585 | 0.6746 | 6.9167 | 0.6061 | 13.8523 | 12.1333 |
| $(X_7/Y) \times 100$ | 1.6913 | 974.7951 | 2.4228 | 59.6940 | 7.4215 | 2.8110 | 43.6874 | 243.4081 |
| $(X_8/Y) \times 100$ | 2.0806 | 221.0835 | 15.4770 | 37.5917 | 1.1462 | 0.2073 | 4.5999 | 38.7888 |
| $(X_9/Y) \times 100$ | 0.3915 | 195.7316 | 1.1908 | 10.6831 | 0.5153 | 0.8669 | 6.8208 | 168.2237 |
| $((X_6 + X_7)/Y) \times 100$ | 4.5004 | 982.8866 | 53.5813 | 60.3686 | 14.3382 | 3.4171 | 57.5397 | 255.5414 |
| $((X_8 + X_9)/Y) \times 100$ | 2.4721 | 416.8151 | 16.6679 | 48.2748 | 1.6615 | 1.0742 | 11.4206 | 207.0126 |
| $((X_6 + X_7 + X_8 + X_9)/Y) \times 100$ | 6.9725 | 1399.7017 | 70.2492 | 108.6435 | 15.9997 | 4.4912 | 68.9604 | 462.5539 |
| Number of valid spots | 1442 | 1080 | 1259 | 1241 | 1211 | 1153 | 1245 | 1205 |
| Detection rate (%) | 56 | 42 | 49 | 48 | 47 | 45 | 48 | 47 |

As shown in Tables 4-1, 4-2, 5-1 and 5-2, when each of the nucleic acid samples prepared by using the alkaline phosphatase compositions of Comparative Examples 1 to 8 was used in the nucleic acid detection method, the number of valid spots was less than 1,500, while, when each of the nucleic acid samples prepared by using the alkaline phosphatase compositions of Examples 1 to 4 was used in the nucleic acid detection method, the number of valid spots was 1,500 or more. The detection rates in Comparative Examples 1 to 8 were different although the alkaline phosphatase specific activities of the alkaline phosphatase compositions were almost the same, while the detection rates in Examples 1 to 4 were almost the same and were higher than the detection rates in Comparative Examples 1 to 8.

As shown in Tables 4-1, 4-2, 5-1 and 5-2, the value of $((X_1+X_2+X_3)/Y)\times 100$, which represents the content ratio of a total of the first to third peptide fragments to the alkaline phosphatase, was more than 5.0000 for each of the alkaline phosphatase compositions of Comparative Examples 1 to 8 (the minimum value was 5.4989 in the alkaline phosphatase composition of Comparative Example 1), while the value was 5.0000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $((X_1+X_2)/Y)\times 100$, which represents the content ratio of a total of the first and second peptide fragments to the alkaline phosphatase, was more than 2.4000 for each of the alkaline phosphatase compositions of Comparative Examples 1 to 8 (the minimum value was 2.4619 in the alkaline phosphatase composition of Comparative Example 3), while the value was 2.4000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $((X_1+X_3)/Y)\times 100$, which represents the content ratio of a total of the first and third peptide fragments to the alkaline phosphatase, was more than 4.5000 for each of the alkaline phosphatase compositions of Comparative Examples 1 to 8 (the minimum value was 4.6492 in the alkaline phosphatase composition of Comparative Example 1), while the value was 4.5000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_1/Y)\times 100$, which represents the content ratio of the first peptide fragment to the alkaline phosphatase, was more than 1.0000 for each of the alkaline phosphatase compositions of Comparative Examples 1, 2 and 4 to 8 (but 1.0000 or less for Comparative Example 3), while the value was 1.0000 or less for each of the alkaline phosphatase compositions of Examples 1 to 4. This is considered as one of the secondary causes of the difference in the effect between Examples 1 to 4 and Comparative Examples 1, 2 and 4 to 8.

As shown in Tables 4-1, 4-2, 5-1 and 5-2, the value of $(X_2/Y)\times 100$, which represents the content ratio of the second peptide fragment to the alkaline phosphatase, was more than 0.8000 for each of the alkaline phosphatase compositions of Comparative Examples 1 to 8 (the minimum value was 0.8497 in the alkaline phosphatase composition of Comparative Example 1), while the value was 0.8000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_3/Y)\times 100$, which represents the content ratio of the third peptide fragment to the alkaline phosphatase, was more than 2.3000 for each of the alkaline phosphatase compositions of Comparative Examples 2 to 4, 7 and 8 (but 2.3000 or less for each of Comparative Examples 1, 5 and 6), while the value was 2.3000 or less for each of the alkaline phosphatase compositions of Examples 1 to 4. This is considered as one of the secondary causes of the difference in the effect between Examples 1 to 4 and Comparative Examples 2 to 4, 7 and 8.

As shown in Tables 4-1, 4-2, 5-1 and 5-2, the value of $(X_4/Y) \times 100$, which represents the content ratio of the fourth peptide fragment to the alkaline phosphatase, was more than 0.6000 for each of the alkaline phosphatase compositions of Comparative Examples 1 to 8 (the minimum value was 0.6646 in the alkaline phosphatase composition of Comparative Example 5), while the value was 0.6000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_5/Y) \times 100$, which represents the content ratio of the fifth peptide fragment to the alkaline phosphatase, was more than 0.1800 for each of the alkaline phosphatase compositions of Comparative Examples 1 to 8 (the minimum value was 0.1810 in the alkaline phosphatase composition of Comparative Example 4), while the value was 0.1800 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $((X_6+X_7+X_8+X_9)/Y) \times 100$, which represents the content ratio of a total of the sixth to ninth peptide fragments to the alkaline phosphatase, was more than 4.4000 for each of the alkaline phosphatase compositions of Comparative Examples 1 to 8 (the minimum value was 4.4912 in the alkaline phosphatase composition of Comparative Example 6), while the value was 4.4000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $((X_6+X_7)/Y) \times 100$, which represents the content ratio of a total of the sixth and seventh peptide fragments to the alkaline phosphatase, was more than 3.4000 for each of the alkaline phosphatase compositions of Comparative Examples 1 to 8 (the minimum value was 3.4171 in the alkaline phosphatase composition of Comparative Example 6), while the value was 3.4000 or less for each of the alkaline phosphatase compositions of Examples 1 to 4. This is considered as one of the primary causes of difference in the effect mentioned above between Examples 1 to 4 and Comparative Examples 1 to 8.

As shown in Tables 4-1, 4-2, 5-1 and 5-2, the value of $((X_8+X_9)/Y) \times 100$, which represents the content ratio of a total of the eighth and ninth peptide fragments to the alkaline phosphatase, was more than 1.0000 for each of the alkaline phosphatase compositions of Comparative Examples 1 to 8 (the minimum value was 1.0742 in the alkaline phosphatase composition of Comparative Example 6), while the value was 1.0000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_6/Y) \times 100$, which represents the content ratio of the sixth peptide fragment to the alkaline phosphatase, was more than 1.0000 for each of the alkaline phosphatase compositions of Comparative Examples 1 to 3, 5, 7 and 8 (but 1.0000 or less for each of Comparative Examples 4 and 6), while the value was 1.0000 or less for each of the alkaline phosphatase compositions of Examples 1 to 4. This is considered as one of the secondary causes of the difference in the effect between Examples 1 to 4 and Comparative Examples 1 to 3, 5, 7 and 8.

As shown in Tables 4-1, 4-2, 5-1 and 5-2, the value of $(X_7/Y) \times 100$, which represents the content ratio of the seventh peptide fragment to the alkaline phosphatase, was more than 1.6000 for each of the alkaline phosphatase compositions of Comparative Examples 1 to 8 (the minimum value was 1.6913 in the alkaline phosphatase composition of Comparative Example 1), while the value was 1.6000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_8/Y) \times 100$, which represents the content ratio of the eighth peptide fragment to the alkaline phosphatase, was more than 0.2000 for each of the alkaline phosphatase compositions of Comparative Examples 1 to 8 (the minimum value was 0.2073 in the alkaline phosphatase composition of Comparative Example 6), while the value was 0.2000 or less for each of the alkaline phosphatase compositions of Examples 1 to 4. This is considered as one of the primary causes of the difference in the effect between Examples 1 to 4 and Comparative Examples 1 to 8.

As shown in Tables 4-1, 4-2, 5-1 and 5-2, the value of $(X_9/Y) \times 100$, which represents the content ratio of the ninth peptide fragment to the alkaline phosphatase, was more than 0.3500 for each of the alkaline phosphatase compositions of Comparative Examples 1 to 8 (the minimum value was 0.3915 in the alkaline phosphatase composition of Comparative Example 1), while the value was 0.3500 or less for each of the alkaline phosphatase compositions of Examples 1 to 4. This is considered as one of the primary causes of the difference in the effect between Examples 1 to 4 and Comparative Examples 1 to 8.

The invention claimed is:

1. A method of evaluating a quality of a dephosphorylation reagent, the method comprising the steps of:

making a dephosphorylation reagent comprising an alkaline phosphatase and a peptide fragment group (D1) composed of two or more peptide fragments, wherein each of the two or more peptide fragments consists of 5 to 50 consecutive amino acid residues selected from positions 501 to 578 of the amino acid sequence set forth in SEQ ID NO: 10;

determining a content ratio of the peptide fragment group (D1) to the alkaline phosphatase using formula (H1):
$(X_{D1}/Y) \times 100 < 4.4000$ (H1),
wherein $X_{D1}$ represents a peak area value of the peptide fragment group (D1) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent; and evaluating the dephosphorylation reagent as having a high quality if the content ratio of the peptide fragment group (D1) to the alkaline phosphatase satisfies formula (H1).

2. A method of evaluating a quality of a dephosphorylation reagent, the method comprising the steps of:

making a dephosphorylation reagent comprising an alkaline phosphatase and a peptide fragment group (D2) composed of two or more peptide fragments, wherein each of the two or more peptide fragments consists of 13 to 50 consecutive amino acid residues selected from positions 501 to 578 of the amino acid sequence set forth in SEQ ID NO: 10 and comprises positions 516 to 528 of the amino acid sequence set forth in SEQ ID NO: 10;

determining a content ratio of the peptide fragment group (D2) to the alkaline phosphatase using formula (H2):
$(X_{D2}/Y) \times 100 < 3.4000$ (H2),
wherein $X_{D2}$ represents a peak area value of the peptide fragment group (D2) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent; and evaluating the dephosphorylation reagent as having a high quality if the content ratio of the peptide fragment group (D2) to the alkaline phosphatase satisfies formula (H2).

3. A method of evaluating a quality of a dephosphorylation reagent, the method comprising the steps of:

making a dephosphorylation reagent comprising an alkaline phosphatase and a peptide fragment group (D3) composed of two or more peptide fragments, wherein each of the two or more peptide fragments consists of 12 to 50 consecutive amino acid residues selected from positions 501 to 578 of the amino acid sequence set forth in SEQ ID NO: 10 and comprises positions 534 to 545 of the amino acid sequence set forth in SEQ ID NO: 10;

determining a content ratio of the peptide fragment group (D3) to the alkaline phosphatase using formula ([H3]): $(X_{D3}/Y) \times 100 < 1.0000$ (H3), wherein $X_{D3}$ represents a peak area value of the peptide fragment group (D3) calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent; and evaluating the dephosphorylation reagent as having a high quality if the content ratio of the peptide fragment group (D3) to the alkaline phosphatase satisfies formula (H3).

4. A method of evaluating a quality of a dephosphorylation reagent, the method comprising the steps of:

making a dephosphorylation reagent comprising an alkaline phosphatase and a seventh peptide fragment consisting of the amino acid sequence set forth in SEQ ID NO: 7;

determining a content ratio of the seventh peptide fragment to the alkaline phosphatase using formula (7): $(X7/Y) \times 100 < 1.6000$ (7)

wherein $X_7$ represents a peak area value of the seventh peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent; and evaluating the dephosphorylation reagent as having a high quality if the content ratio of the seventh peptide fragment to the alkaline phosphatase satisfies formula (7).

5. A method of evaluating a quality of a dephosphorylation reagent, the method comprising the steps of:

making a dephosphorylation reagent comprising an alkaline phosphatase and an eighth peptide fragment consisting of the amino acid sequence set forth in SEQ ID NO: 8;

determining a content ratio of the eighth peptide fragment to the alkaline phosphatase using formula (8): $(X8/Y) \times 100 < 0.2000$ (8), wherein $X_8$ represents a peak area value of the eighth peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent; and evaluating the dephosphorylation reagent as having a high quality if the content ratio of the eighth peptide fragment to the alkaline phosphatase satisfies formula (8).

6. A method of evaluating a quality of a dephosphorylation reagent, the method comprising the steps of:

making a dephosphorylation reagent comprising an alkaline phosphatase and a ninth peptide fragment consisting of the amino acid sequence set forth in SEQ ID NO: 9;

determining a content ratio of the ninth peptide fragment to the alkaline phosphatase using formula (9): $(X9/Y) \times 100 < 0.3500$ (9), wherein $X_9$ represents a peak area value of the ninth peptide fragment calculated by an automatic integration method from an extracted ion chromatogram obtained by an LC-MS/MS analysis of the dephosphorylation reagent, and Y represents a peak area value of the alkaline phosphatase calculated by an automatic integration method from a chromatogram obtained by an LC-UV analysis of the dephosphorylation reagent; and evaluating the dephosphorylation reagent as having a high quality if the content ratio of the ninth peptide fragment to the alkaline phosphatase satisfies formula (9).

7. A method of evaluating a quality of a dephosphorylation reagent, the method comprising the steps of:

making a dephosphorylation reagent comprising
an alkaline phosphatase,
a second peptide fragment consisting of the amino acid sequence set forth in SEQ ID NO: 2,
a fourth peptide fragment consisting of the amino acid sequence set forth in SEQ ID NO: 4,
a fifth peptide fragment consisting of the amino acid sequence set forth in SEQ ID NO: 5,
a seventh peptide fragment consisting of the amino acid sequence set forth in SEQ ID NO: 7,
an eighth peptide fragment consisting of the amino acid sequence set forth in SEQ ID NO: 8, and
a ninth peptide fragment consisting of the amino acid sequence set forth in SEQ ID NO: 9;

determining content ratios of the second, fourth, fifth, seventh, eighth and ninth peptide fragments to the alkaline phosphatase using formulas (2), (4), (5), (7), (8) and (9), respectively:

$$(X_2/Y) \times 100 \leq 0.8000 \qquad (2),$$

$$(X_4/Y) \times 100 \leq 0.6000 \qquad (4),$$

$$(X_5/Y) \times 100 \leq 0.1800 \qquad (5),$$

$$(X_7/Y) \times 100 \leq 1.6000 \qquad (7),$$

$$(X_8/Y) \times 100 \leq 0.2000 \qquad (8), \text{ and}$$

$$(X_9/Y) \times 100 \leq 0.3500 \qquad (9),$$

wherein $X_2$, $X_4$, $X_5$, $X_7$, $X_8$ and $X_9$ represent peak area values of the second, fourth, fifth, seventh, eighth and ninth peptide fragments calculated by an automatic integration method from an extracted ion chromatogram obtained by an LC-MS/MS analysis of the dephosphorylation reagent, respectively, and Y represents a peak area value of the alkaline phosphatase calculated by an automatic integration method from a chromatogram obtained by an LC-UV analysis of the dephosphorylation reagent; and evaluating the dephosphorylation reagent as having a high quality if the content ratios of the second, fourth, fifth, seventh, eighth and ninth peptide fragments to the alkaline phosphatase satisfy formulas (2), (4), (5), (7), (8) and (9), respectively.

* * * * *